(12) United States Patent
Iwakoshi

(10) Patent No.: US 8,742,112 B2
(45) Date of Patent: Jun. 3, 2014

(54) HETEROCYCLIC COMPOUND AND ITS USE FOR CONTROL OF AN ARTHROPOD PEST

(75) Inventor: Mitsuhiko Iwakoshi, Toyonakak (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/499,717

(22) PCT Filed: Sep. 30, 2010

(86) PCT No.: PCT/JP2010/067609
§ 371 (c)(1),
(2), (4) Date: Apr. 2, 2012

(87) PCT Pub. No.: WO2011/043404
PCT Pub. Date: Apr. 14, 2011

(65) Prior Publication Data
US 2012/0196891 A1    Aug. 2, 2012

(30) Foreign Application Priority Data
Oct. 7, 2009   (JP) .................. 2009-233158

(51) Int. Cl.
*A61K 31/44* (2006.01)
*C07D 221/02* (2006.01)

(52) U.S. Cl.
USPC ......................... 546/112; 514/301

(58) Field of Classification Search
None
See application file for complete search history.

(56) References Cited

U.S. PATENT DOCUMENTS

| | | | |
|---|---|---|---|
| 4,556,411 A | 12/1985 | Baum et al. | |
| 5,585,247 A | 12/1996 | Habenstein | |
| 5,849,764 A | 12/1998 | Goulet et al. | |
| 2004/0254199 A1 | 12/2004 | Wood et al. | |
| 2005/0124497 A1 | 6/2005 | Fusslein et al. | |
| 2011/0039843 A1 | 2/2011 | Iwakoshi et al. | |
| 2012/0245167 A1 | 9/2012 | Iwakoshi et al. | |

FOREIGN PATENT DOCUMENTS

| | | |
|---|---|---|
| EP | 1000946 B1 | 10/2003 |
| GB | 2311010 A | 9/1997 |
| JP | 2000-143668 A | 5/2000 |
| JP | 2005-507431 A | 3/2005 |
| JP | 2005-521666 A | 7/2005 |
| WO | 0006566 A1 | 2/2000 |
| WO | 2002051821 A1 | 7/2002 |
| WO | 03064385 A2 | 8/2003 |
| WO | 2006024642 A1 | 3/2006 |
| WO | 2007010085 A2 | 1/2007 |
| WO | 2007091106 A2 | 8/2007 |
| WO | 2009019504 A1 | 2/2009 |
| WO | 2009131237 A1 | 10/2009 |

OTHER PUBLICATIONS

Extended European Search Report issued Jan. 25, 2013 in EP Application No. 10822074.0.
Int'l Search Report issued Nov. 2, 2010 in Int'l Application No. PCT/JP2010/067609.
Hisano et al, "Synthesis of Benzoxazoles, Benzothiazoles and Benzimidazoles and Evaluation of Their Antifungal, Insecticidal and Herbicidal Activities," Chemical & Pharmaceutical Bulletin, 30(8): 2996-3004 (1982).

*Primary Examiner* — Heidi Reese
(74) *Attorney, Agent, or Firm* — Panitch Schwarze Belisario & Nadel LLP

(57) ABSTRACT

A heterocyclic compound represented by formula (1):
wherein $A^1$, $A^2$, $R^1$, $R^2$, $R^3$, $R^4$, n and so on are defined in tha description,
has an excellent control effect on arthropod pests and is useful for control of arthropod pests.

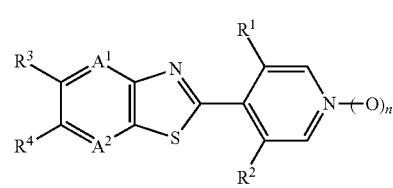

(1)

17 Claims, No Drawings

HETEROCYCLIC COMPOUND AND ITS USE FOR CONTROL OF AN ARTHROPOD PEST

CROSS-REFERENCE TO RELATED APPLICATION

This application is a Section 371 of International Application No. PCT/JP2010/067609, filed Sep. 30, 2010, which was published in the English language on Apr. 14, 2011, under International Publication No. WO 2011/043404 A1, and the disclosure of which is incorporated herein by reference.

TECHNICAL FIELD

The present invention relates to a certain kind of heterocyclic compound and its use for control of arthropod pests.

BACKGROUND ART

GB-A 2,311,010 describes a benzothiazole compound as a production intermediate for medicinal compounds. WO 2006/024642 describes a benzothiazole compound as a production intermediate for dyes. Chem. Pharm. Bull., 30(8), 2996 (1982) describes a certain kind of benzothiazole compound.

DISCLOSURE OF THE INVENTION

The present invention has an object of providing a compound having an excellent control effect on arthropod pests.

The present inventors have intensively investigated to solve the above-described problem, and resultantly found that a heterocyclic compound represented by the following formula (1) has an excellent control effect on arthropod pests, leading to completion of the present invention.

The present invention is as described below.

[1] A heterocyclic compound represented by formula (1):

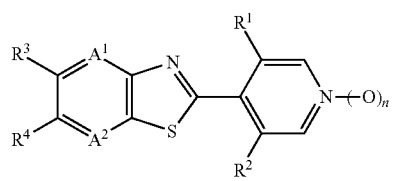

(1)

, wherein $A^1$ and $A^2$ are the same or different and represent a nitrogen atom or $=C(R^5)-$, $R^1$ represents a C1-C6 chain hydrocarbon group optionally substituted by at least one member selected from Group X, C3-C6 alicyclic hydrocarbon group optionally substituted by at least one member selected from Group X, phenyl group optionally substituted by at least one member selected from Group Y, 5-membered heterocyclic group optionally substituted by at least one member selected from Group Y, 6-membered heterocyclic group optionally substituted by at least one member selected from Group Y, $-OR^6$, $-S(O)_m R^6$, $-NR^6R^7$, $-NR^6C(O)R^8$, $-NR^6CO_2R^9$, $-C(O)R^{10}$, $-C(NOR^6)R^{10}$, cyano group, nitro group or halogen atom, $R^2$ represents a C1-C6 chain hydrocarbon group optionally substituted by at least one member selected from Group X, $-OR^6$, $-S(O)_m R^6$, $-NR^6R^7$, halogen atom or hydrogen atom, $R^3$ and $R^4$ are the same or different and represent a C1-C4 chain hydrocarbon group substituted by at least one halogen atom, $-OR^{11}$, $-S(O)_m R^{11}$, halogen atom or hydrogen atom (with the proviso that either $R^3$ or $R^4$ represents a C1-C4 chain hydrocarbon group substituted by at least one halogen atom, $-OR^{11}$ or $-S(O)_m R^{11}$), alternatively, $R^3$ and $R^4$ may be bound to form a 5-membered ring or 6-membered ring substituted by one or more halogen atoms together with the carbon atoms to which $R^3$ and $R^4$ are connected, $R^5$ represents a C1-C3 alkyl group optionally substituted by at least one halogen atom, halogen atom or hydrogen atom, $R^6$ and $R^7$ are the same or different and represent a C1-C6 chain hydrocarbon group optionally substituted by at least one member selected from Group X, C4-C7 cycloalkylmethyl group optionally substituted by at least one member selected from Group X, C3-C6 alicyclic hydrocarbon group optionally substituted by at least one member selected from Group X, phenyl group optionally substituted by at least one member selected from Group Y, benzyl group optionally substituted by at least one member selected from Group Y, 5-membered heterocyclic group optionally substituted by at least one member selected from Group Y, 6-membered heterocyclic group optionally substituted by at least one member selected from Group Y, or hydrogen atom (with the proviso that $R^6$ does not represent a hydrogen atom when m in $-S(O)_m R^6$ is 1 or 2), $R^8$ represents a C1-C6 chain hydrocarbon group optionally substituted by at least one member selected from Group X, C3-C6 alicyclic hydrocarbon group optionally substituted by at least one member selected from Group X, or phenyl group optionally substituted by at least one member selected from Group Y, $R^9$ represents a C1-C4 alkyl group optionally substituted by at least one halogen atom, $R^{10}$ represents a C1-C4 alkyl group optionally substituted by at least one halogen atom, or hydrogen atom, $R^{11}$ represents a C1-C4 chain hydrocarbon group substituted by at least one halogen atom, m represents 0, 1 or 2, and n represents 0 or 1.

Group X: the group consisting of C1-C4 alkoxy groups optionally substituted by at least one halogen atom, and halogen atoms.

Group Y: the group consisting of C1-C4 alkyl groups optionally substituted by at least one halogen atom, C1-C4 alkoxy groups optionally substituted by at least one halogen atom, cyano group, nitro group and halogen atoms.] (hereinafter, referred to as the present compound).

[2] The heterocyclic compound according to [1], wherein $R^5$ is a hydrogen atom.

[3] The heterocyclic compound according to [1] or [2], wherein $R^2$ is a hydrogen atom.

[4] The heterocyclic compound according to any one of [1] to [3], wherein $R^1$ is a C1-C6 chain hydrocarbon group optionally substituted by at least one member selected from Group X, $-OR^6$, $-S(O)_m R^6$, $-NR^6R^7$, $-NR^6C(O)R^8$, $-NR^6CO_2R^9$, $-C(O)R^{10}$, $-C(NOR^6)R^{10}$, cyano group, nitro group or halogen atom, $R^6$ and $R^7$ are the same or different and are a C1-C6 chain hydrocarbon group optionally substituted by at least one member selected from Group X, or hydrogen atom (with the proviso that $R^6$ is a C1-C6 chain hydrocarbon group optionally substituted by at least one member selected from Group X when m in $-S(O)_m R^6$ is 1 or 2), and $R^8$ is a C1-C6 chain hydrocarbon group optionally substituted by at least one member selected from Group X.

[5] The heterocyclic compound according to [4], wherein $R^1$ is a C1-C6 chain hydrocarbon group optionally substituted by at least one member selected from Group X, —$OR^6$, —$S(O)_mR^6$, —$NR^6R^7$ or halogen atom, $R^6$ is a C1-C6 chain hydrocarbon group optionally substituted by at least one member selected from Group X, and $R^7$ is a C1-C6 chain hydrocarbon group optionally substituted by at least one member selected from Group X, or hydrogen atom.

[6] An arthropod pest control composition comprising the heterocyclic compound as described in any one of [1] to [5], and an inert carrier.

[7] An arthropod pest control method comprising applying an effective amount of the heterocyclic compound as described in any one of [1] to [5] to arthropod pests or areas where arthropod pests live.

[8] Use of the heterocyclic compound as described in any one of [1] to [5] for control of arthropod pests.

The present compound has a control effect on arthropod pests.

MODE OF CARRYING OUT THE INVENTION

Substituents used in the descriptions of the present specification will be illustrated with examples mentioned below. In the present specification, for example, "C4-C7" in "C4-C7 cycloalkylmethyl group" means that the number of carbon atoms constituting the whole cycloalkylmethyl group is in the range of 4 to 7.

"Halogen atom" in the present compound means a fluorine atom, chlorine atom, bromine atom and iodine atom.

Examples of "C1-C6 chain hydrocarbon group optionally substituted by at least one member selected from Group X" represented by $R^1$ include C1-C6 alkyl groups such as a methyl group, ethyl group, propyl group, isopropyl group, butyl group, isobutyl group, sec-butyl group, tert-butyl group, pentyl group, 2,2-dimethylpropyl group, 3-methylbutyl group, 2,3-dimethylbutyl group, 3,3-dimethylbutyl group and hexyl group;

C1-C6 alkyl groups substituted by at least one member selected from Group X such as a methoxymethyl group, ethoxymethyl group, 1-methoxyethyl group and trifluoromethyl group;

C2-C6 alkenyl groups such as a vinyl group, 1-propenyl group, 2-propenyl group, isopropenyl group, 2-methyl-1-propenyl group, 1-butenyl group, 2-butenyl group, 3-butenyl group, 1-pentenyl group and 1-hexenyl group;

C2-C6 alkenyl groups substituted by at least one member selected from Group X such as a 3,3-difluoro-2-propenyl group and 3-methoxy-1-propenyl group;

C2-C6 alkynyl groups such as an ethynyl group, propargyl group, 1-butynyl group, 2-butynyl group, 3-butynyl group, 3,3-dimethyl-1-butynyl group, 1-pentynyl group and 1-hexynyl group; and C2-C6 alkynyl groups substituted by at least one member selected from Group X such as a 3-methoxy-1-propynyl group.

Examples of "C3-C6 alicyclic hydrocarbon group optionally substituted by at least one member selected from Group X" represented by $R^1$ include a cyclopropyl group, cyclobutyl group, cyclopentyl group and cyclohexyl group.

Examples of "phenyl group optionally substituted by at least one member selected from Group Y" represented by $R^1$ include a phenyl group, 2-chlorophenyl group, 3-chlorophenyl group, 4-chlorophenyl group, 2-methylphenyl group, 3-methylphenyl group, 4-methylphenyl group, 2-methoxyphenyl group, 3-methoxyphenyl group, 4-methoxyphenyl group, 2-(trifluoromethyl)phenyl group, 3-(trifluoromethyl)phenyl group, 4-(trifluoromethyl)phenyl group, 2-nitrophenyl group, 3-nitrophenyl group, 4-nitrophenyl group, 2-cyanophenyl group, 3-cyanophenyl group and 4-cyanophenyl group.

Examples of "5-membered heterocyclic group optionally substituted by at least one member selected from Group Y" represented by $R^1$ include 5-membered saturated heterocyclic groups such as a pyrrolidin-1-yl group and the like; and 5-membered aromatic heterocyclic groups such as a pyrazol-1-yl group, 3-chloropyrazol-1-yl group, 3-bromopyrazol-1-yl group, 3-nitropyrazol-1-yl group, 3-methylpyrazol-1-yl group, 3-(trifluoromethyl)pyrazol-1-yl group, 4-methylpyrazol-1-yl group, 4-chloropyrazol-1-yl group, 4-bromopyrazol-1-yl group, 4-cyanopyrazol-1-yl group, imidazol-1-yl group, 4-(trifluoromethyl)imidazol-1-yl group, pyrrol-1-yl group, 1,2,4-triazol-1-yl group, 3-chloro-1,2,4-triazol-1-yl group, 1,2,3,4-tetrazol-1-yl group, 1,2,3,5-tetrazol-1-yl group, 2-furyl group, 3-furyl group, 2-thienyl group and 3-thienyl group.

"6-membered heterocyclic group optionally substituted by at least one member selected from Group Y" represented by $R^1$ include 6-membered saturated heterocyclic groups such as a piperidyl group, morpholino group, thiomorpholino group and 4-methylpiperazin-1-yl group and the like; and 6-membered aromatic heterocyclic groups such as a 2-pyridyl group, 3-pyridyl group and 4-pyridyl group.

Examples of "C1-C6 chain hydrocarbon group optionally substituted by at least one member selected from Group X" represented by $R^2$ include C1-C6 alkyl groups such as a methyl group, ethyl group, propyl group, isopropyl group, butyl group, isobutyl group, sec-butyl group, tert-butyl group, pentyl group, 2,2-dimethylpropyl group, 3-methylbutyl group, 2,3-dimethylbutyl group, 3,3-dimethylbutyl group and hexyl group;

C1-C6 alkyl groups substituted by at least one member selected from Group X such as a methoxymethyl group, ethoxymethyl group, 1-methoxyethyl group and trifluoromethyl group;

C2-C6 alkenyl groups such as a vinyl group, 1-propenyl group, 2-propenyl group, isopropenyl group, 2-methyl-1-propenyl group, 1-butenyl group, 2-butenyl group, 3-butenyl group, 1-pentenyl group and 1-hexenyl group and the like;

C2-C6 alkenyl groups substituted by at least one member selected from Group X such as a 3,3-difluoro-2-propenyl group and 3-methoxy-1-propenyl group;

C2-C6 alkynyl groups such as an ethynyl group, propargyl group, 1-butynyl group, 2-butynyl group, 3-butynyl group, 3,3-dimethyl-1-butynyl group, 1-pentynyl group and 1-hexynyl group; and C2-C6 alkynyl groups substituted by at least one member selected from Group X such as a 3-methoxy-1-propynyl group.

Examples of "C1-C4 chain hydrocarbon group substituted by at least one halogen atom" represented by $R^3$ or $R^4$ include a trifluoromethyl group, 1,1-difluoroethyl group, 2,2,2-trifluoroethyl group, pentafluoroethyl group and heptafluoroisopropyl group.

Examples of "C1-C3 alkyl group optionally substituted by at least one halogen atom" represented by $R^5$ include a methyl group, ethyl group, propyl group, isopropyl group and trifluoromethyl group.

Examples of "C1-C6 chain hydrocarbon group optionally substituted by at least one member selected from Group X" represented by $R^6$ or $R^7$ include C1-C6 alkyl groups such as a methyl group, ethyl group, propyl group, isopropyl group, butyl group, isobutyl group, sec-butyl group, tert-butyl group, 1-methylbutyl group, 2-methylbutyl group, 3-methylbutyl group, 1-ethylpropyl group, 1,2-dimethylpropyl group, 2,2-dimethylpropyl group, pentyl group, 1,2-dimethylbutyl group, 2,2-dimethylbutyl group, 1,3-dimethylbutyl group, 1-methylpentyl group, 2-methylpentyl group, 3-methylpentyl group, 4-methylpentyl group and hexyl group;

C1-C6 alkyl groups substituted by at least one member selected from Group X such as a 2-methoxyethyl group, 2-ethoxyethyl group, difluoromethyl group, trifluoromethyl group, 2,2-difluoroethyl group, 2,2,2-trifluoroethyl group, 2,2,2-trichloroethyl group, 1-methyl-2,2,2-trifluoroethyl group, 1-methyl-2,2,2-trichloroethyl group, 1,1,2,2-tetrafluoroethyl group, 2,2-difluoropropyl group and 2,2,3,3-tetrafluoropropyl group;

C3-C6 alkenyl groups such as a 2-propenyl group, 1-methyl-2-propenyl group, 2-methyl-2-propenyl group, 2-butenyl group, 3-butenyl group, 1-methyl-2-butenyl group and 1-methyl-3-butenyl group;

C3-C6 alkenyl groups substituted by at least one member selected from Group X such as a 3,3-dichloro-2-propenyl group, 3,3-difluoro-2-propenyl group; and C3-C6 alkynyl groups optionally substituted by at least one member selected from Group X such as a propargyl group, 1-methyl-2-propynyl group, 2-butynyl group, 3-butynyl group, 1-methyl-2-butynyl group and 1-methyl-3-butynyl group.

Examples of the C4-C7 cycloalkylmethyl group represented by $R^6$ or $R^7$ include a cyclopropylmethyl group, cyclobutylmethyl group, cyclopentylmethyl group and cyclohexylmethyl group.

Examples of the C3-C6 alicyclic hydrocarbon group represented by $R^6$ or $R^7$ include a cyclopropyl group, cyclobutyl group, cyclopentyl group, cyclohexyl group and 2-cyclohexenyl group.

Examples of "phenyl group optionally substituted by at least one member selected from Group Y" represented by $R^6$ or $R^7$ include a phenyl group, 2-chlorophenyl group, 3-chlorophenyl group, 4-chlorophenyl group, 2-methylphenyl group, 3-methylphenyl group, 4-methylphenyl group, 2-methoxyphenyl group, 3-methoxyphenyl group, 4-methoxyphenyl group, 2-(trifluoromethyl)phenyl group, 3-(trifluoromethyl)phenyl group, 4-(trifluoromethyl)phenyl group, 2-cyanophenyl group, 3-cyanophenyl group, 4-cyanophenyl group, 2-nitrophenyl group, 3-nitrophenyl group and 4-nitrophenyl group.

Examples of "benzyl group optionally substituted by at least one member selected from Group Y" represented by $R^6$ or $R^7$ include a benzyl group, 2-chlorobenzyl group, 3-chlorobenzyl group, 4-chlorobenzyl group, 2-methylbenzyl group, 3-methylbenzyl group, 4-methylbenzyl group, 2-methoxybenzyl group, 3-methoxybenzyl group and 4-methoxybenzyl group.

Examples of "5-membered heterocyclic group" represented by $R^6$ or $R^7$ include 5-membered aromatic heterocyclic groups such as a 2-thiazolyl group, 2-thienyl group and 3-thienyl group.

Examples of "6-membered heterocyclic group" represented by $R^6$ or $R^7$ include 6-membered aromatic heterocyclic groups such as a 2-pyridyl group, 3-pyridyl group, 4-pyridyl group, 2-pyrimidinyl group and 4-pyrimidinyl group.

Examples of "C1-C6 chain hydrocarbon group optionally substituted by at least one member selected from Group X" represented by $R^8$ include C1-C6 alkyl groups such as a methyl group, ethyl group, propyl group, isopropyl group, butyl group, isobutyl group, sec-butyl group, tert-butyl group, 1-methylbutyl group, 1-ethylpropyl group, pentyl group and hexyl group;

C1-C6 alkyl groups substituted by at least one member selected from Group X such as a methoxymethyl group, difluoromethyl group, trifluoromethyl group, trichloromethyl group, pentafluoroethyl group and 1,1,2,2-tetrafluoroethyl group;

C2-C6 alkenyl groups optionally substituted by at least one member selected from Group X such as a vinyl group, 1-propenyl group, 2-propenyl group, isopropenyl group, 2,2-dimethylethenyl group, 1-butenyl group, 2-butenyl group and 3,3,3-trifluoro-1-propenyl group; and C2-C6 alkynyl groups optionally substituted by at least one member selected from Group X such as a propargyl group, 1-propynyl group and 3,3,3-trifluoro-1-propynyl group.

Examples of the C3-C6 alicyclic hydrocarbon group represented by $R^8$ include a cyclopropyl group, cyclobutyl group, cyclopentyl group and cyclohexyl group.

Examples of "phenyl group optionally substituted by at least one member selected from Group Y" represented by $R^8$ include a phenyl group, 2-chlorophenyl group, 3-chlorophenyl group, 4-chlorophenyl group, 2-methylphenyl group, 3-methylphenyl group, 4-methylphenyl group, 2-methoxyphenyl group, 3-methoxyphenyl group, 4-methoxyphenyl group, 2-(trifluoromethyl)phenyl group, 3-(trifluoromethyl)phenyl group, 4-(trifluoromethyl)phenyl group, 2-cyanophenyl group, 3-cyanophenyl group, 4-cyanophenyl group, 2-nitrophenyl group, 3-nitrophenyl group and 4-nitrophenyl group.

Examples of "C1-C4 alkyl group optionally substituted by at least one halogen atom" represented by $R^9$ include a methyl group, ethyl group, 2,2,2-trifluoroethyl group, propyl group, isopropyl group, butyl group, isobutyl group, sec-butyl group and tert-butyl group.

Examples of "C1-C4 alkyl group optionally substituted by at least one halogen atom" represented by $R^{10}$ include a methyl group, trifluoromethyl group, trichloromethyl group, ethyl group, 2,2,2-trifluoroethyl group, pentafluoroethyl group, propyl group, isopropyl group, butyl group, isobutyl group, sec-butyl group and tert-butyl group.

Examples of "C1-C4 chain hydrocarbon group substituted by at least one halogen atom" represented by $R^{11}$ include a trifluoromethyl group, difluoromethyl group and 2,2,2-trifluoroethyl group.

Examples of the present compound include the following compounds.

Compounds of formula (1) in which $R^5$ represents a hydrogen atom;

Compounds of formula (1) in which $R^2$ represents a halogen atom or hydrogen atom;

Compounds of formula (1) in which $R^2$ represents a hydrogen atom;

Compounds of formula (1) in which $R^1$ represents a C3-C6 alicyclic hydrocarbon group optionally substituted by at least one member selected from Group X, phenyl group optionally substituted by at least one member selected from Group Y, 5-membered heterocyclic group optionally substituted by at least one member selected from Group Y, or 6-membered heterocyclic group optionally substituted by at least one member selected from Group Y;

Compounds of formula (1) in which $R^1$ represents a C1-C6 chain hydrocarbon group optionally substituted by at least one member selected from Group X, $-OR^6$, $-S(O)_mR^6$, $-NR^6R^7$, $-NR^6C(O)R^8$, $-NR^6CO_2R^9$, $-C(O)R^{10}$, $-C(NOR^6)R^{10}$, cyano group, nitro group or halogen atom, $R^6$ and $R^7$ are the same or different and represent a C1-C6 chain hydrocarbon group optionally substituted by at least one member selected from Group X, or hydrogen atom (with the proviso that if m in $-S(O)_mR^6$ is 1 or 2, then, $R^6$ represents a C1-C6 chain hydrocarbon group optionally substituted by at least one member selected from Group X), $R^8$ represents a C1-C6 chain hydrocarbon group optionally substituted by at least one member selected from Group X;

Compounds of formula (1) in which $R^1$ represents a C1-C6 chain hydrocarbon group optionally substituted by at least one member selected from Group X, —$OR^6$, —$S(O)_mR^6$, —$NR^6R^7$ or halogen atom, $R^6$ represents a C1-C6 chain hydrocarbon group optionally substituted by at least one member selected from Group X, $R^7$ represents a C1-C6 chain hydrocarbon group optionally substituted by at least one member selected from Group X or hydrogen atom;

Compounds of formula (1) in which $R^1$ represents a C1-C6 chain hydrocarbon group optionally substituted by at least one member selected from Group X, —$OR^6$, —$S(O)_mR^6$ or halogen atom, $R^6$ represents a C1-C6 chain hydrocarbon group optionally substituted by at least one member selected from Group X;

Compounds of formula (1) in which $R^1$ represents —$OR^6$, —$S(O)_mR^6$ or halogen atom, $R^6$ represents C1-C6 chain hydrocarbon group optionally substituted by at least one member selected from Group X;

Compounds of formula (1) in which either $R^3$ or $R^4$ represents a C1-C4 chain hydrocarbon group substituted by at least one halogen atom, —$OR^{11}$ or $S(O)_mR^{11}$;

Compounds of formula (1) in which either $R^3$ or $R^4$ represents a C1-C4 chain hydrocarbon group substituted by at least one fluorine atom, —$OR^{11}$ or —$S(O)_mR^{11}$, $R^{11}$ represents a C1-C4 chain hydrocarbon group substituted by at least one fluorine atom;

Compounds of formula (1) in which either $R^3$ or $R^4$ represents a trifluoromethyl group, —$OR^{11}$ or —$S(O)_mR^{11}$, $R^{11}$ represents a trifluoromethyl group;

Compounds of formula (1) in which $R^3$ represents a C1-C4 chain hydrocarbon group substituted by at least one halogen atom, or —$OR^{11}$;

Compounds of formula (1) in which $R^4$ represents a C1-C4 chain hydrocarbon group substituted by at least one halogen atom, or —$OR^{11}$;

Compounds of formula (1) in which $R^3$ represents a C1-C4 chain hydrocarbon group substituted by at least one halogen atom;

Compounds of formula (1) in which $R^3$ represents a C1-C4 chain hydrocarbon group substituted by at least one fluorine atom;

Compounds of formula (1) in which $R^3$ represents a trifluoromethyl group;

Compounds of formula (1) in which $R^4$ represents a C1-C4 chain hydrocarbon group substituted by at least one halogen atom;

Compounds of formula (1) in which $R^4$ represents a C1-C4 chain hydrocarbon group substituted by at least one fluorine atom;

Compounds of formula (1) in which $R^4$ represents a trifluoromethyl group;

Compounds of formula (1) in which $R^3$ represents —$OR^{11}$;

Compounds of formula (1) in which $R^3$ represents —$OR^{11}$, $R^{11}$ represents a C1-C4 chain hydrocarbon group substituted by at least one fluorine atom;

Compounds of formula (1) in which $R^3$ represents —$OR^{11}$, $R^{11}$ represents a trifluoromethyl group;

Compounds of formula (1) in which $R^4$ represents —$OR^{11}$;

Compounds of formula (1) in which $R^4$ represents —$OR^{11}$, $R^{11}$ represents a C1-C4 chain hydrocarbon group substituted by at least one fluorine atom;

Compounds of formula (1) in which $R^4$ represents —$OR^{11}$, $R^{11}$ represents a trifluoromethyl group;

Compounds of formula (1) in which $R^3$ represents a C1-C4 chain hydrocarbon group substituted by at least one halogen atom, $R^4$ represents a hydrogen atom;

Compounds of formula (1) in which $R^3$ represents —$OR^{11}$, $R^{11}$ represents a C1-C4 chain hydrocarbon group substituted by at least one fluorine atom, $R^4$ represents a hydrogen atom;

Compounds of formula (1) in which $R^3$ represents a C1-C4 chain hydrocarbon group substituted by at least one fluorine atom, $R^4$ represents a hydrogen atom;

Compounds of formula (1) in which $R^3$ represents a hydrogen atom, $R^4$ represents a C1-C4 chain hydrocarbon group substituted by at least one halogen atom;

Compounds of formula (1) in which $R^3$ represents a hydrogen atom, $R^4$ represents a C1-C4 chain hydrocarbon group substituted by at least one fluorine atom;

Compounds of formula (1) in which $R^3$ represents a hydrogen atom, $R^4$ represents —$OR^{11}$, $R^{11}$ represents a C1-C4 chain hydrocarbon group substituted by at least one fluorine atom;

Compounds of formula (1) in which $R^3$ represents a trifluoromethyl group, $R^4$ represents a hydrogen atom;

Compounds of formula (1) in which $R^3$ represents —$OR^{11}$, $R^{11}$ represents a trifluoromethyl group, $R^4$ represents a hydrogen atom;

Compounds of formula (1) in which $R^3$ represents a hydrogen atom, $R^4$ represents a trifluoromethyl group;

Compounds of formula (1) in which $R^3$ represents a hydrogen atom, $R^4$ represents —$OR^{11}$, $R^{11}$ represents a trifluoromethyl group;

Compounds of formula (1) in which $A^1$ represents =$C(R^5)$—, $A^2$ represents a nitrogen atom or =$C(R^5)$—;

Compounds of formula (1) in which $A^1$ represents =$C(R^5)$—, $A^2$ represents a nitrogen atom or =$C(R^5)$—, $R^5$ represents a hydrogen atom;

Compounds of formula (1) in which $A^1$ represents a nitrogen atom, $A^2$ represents =$C(R^5)$—, $R^5$ represents a hydrogen atom;

Compounds of formula (1) in which $A^1$ represents =$C(R^5)$—, $A^2$ represents a nitrogen atom, $R^5$ represents a hydrogen atom;

Compounds of formula (1) in which $A^1$ and $A^2$ represent =$C(R^5)$—, $R^5$ represents a hydrogen atom;

Compounds of formula (1) in which $R^1$ represents a C1-C4 alkyl group optionally substituted by at least one halogen atom, C2-C4 alkenyl group, pyrrolidyl group, piperidyl group, morpholino group, imidazolyl group, pyrazolyl group, triazolyl group, pyrazolyl group substituted by at least one C1-C3 alkyl group, pyrazolyl group substituted by at least one (C1-C3 alkyl group substituted by at least one halogen atom), phenyl group, pyridyl group, —$OR^{6a}$ ($R^{6a}$ represents a C1-C4 alkyl group optionally substituted by at least one halogen atom, C3-C4 alkenyl group optionally substituted by at least one halogen atom, C3-C4 alkynyl group, benzyl group or C4-C7 cycloalkylmethyl group), —$S(O)_mR^{6b}$ ($R^{6b}$ represents a C1-C4 alkyl group optionally substituted by at least one halogen atom. m represents 0, 1 or 2), —$NR^{6c}R^{7a}$ ($R^{6c}$ and $R^{7a}$ are the same or different and represent a C1-C4 alkyl group optionally substituted by at least one halogen atom, or hydrogen atom), —$NHC(O)R^8$ or halogen atom, $R^2$ represents a halogen atom or hydrogen atom, $R^8$ represents a C1-C4 alkyl group optionally substituted by at least one halogen atom;

Compounds of formula (1) in which $R^1$ represents a C1-C4 alkyl group optionally substituted by at least one halogen atom, C2-C4 alkenyl group, pyrrolidyl group, piperidyl group, morpholino group, imidazolyl group, pyrazolyl group, triazolyl group, pyrazolyl group substituted by at least one C1-C3 alkyl group, pyrazolyl group substituted by at least one (C1-C3 alkyl group substituted by at least one halogen atom), phenyl group, pyridyl group, —$OR^{6a}$ ($R^{6a}$ represents a C1-C4 alkyl group optionally substituted by at least one halogen atom, C3-C4 alkenyl group optionally substituted by at least one halogen atom, C3-C4 alkynyl group, benzyl group or C4-C7 cycloalkylmethyl group), —$S(O)_mR^{6b}$ ($R^{6b}$ represents a C1-C4 alkyl group optionally substituted by at least one halogen atom. m represents 0, 1 or 2), —$NR^{6c}R^{7a}$ ($R^{6c}$ and $R^{7a}$ are the same or different and represent a C1-C4 alkyl group optionally substituted by at least one halogen atom, or hydrogen atom), —$NHC(O)R^8$ or halogen atom, $R^2$ represents a hydrogen atom, $R^5$ represents a hydrogen atom, $R^8$ represents a C1-C4 alkyl group optionally substituted by at least one halogen atom;

Compounds of formula (1) in which $R^1$ represents a C1-C4 alkyl group optionally substituted by at least one halogen atom, C2-C4 alkenyl group, pyrrolidyl group, piperidyl group, morpholino group, imidazolyl group, pyrazolyl group, triazolyl group, pyrazolyl group substituted by at least one C1-C3 alkyl group, pyrazolyl group substituted by at least one (C1-C3 alkyl group substituted by at least one halogen atom), phenyl group, pyridyl group, —$OR^{6a}$ ($R^{6a}$ represents a C1-C4 alkyl group optionally substituted by at least one halogen atom, C3-C4 alkenyl group optionally substituted by at least one halogen atom, C3-C4 alkynyl group, benzyl group or C4-C7 cycloalkylmethyl group), —$S(O)_mR^{6b}$ ($R^{6b}$ represents a C1-C4 alkyl group optionally substituted by at least one halogen atom. m represents 0, 1 or 2), —$NR^{6c}R^{7a}$ ($R^{6c}$ and $R^{7a}$ are the same or different and represent a C1-C4 alkyl group optionally substituted by at least one halogen atom, or hydrogen atom), —$NHC(O)R^8$ or halogen atom, $R^2$ represents a hydrogen atom, $R^3$ represents a C1-C4 chain hydrocarbon group substituted by at least one halogen atom, or —$OR^{11}$, $R^4$ represents a hydrogen atom, $R^5$ represents a hydrogen atom, $R^8$ represents a C1-C4 alkyl group optionally substituted by at least one halogen atom;

Compounds of formula (1) in which $R^1$ represents a C1-C4 alkyl group optionally substituted by at least one halogen atom, C2-C4 alkenyl group, pyrrolidyl group, piperidyl group, morpholino group, imidazolyl group, pyrazolyl group, triazolyl group, pyrazolyl group substituted by at least one C1-C3 alkyl group, pyrazolyl group substituted by at least one (C1-C3 alkyl group substituted by at least one halogen atom), phenyl group, pyridyl group, —$OR^{6a}$ ($R^{6a}$ represents a C1-C4 alkyl group optionally substituted by at least one halogen atom, C3-C4 alkenyl group optionally substituted by at least one halogen atom, C3-C4 alkynyl group, benzyl group or C4-C7 cycloalkylmethyl group), —$S(O)_mR^{6b}$ ($R^{6b}$ represents a C1-C4 alkyl group optionally substituted by at least one halogen atom. m represents 0, 1 or 2), —$NR^{6c}R^{7a}$ ($R^{6c}$ and $R^{7a}$ are the same or different and represent a C1-C4 alkyl group optionally substituted by at least one halogen atom, or hydrogen atom), —$NHC(O)R^8$ or halogen atom, $R^2$ represents a hydrogen atom, $R^3$ represents a trifluoromethyl group, $R^4$ represents a hydrogen atom, $R^5$ represents a hydrogen atom, $R^8$ represents a C1-C4 alkyl group optionally substituted by at least one halogen atom;

Compounds of formula (1) in which $R^1$ represents a C1-C4 alkyl group optionally substituted by at least one halogen atom, —$OR^{6a}$ ($R^{6a}$ represents a C1-C4 alkyl group optionally substituted by at least one halogen atom), —$S(O)_mR^{6a}$ (m represents 0, 1 or 2), —$NR^{6b}R^{7a}$ ($R^{6b}$ and $R^{7a}$ are the same or different and represent a C1-C4 alkyl group optionally substituted by at least one halogen atom, or hydrogen atom), or halogen atom;

Compounds of formula (1) in which $R^1$ represents a C1-C4 alkyl group optionally substituted by at least one halogen atom, —$OR^{6a}$ ($R^{6a}$ represents a C1-C4 alkyl group optionally substituted by at least one halogen atom), —$S(O)_mR^{6a}$ (m represents 0, 1 or 2), —$NR^{6b}R^{7a}$ ($R^{6b}$ and $R^{7a}$ are the same or different and represent a C1-C4 alkyl group optionally substituted by at least one halogen atom, or hydrogen atom), or halogen atom, $R^2$ represents a halogen atom or hydrogen atom;

Compounds of formula (1) in which $R^1$ represents a C1-C4 alkyl group optionally substituted by at least one halogen atom, —$OR^{6b}$ ($R^{6a}$ represents a C1-C4 alkyl group optionally substituted by at least one halogen atom), —$S(O)_mR^{6a}$ (m represents 0, 1 or 2), —$NR^{6b}R^{7a}$ ($R^{6b}$ and $R^{7a}$ are the same or different and represent a C1-C4 alkyl group optionally substituted by at least one halogen atom, or hydrogen atom), or halogen atom, $R^2$ represents a hydrogen atom, $R^5$ represents a hydrogen atom;

Compounds of formula (1) in which $R^1$ represents a C1-C4 alkyl group optionally substituted by at least one halogen atom, —$OR^{6b}$ ($R^{6a}$ represents a C1-C4 alkyl group optionally substituted by at least one halogen atom), —$S(O)_mR^{6a}$ (m represents 0, 1 or 2), —$NR^{6b}R^{7a}$ ($R^{6b}$ and $R^{7a}$ are the same or different and represent a C1-C4 alkyl group optionally substituted by at least one halogen atom, or hydrogen atom), or halogen atom, $R^2$ represents a hydrogen atom, $R^3$ represents a C1-C4 chain hydrocarbon group substituted by at least one halogen atom, or —$OR_{11}$, $R^4$ represents a hydrogen atom, $R^5$ represents a hydrogen atom;

Compounds of formula (1) in which $R^1$ represents a C1-C4 alkyl group optionally substituted by at least one halogen atom, —$OR^{6a}$ ($R^{6a}$ represents a C1-C4 alkyl group optionally substituted by at least one halogen atom), —$S(O)_mR^{6a}$ (m represents 0, 1 or 2), —$NR^{6b}R^{7a}$ ($R^{6b}$ and $R^{7a}$ are the same or different and represent a C1-C4 alkyl group optionally substituted by at least one halogen atom, or hydrogen atom), or halogen atom, $R^2$ represents a hydrogen atom, $R^3$ represents a C1-C4 chain hydrocarbon group substituted by at least one halogen atom, $R^4$ represents a hydrogen atom, $R^5$ represents a hydrogen atom;

Compounds of formula (1) in which $R^1$ represents a C1-C4 alkyl group optionally substituted by at least one halogen atom, —$OR^{6a}$ ($R^{6a}$ represents a C1-C4 alkyl group optionally substituted by at least one halogen atom), —$S(O)_m R^{6a}$ (m represents 0, 1 or 2), —$NR^{6b}R^{7a}$ ($R^{6b}$ and $R^{7a}$ are the same or different and represent a C1-C4 alkyl group optionally substituted by at least one halogen atom, or hydrogen atom), or halogen atom, $R^2$ represents a hydrogen atom, $R^3$ represents a hydrogen atom, $R^4$ represents a C1-C4 chain hydrocarbon group substituted by at least one halogen atom, or —$OR^{11}$, $R^5$ represents a hydrogen atom;

Compounds of formula (1) in which $R^1$ represents a C1-C4 alkyl group optionally substituted by at least one halogen atom, —$OR^{6a}$ ($R^{6a}$ represents a C1-C4 alkyl group optionally substituted by at least one halogen atom), —$S(O)_m R^{6a}$ (m represents 0, 1 or 2), —$NR^{6b}R^{7a}$ ($R^{6b}$ and $R^{7a}$ are the same or different and represent a C1-C4 alkyl group optionally substituted by at least one halogen atom, or hydrogen atom), or halogen atom, $R^2$ represents a hydrogen atom, $R^3$ represents a hydrogen atom, $R^4$ represents a C1-C4 chain hydrocarbon group substituted by at least one halogen atom, $R^5$ represents a hydrogen atom;

Compounds of formula (1) in which $R^1$ represents a C1-C4 alkyl group optionally substituted by at least one halogen atom, —$OR^{6a}$ ($R^{6a}$ represents a C1-C4 alkyl group optionally substituted by at least one halogen atom), —$S(O)_m R^{6a}$ (m represents 0, 1 or 2), —$NR^{6b}R^{7a}$ ($R^{6b}$ and $R^{7a}$ are the same or different and represent a C1-C4 alkyl group optionally substituted by at least one halogen atom, or hydrogen atom), or halogen atom, $R^2$ represents a hydrogen atom, $R^3$ represents a C1-C4 chain hydrocarbon group substituted by at least one fluorine atom, $R^4$ represents a hydrogen atom, $R^5$ represents a hydrogen atom;

Compounds of formula (1) in which $R^1$ represents a C1-C4 alkyl group optionally substituted by at least one halogen atom, —$OR^{6a}$ ($R^{6a}$ represents a C1-C4 alkyl group optionally substituted by at least one halogen atom), —$S(O)_m R^{6a}$ (m represents 0, 1 or 2), —$NR^{6b}R^{7a}$ ($R^{6b}$ and $R^{7a}$ are the same or different and represent a C1-C4 alkyl group optionally substituted by at least one halogen atom, or hydrogen atom), or halogen atom, $R^2$ represents a hydrogen atom, $R^3$ represents a trifluoromethyl group, $R^4$ represents a hydrogen atom, $R^5$ represents a hydrogen atom;

Compounds of formula (1) in which $A^1$ represents =$C(R^5)$—, $A^2$ represents a nitrogen atom or =$C(R^5)$—, $R^1$ represents a C1-C4 alkyl group optionally substituted by at least one halogen atom, —$OR^{6a}$ ($R^{6a}$ represents a C1-C4 alkyl group optionally substituted by at least one halogen atom), —$S(O)_m R^{6a}$ (m represents 0, 1 or 2), —$NR^{6b}R^{7a}$ ($R^{6b}$ and $R^{7a}$ are the same or different and represent a C1-C4 alkyl group optionally substituted by at least one halogen atom, or hydrogen atom) or halogen atom, $R^2$ represents a hydrogen atom, $R^3$ represents a trifluoromethyl group, $R^4$ represents a hydrogen atom, $R^5$ represents a hydrogen atom;

Compounds of formula (1) in which $R^1$ represents a C1-C4 alkyl group optionally substituted by at least one halogen atom, —$OR^6$, —$S(O)_m R^6$ (m represents 0, 1 or 2) or halogen atom, $R^2$ represents a hydrogen atom, $R^3$ represents a trifluoromethyl group, $R^4$ represents a hydrogen atom, $R^5$ represents a hydrogen atom, $R^6$ represents a C1-C4 alkyl group optionally substituted by at least one halogen atom;

Compounds of formula (1) in which $A^1$ represents =$C(R^5)$—, $A^2$ represents a nitrogen atom or =$C(R^5)$—, $R^1$ represents a C1-C4 alkyl group optionally substituted by at least one halogen atom, —$OR^6$, —$S(O)_m R^6$ (m represents 0, 1 or 2), $R^3$ represents a trifluoromethyl group, $R^4$ represents a hydrogen atom, $R^5$ represents a hydrogen atom, $R^6$ represents a C1-C4 alkyl group optionally substituted by at least one halogen atom;

Compounds of formula (1) in which $A^1$ represents =$C(R^5)$—, $A^2$ represents a nitrogen atom or =$C(R^5)$—, $R^1$ represents a —$OR^6$, —$S(O)_m R^6$ (m represents 0, 1 or 2) or halogen atom, $R^2$ represents a hydrogen atom, $R^3$ represents a trifluoromethyl group, $R^4$ represents a hydrogen atom, $R^5$ represents a hydrogen atom, $R^6$ represents a C1-C4 alkyl group optionally substituted by at least one halogen atom.

The method of producing the present compound will be described.

The present compound can be produced, for example, by the following (Production Method 1) to (Production Method 6).

(Production Method 1)

A compound (4) which is a compound represented by formula (1) in which n is 0 can be produced by reacting a compound (2) and a compound (3).

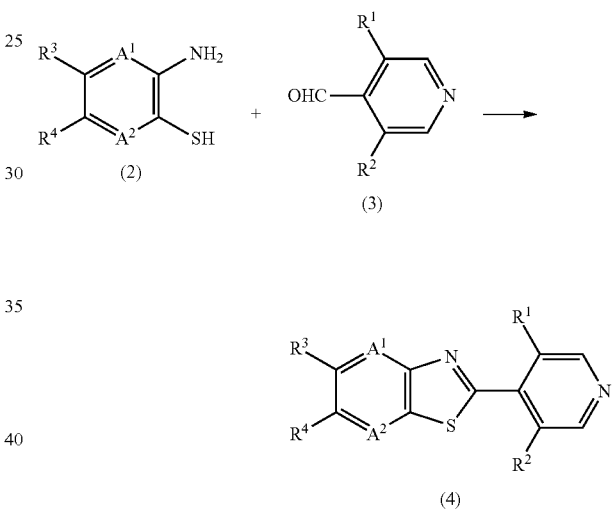

[wherein, $R^1$, $R^2$, $R^3$, $R^4$, $A^1$ and $A^2$ represent the same meanings as described above]

The reaction is carried out usually in the presence of a solvent.

Examples of the solvent to be used in the reaction include sulfoxides such as dimethyl sulfoxide (hereinafter, referred to as DMSO), aromatic hydrocarbons such as nitrobenzene, and mixtures thereof.

In the reaction, the compound (3) is used usually in a proportion of 0.5 to 3 mol with respect to 1 mol of the compound (2).

The reaction temperature of the reaction is usually in the range of 50 to 200° C. The reaction time of the reaction is usually in the range of 0.1 to 24 hours.

After completion of the reaction, water is added to the reaction mixture, then, the mixture is extracted with an organic solvent, and the organic layer is subjected to post treatment operations such as drying and concentration, thus, the compound (4) can be isolated. The isolated compound (4) can also be purified by chromatography, recrystallization and the like.

(Production Method 2)

A compound (4-b) which is a compound represented by formula (1) in which n represents 0 and $R^1$ represents —$OR^{6x}$ can be produced by reacting a compound (4-a) and a compound (5) in the presence of a base.

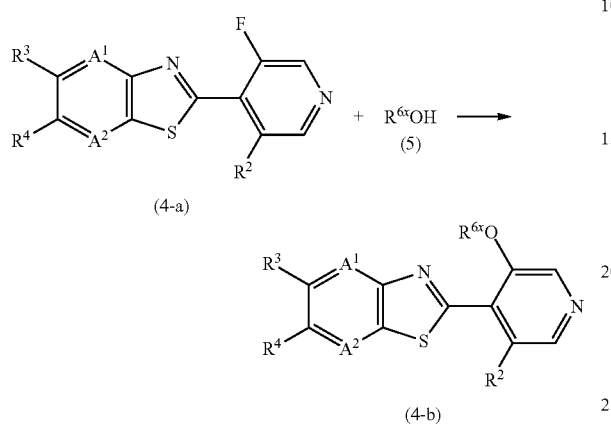

(Production Method 3)

A compound (4-c) which is a compound represented by formula (1) in which n represents 0 and $R^1$ represents —$SR^{6x}$ can be produced by reacting a compound (4-a) and a compound (6) in the presence of a base.

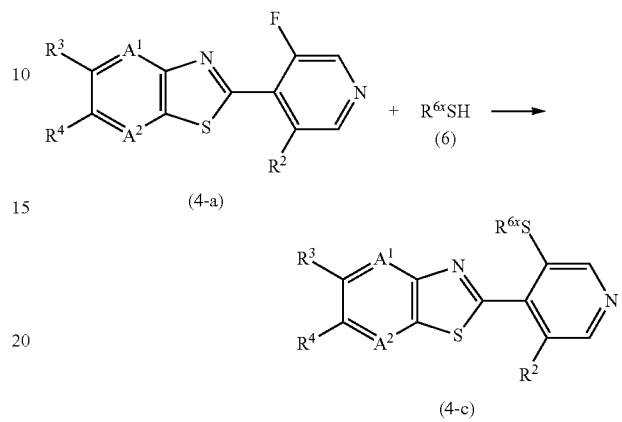

[wherein, $R^2$, $R^3$, $R^4$, $A^1$ and $A^2$ represent the same meanings as described above,
$R^{6x}$ represents a C1-C6 chain hydrocarbon group optionally substituted by at least one member selected from Group X, C4-C7 cycloalkylmethyl group optionally substituted by at least one member selected from Group X, C3-C6 alicyclic hydrocarbon group optionally substituted by at least one member selected from Group X, phenyl group optionally substituted by at least one member selected from Group Y, benzyl group optionally substituted by at least one member selected from Group Y, 5-membered heterocyclic group optionally substituted by at least one member selected from Group Y or 6-membered heterocyclic group optionally substituted by at least one member selected from Group Y]

The reaction can be carried out in the presence of a solvent. A solvent amount of the compound (5) is used in some cases.

Examples of the solvent to be used in the reaction include ethers such as tetrahydrofuran (hereinafter, referred to as THF), ethylene glycol dimethyl ether and 1,4-dioxane, aromatic hydrocarbons such as toluene and xylene, nitriles such as acetonitrile, acid amides such as N,N-dimethylformamide (hereinafter, referred to as DMF), sulfoxides such as DMSO, and mixtures thereof.

Examples of the base to be used in the reaction include alkali metal hydrides such as sodium hydride, and carbonates such as potassium carbonate, etc.

In the reaction, the compound (5) is used usually in a proportion of 1 to 100 mol with respect to 1 mol of the compound (4-a), and the base is used usually in a proportion of 1 to 10 mol with respect to 1 mol of the compound (4-a).

The reaction temperature of the reaction is usually in the range of 0 to 120° C., and the reaction time of the reaction is usually in the range of 0.5 to 24 hours.

After completion of the reaction, water is added to the reaction mixture, then, the mixture is extracted with an organic solvent, and the organic layer is subjected to post treatment operations such as drying and concentration, thus, the compound (4-b) can be isolated. The isolated compound (4-b) can also be purified by chromatography, recrystallization and the like.

[wherein, $R^2$, $R^3$, $R^4$, $R^{6x}$, $A^1$ and $A^2$ represent the same meanings as described above]

The reaction is carried out usually in the presence of a solvent.

Examples of the solvent to be used in the reaction include ethers such as THF, ethylene glycol dimethyl ether and 1,4-dioxane, aromatic hydrocarbons such as toluene and xylene, nitriles such as acetonitrile, acid amides such as DMF, sulfoxides such as DMSO, and mixtures thereof.

Examples of the base to be used in the reaction include alkali metal hydrides such as sodium hydride, and carbonates such as potassium carbonate.

In the reaction, the compound (6) is used usually in a proportion of 0.5 to 10 mol with respect to 1 mol of the compound (4-a), and the base is used usually in a proportion of 0.5 to 10 mol with respect to 1 mol of the compound (4-a).

The reaction temperature of the reaction is usually in the range of 0 to 100° C., and the reaction time of the reaction is usually in the range of 0.1 to 24 hours.

After completion of the reaction, water is added to the reaction mixture, then, the mixture is extracted with an organic solvent, and the organic layer is subjected to post treatment operations such as drying and concentration, thus, the compound (4-c) can be isolated. The isolated compound (4-c) can also be purified by chromatography, recrystallization and the like.

(Production Method 4)

A compound (4) which is a compound represented by formula (1) in which n represents 0 can be produced by reacting a hydrochloride of a compound (2) and a compound (3).

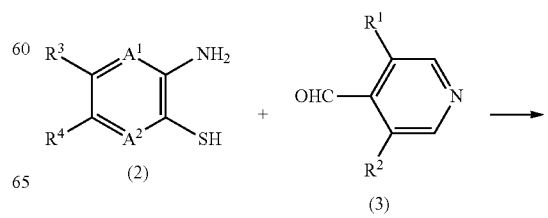

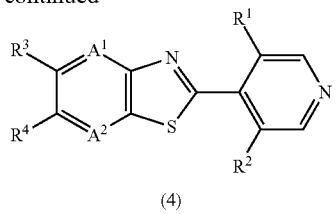

(4)

[wherein, $R^1$, $R^2$, $R^3$, $R^4$, $A^1$ and $A^2$ represent the same meanings as described above]

The reaction is carried out usually in the presence of a solvent, in the presence of a base.

Examples of the base to be used in the reaction include tertiary amines such as diisopropylethylamine and triethylamine.

Examples of the solvent to be used in the reaction include sulfoxides such as DMSO, aromatic hydrocarbons such as nitrobenzene, and mixtures thereof.

In the reaction, the compound (3) is used usually in a proportion of 0.5 to 3 mol with respect to 1 mol of the compound (2), and the base is used usually in a proportion of 1 to 2 mol with respect to 1 mol of the compound (2).

The reaction temperature of the reaction is usually in the range of 50 to 200° C., and the reaction time of the reaction is usually in the range of 0.1 to 24 hours.

After completion of the reaction, water is added to the reaction mixture, then, the mixture is extracted with an organic solvent, and the organic layer is subjected to post treatment operations such as drying and concentration, thus, the compound (4) can be isolated. The isolated compound (4) can also be purified by chromatography, recrystallization and the like.

(Production Method 5)

A compound (4-d) which is a compound represented by formula (1) in which n represents 0 and $A^1$ and $A^2$ represent =C($R^5$)— can be produced by subjecting a compound (7) to an oxidation reaction in the presence of a base.

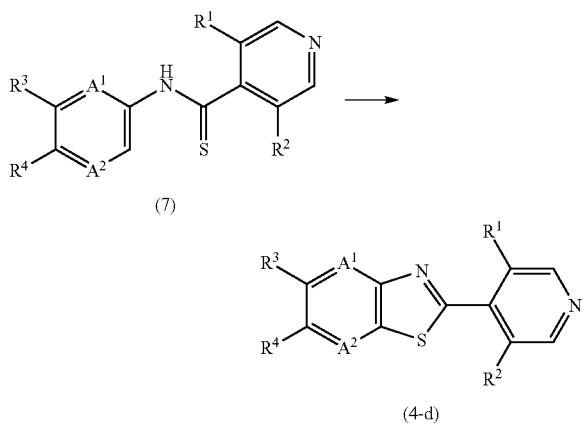

[wherein, $R^1$, $R^2$, $R^3$, $R^4$ and $R^5$ represent the same meanings as described above]

The reaction is carried out usually in the presence of a solvent.

Examples of the solvent to be used in the reaction include alcohols such as methanol and ethanol, water, and mixtures thereof.

Examples of the oxidizer to be used in the reaction include potassium ferricyanide.

The base to be used in the reaction includes alkali metal hydroxides such as sodium hydroxide.

In the reaction, the oxidizer is used usually in a proportion of 1 to 5 mol with respect to 1 mol of the compound (7).

The reaction temperature of the reaction is usually in the range of 0 to 100° C. The reaction time of the reaction is usually in the range of 0.1 to 24 hours.

After completion of the reaction, the reaction mixture is extracted with an organic solvent, and post treatment operations such as drying and concentration are carried out, thus, the compound (4-d) can be isolated. The isolated compound (4-d) can also be purified by chromatography, recrystallization and the like.

(Production Method 6)

A compound (8) which is a compound represented by formula (1) in which n represents 1 can be produced by subjecting a compound (4-e) to an oxidation reaction.

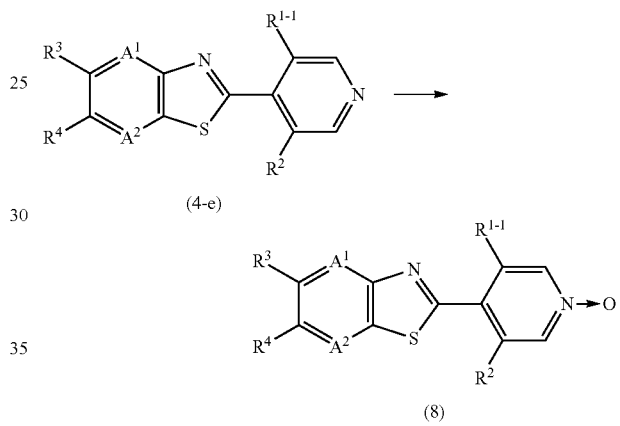

[wherein, $R^{1-1}$ represents a C1-C6 chain hydrocarbon group optionally substituted by at least one member selected from Group X, C3-C6 alicyclic hydrocarbon group optionally substituted by at least one member selected from Group X, phenyl group optionally substituted by at least one member selected from Group Y, 5-membered heterocyclic group optionally substituted by at least one member selected from Group Y, 6-membered heterocyclic group optionally substituted by at least one member selected from Group Y, —$OR^6$, —$NR^6R^7$, —$NR^6C(O)R^8$, —$NR^6CO_2R^9$, —$C(O)R^{10}$, —$C(NOR^6)R^{10}$, cyano group, nitro group or halogen atom, $R^2$, $R^3$, $R^4$, $A^1$ and $A^2$ represent the same meanings as described above]

The reaction is carried out usually in the presence of a solvent.

Examples of the solvent to be used in the reaction include aliphatic halogenated hydrocarbons such as dichloromethane and chloroform, acetic acid, water, and mixtures thereof.

Examples of the oxidizer to be used in the reaction include peroxy acids such as 3-chloroperbenzoic acid, hydrogen peroxide solution.

In the reaction, the oxidizer is used usually in a proportion of 1 to 3 mol with respect to 1 mol of the compound (4-e).

The reaction temperature of the reaction is usually in the range of −20 to 100° C. The reaction time of the reaction is usually in the range of 0.1 to 24 hours.

After completion of the reaction, water is added to the reaction mixture, then, the reaction mixture is extracted with an organic solvent, and the organic layer is, if necessary, washed with an aqueous solution of a reducing agent and an aqueous solution of a base, and subjected to post treatment operations such as drying and concentration, thus, the compound (8) can be isolated. The isolated compound (8) can also be purified by chromatography, recrystallization and the like.

An intermediate in the present invention can be produced, for example, by the following method.
(Intermediate Production Method 1)

A compound (2) can be produced, for example, by the following method.

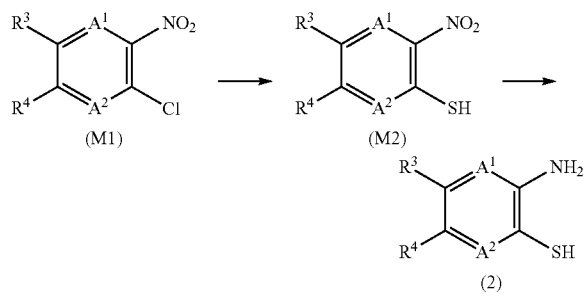

[wherein, $R^3$, $R^4$, $A^1$ and $A^2$ represent the same meanings as described above]
(Step 1)

A compound (M2) can be produced by reacting a compound (M1) and thiourea in the presence of a base.

The reaction is carried out usually in the presence of a solvent.

Examples of the solvent to be used in the reaction include alcohols such as methanol and ethanol, water, and mixtures thereof.

Examples of the base to be used in the reaction include alkali metal hydroxides such as sodium hydroxide and potassium hydroxide.

In the reaction, thiourea is used usually in a proportion of 0.5 to 3 mol with respect to 1 mol of the compound (M1), and the base is used usually in a proportion of 1 to 10 mol with respect to 1 mol of the compound (M1).

The reaction temperature of the reaction is usually in the range of 0 to 100° C. The reaction time of the reaction is usually in the range of 0.1 to 24 hours.

After completion of the reaction, an acid is added to the reaction mixture, then, the mixture is extracted with an organic solvent, and the organic layer is subjected to post treatment operations such as drying and concentration, thus, the compound (M2) can be isolated. The isolated compound (M2) can also be purified by chromatography, recrystallization and the like.
(Step 2)

The compound (2) can be produced by subjecting the compound (M2) to a reducing reaction.

The reducing reaction can be carried out in the presence of, for example, a metal powder such as an iron powder and zinc powder; an acid such as hydrochloric acid and acetic acid; and water.

The reaction is carried out usually in the presence of a solvent.

Examples of the solvent to be used in the reaction include ethers such as THF, ethylene glycol dimethyl ether and 1,4-dioxane, esters such as ethyl acetate and butyl acetate, alcohols such as methanol and ethanol, acid amides such as DMF, and mixtures thereof.

The above-described reducing agent includes an iron powder, zinc powder, stannous chloride and the like.

In the reaction, a metal powder is used usually in a proportion of 3 to 10 mol with respect to 1 mol of the compound (M2).

The reaction temperature of the reaction is usually in the range of 0 to 100° C. The reaction time of the reaction is usually in the range of 0.1 to 24 hours.

After completion of the reaction, water is added to the reaction mixture, then, the mixture is extracted with an organic solvent, and the organic layer is subjected to post treatment operations such as drying and concentration, thus, the compound (2) can be isolated. The isolated compound (2) can also be purified by chromatography, recrystallization and the like.

Next, specific examples of the present compound are shown below.

In the table described below, Me represents a methyl group, Et represents an ethyl group, Pr represents a propyl group, iPr represents an isopropyl group, cPr represents a cyclopropyl group, tBu represents a tert-butyl group, cPen represents a cyclopentyl group, Ph represents a phenyl group, 2-Py represents a 2-pyridyl group, 3-Py represents a 3-pyridyl group, 4-Py represents a 4-pyridyl group, 1-Tz represents a 1,2,4-triazol-1-yl group, 1-Pz represents a pyrazol-1-yl group.

Compounds represented by formula (1)

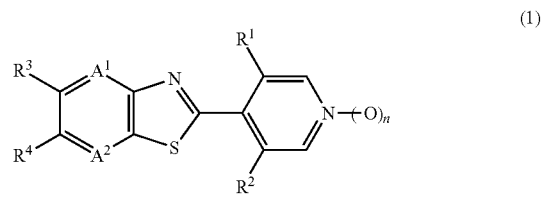

In the above-described formula (1), substituents $R^1$, $R^2$, $R^3$, $R^4$, $A^1$, $A^2$ and n are combined as described in (Table 1) to (Table 38).

TABLE 1

| $R^1$ | $R^2$ | $R^3$ | $R^4$ | $A^1$ | $A^2$ | n |
|---|---|---|---|---|---|---|
| F | H | $CF_3$ | H | =C(H)— | =C(H)— | 0 |
| Cl | H | $CF_3$ | H | =C(H)— | =C(H)— | 0 |
| Br | H | $CF_3$ | H | =C(H)— | =C(H)— | 0 |
| I | H | $CF_3$ | H | =C(H)— | =C(H)— | 0 |
| Me | H | $CF_3$ | H | =C(H)— | =C(H)— | 0 |
| Et | H | $CF_3$ | H | =C(H)— | =C(H)— | 0 |
| Pr | H | $CF_3$ | H | =C(H)— | =C(H)— | 0 |
| cPr | H | $CF_3$ | H | =C(H)— | =C(H)— | 0 |
| $CF_3$ | H | $CF_3$ | H | =C(H)— | =C(H)— | 0 |
| $CH_3OCH_2$ | H | $CF_3$ | H | =C(H)— | =C(H)— | 0 |
| MeO | H | $CF_3$ | H | =C(H)— | =C(H)— | 0 |
| EtO | H | $CF_3$ | H | =C(H)— | =C(H)— | 0 |
| PrO | H | $CF_3$ | H | =C(H)— | =C(H)— | 0 |
| $CF_3CH_2O$ | H | $CF_3$ | H | =C(H)— | =C(H)— | 0 |
| $CHF_2CH_2O$ | H | $CF_3$ | H | =C(H)— | =C(H)— | 0 |
| iPrO | H | $CF_3$ | H | =C(H)— | =C(H)— | 0 |
| $cPrCH_2O$ | H | $CF_3$ | H | =C(H)— | =C(H)— | 0 |
| cPenO | H | $CF_3$ | H | =C(H)— | =C(H)— | 0 |
| MeS | H | $CF_3$ | H | =C(H)— | =C(H)— | 0 |
| MeS(O) | H | $CF_3$ | H | =C(H)— | =C(H)— | 0 |
| $MeS(O)_2$ | H | $CF_3$ | H | =C(H)— | =C(H)— | 0 |
| EtS | H | $CF_3$ | H | =C(H)— | =C(H)— | 0 |
| EtS(O) | H | $CF_3$ | H | =C(H)— | =C(H)— | 0 |
| $EtS(O)_2$ | H | $CF_3$ | H | =C(H)— | =C(H)— | 0 |

TABLE 2

| R¹ | R² | R³ | R⁴ | A¹ | A² | n |
|---|---|---|---|---|---|---|
| PrS | H | CF₃ | H | =C(H)— | =C(H)— | 0 |
| PrS(O) | H | CF₃ | H | =C(H)— | =C(H)— | 0 |
| PrS(O)₂ | H | CF₃ | H | =C(H)— | =C(H)— | 0 |
| iPrS | H | CF₃ | H | =C(H)— | =C(H)— | 0 |
| iPrS(O) | H | CF₃ | H | =C(H)— | =C(H)— | 0 |
| iPrS(O)₂ | H | CF₃ | H | =C(H)— | =C(H)— | 0 |
| CF₃CH₂S | H | CF₃ | H | =C(H)— | =C(H)— | 0 |
| CHF₂CH₂S | H | CF₃ | H | =C(H)— | =C(H)— | 0 |
| MeHN | H | CF₃ | H | =C(H)— | =C(H)— | 0 |
| Me₂N | H | CF₃ | H | =C(H)— | =C(H)— | 0 |
| Me(iPr)N | H | CF₃ | H | =C(H)— | =C(H)— | 0 |
| CH₃C(O)NH | H | CF₃ | H | =C(H)— | =C(H)— | 0 |
| MeOC(O)NH | H | CF₃ | H | =C(H)— | =C(H)— | 0 |
| HC(O) | H | CF₃ | H | =C(H)— | =C(H)— | 0 |
| CH₃C(O) | H | CF₃ | H | =C(H)— | =C(H)— | 0 |
| HC(NOMe) | H | CF₃ | H | =C(H)— | =C(H)— | 0 |
| CH₃C(NOMe) | H | CF₃ | H | =C(H)— | =C(H)— | 0 |
| Ph | H | CF₃ | H | =C(H)— | =C(H)— | 0 |
| 2-Py | H | CF₃ | H | =C(H)— | =C(H)— | 0 |
| 3-Py | H | CF₃ | H | =C(H)— | =C(H)— | 0 |
| 4-Py | H | CF₃ | H | =C(H)— | =C(H)— | 0 |
| 1-Tz | H | CF₃ | H | =C(H)— | =C(H)— | 0 |
| 1-Pz | H | CF₃ | H | =C(H)— | =C(H)— | 0 |
| F | H | CF₃ | H | =C(H)— | =C(H)— | 1 |

TABLE 3

| R¹ | R² | R³ | R⁴ | A¹ | A² | n |
|---|---|---|---|---|---|---|
| Cl | H | CF₃ | H | =C(H)— | =C(H)— | 1 |
| Br | H | CF₃ | H | =C(H)— | =C(H)— | 1 |
| I | H | CF₃ | H | =C(H)— | =C(H)— | 1 |
| Me | H | CF₃ | H | =C(H)— | =C(H)— | 1 |
| Et | H | CF₃ | H | =C(H)— | =C(H)— | 1 |
| Pr | H | CF₃ | H | =C(H)— | =C(H)— | 1 |
| cPr | H | CF₃ | H | =C(H)— | =C(H)— | 1 |
| CF₃ | H | CF₃ | H | =C(H)— | =C(H)— | 1 |
| CH₃OCH₂ | H | CF₃ | H | =C(H)— | =C(H)— | 1 |
| MeO | H | CF₃ | H | =C(H)— | =C(H)— | 1 |
| EtO | H | CF₃ | H | =C(H)— | =C(H)— | 1 |
| PrO | H | CF₃ | H | =C(H)— | =C(H)— | 1 |
| CF₃CH₂O | H | CF₃ | H | =C(H)— | =C(H)— | 1 |
| CHF₂CH₂O | H | CF₃ | H | =C(H)— | =C(H)— | 1 |
| iPrO | H | CF₃ | H | =C(H)— | =C(H)— | 1 |
| Ph | H | CF₃ | H | =C(H)— | =C(H)— | 1 |
| F | H | CF₃ | Cl | =C(H)— | =C(H)— | 0 |
| Cl | H | CF₃ | Cl | =C(H)— | =C(H)— | 0 |
| Br | H | CF₃ | Cl | =C(H)— | =C(H)— | 0 |
| I | H | CF₃ | Cl | =C(H)— | =C(H)— | 0 |
| Me | H | CF₃ | Cl | =C(H)— | =C(H)— | 0 |
| Et | H | CF₃ | Cl | =C(H)— | =C(H)— | 0 |
| Pr | H | CF₃ | Cl | =C(H)— | =C(H)— | 0 |
| CF₃ | H | CF₃ | Cl | =C(H)— | =C(H)— | 0 |

TABLE 4

| R¹ | R² | R³ | R⁴ | A¹ | A² | n |
|---|---|---|---|---|---|---|
| CH₃OCH₂ | H | CF₃ | Cl | =C(H)— | =C(H)— | 0 |
| MeO | H | CF₃ | Cl | =C(H)— | =C(H)— | 0 |
| EtO | H | CF₃ | Cl | =C(H)— | =C(H)— | 0 |
| PrO | H | CF₃ | Cl | =C(H)— | =C(H)— | 0 |
| CF₃CH₂O | H | CF₃ | Cl | =C(H)— | =C(H)— | 0 |
| CHF₂CH₂O | H | CF₃ | Cl | =C(H)— | =C(H)— | 0 |
| iPrO | H | CF₃ | Cl | =C(H)— | =C(H)— | 0 |
| MeS | H | CF₃ | Cl | =C(H)— | =C(H)— | 0 |
| MeS(O) | H | CF₃ | Cl | =C(H)— | =C(H)— | 0 |
| MeS(O)₂ | H | CF₃ | Cl | =C(H)— | =C(H)— | 0 |
| EtS | H | CF₃ | Cl | =C(H)— | =C(H)— | 0 |
| EtS(O) | H | CF₃ | Cl | =C(H)— | =C(H)— | 0 |
| EtS(O)₂ | H | CF₃ | Cl | =C(H)— | =C(H)— | 0 |
| PrS | H | CF₃ | Cl | =C(H)— | =C(H)— | 0 |
| PrS(O) | H | CF₃ | Cl | =C(H)— | =C(H)— | 0 |

TABLE 4-continued

| R¹ | R² | R³ | R⁴ | A¹ | A² | n |
|---|---|---|---|---|---|---|
| PrS(O)₂ | H | CF₃ | ClCl | =C(H)— | =C(H)— | 0 |
| iPrS | H | CF₃ | Cl | =C(H)— | =C(H)— | 0 |
| iPrS(O) | H | CF₃ | Cl | =C(H)— | =C(H)— | 0 |
| iPrS(O)₂ | H | CF₃ | Cl | =C(H)— | =C(H)— | 0 |
| CF₃CH₂S | H | CF₃ | Cl | =C(H)— | =C(H)— | 0 |
| CHF₂CH₂S | H | CF₃ | H | =C(H)— | =C(H)— | 0 |
| F | H | CF₃ | H | =C(H)— | =C(Cl)— | 0 |
| Cl | H | CF₃ | H | =C(H)— | =C(Cl)— | 0 |
| Br | H | CF₃ |  | =C(H)— | =C(Cl)— | 0 |

TABLE 5

| R¹ | R² | R³ | R⁴ | A¹ | A² | n |
|---|---|---|---|---|---|---|
| I | H | CF₃ | H | =C(H)— | =C(Cl)— | 0 |
| Me | H | CF₃ | H | =C(H)— | =C(Cl)— | 0 |
| Et | H | CF₃ | H | =C(H)— | =C(Cl)— | 0 |
| Pr | H | CF₃ | H | =C(H)— | =C(Cl)— | 0 |
| CF₃ | H | CF₃ | H | =C(H)— | =C(Cl)— | 0 |
| CH₃OCH₂ | H | CF₃ | H | =C(H)— | =C(Cl)— | 0 |
| MeO | H | CF₃ | H | =C(H)— | =C(Cl)— | 0 |
| EtO | H | CF₃ | H | =C(H)— | =C(Cl)— | 0 |
| PrO | H | CF₃ | H | =C(H)— | =C(Cl)— | 0 |
| CF₃CH₂O | H | CF₃ | H | =C(H)— | =C(Cl)— | 0 |
| CHF₂CH₂O | H | CF₃ | H | =C(H)— | =C(Cl)— | 0 |
| iPrO | H | CF₃ | H | =C(H)— | =C(Cl)— | 0 |
| MeS | H | CF₃ | H | =C(H)— | =C(Cl)— | 0 |
| MeS(O) | H | CF₃ | H | =C(H)— | =C(Cl)— | 0 |
| MeS(O)₂ | H | CF₃ | H | =C(H)— | =C(Cl)— | 0 |
| EtS | H | CF₃ | H | =C(H)— | =C(Cl)— | 0 |
| EtS(O) | H | CF₃ | H | =C(H)— | =C(Cl)— | 0 |
| EtS(O)₂ | H | CF₃ | H | =C(H)— | =C(Cl)— | 0 |
| PrS | H | CF₃ | H | =C(H)— | =C(Cl)— | 0 |
| PrS(O) | H | CF₃ | H | =C(H)— | =C(Cl)— | 0 |
| PrS(O)₂ | H | CF₃ | H | =C(H)— | =C(Cl)— | 0 |
| iPrS | H | CF₃ | H | =C(H)— | =C(Cl)— | 0 |
| iPrS(O) | H | CF₃ | H | =C(H)— | =C(Cl)— | 0 |
| iPrS(O)₂ | H | CF₃ | H | =C(H)— | =C(Cl)— | 0 |

TABLE 6

| R¹ | R² | R³ | R⁴ | A¹ | A² | n |
|---|---|---|---|---|---|---|
| CF₃CH₂S | H | CF₃ | H | =C(H)— | =C(Cl)— | 0 |
| CHF₂CH₂S | H | CF₃ | H | =C(H)— | =C(Cl)— | 0 |
| Cl | Cl | CF₃ | H | =C(H)— | =C(H)— | 0 |
| MeO | Cl | CF₃ | H | =C(H)— | =C(H)— | 0 |
| EtO | Cl | CF₃ | H | =C(H)— | =C(H)— | 0 |
| PrO | Cl | CF₃ | H | =C(H)— | =C(H)— | 0 |
| CF₃CH₂O | Cl | CF₃ | H | =C(H)— | =C(H)— | 0 |
| CHF₂CH₂O | Cl | CF₃ | H | =C(H)— | =C(H)— | 0 |
| iPrO | Cl | CF₃ | H | =C(H)— | =C(H)— | 0 |
| MeS | Cl | CF₃ | H | =C(H)— | =C(H)— | 0 |
| MeS(O) | Cl | CF₃ | H | =C(H)— | =C(H)— | 0 |
| MeS(O)₂ | Cl | CF₃ | H | =C(H)— | =C(H)— | 0 |
| EtS | Cl | CF₃ | H | =C(H)— | =C(H)— | 0 |
| EtS(O) | Cl | CF₃ | H | =C(H)— | =C(H)— | 0 |
| EtS(O)₂ | Cl | CF₃ | H | =C(H)— | =C(H)— | 0 |
| CF₃CH₂S | Cl | CF₃ | H | =C(H)— | =C(H)— | 0 |
| CHF₂CH₂S | Cl | CF₃ | H | =C(H)— | =C(H)— | 0 |
| MeHN | Cl | CF₃ | H | =C(H)— | =C(H)— | 0 |
| Me₂N | Cl | CF₃ | H | =C(H)— | =C(H)— | 0 |
| Me(iPr)N | Cl | CF₃ | H | =C(H)— | =C(H)— | 0 |
| Cl | F | CF₃ | H | =C(H)— | =C(H)— | 0 |
| MeO | F | CF₃ | H | =C(H)— | =C(H)— | 0 |
| Eta | F | CF₃ | H | =C(H)— | =C(H)— | 0 |
| PrO | F | CF₃ | H | =C(H)— | =C(H)— | 0 |

TABLE 7

| R¹ | R² | R³ | R⁴ | A¹ | A² | n |
|---|---|---|---|---|---|---|
| CF₃CH₂O | F | CF₃ | H | =C(H)— | =C(H)— | 0 |
| CHF₂CH₂O | F | CF₃ | H | =C(H)— | =C(H)— | 0 |
| iPrO | F | CF₃ | H | =C(H)— | =C(H)— | 0 |
| MeS | F | CF₃ | H | =C(H)— | =C(H)— | 0 |
| MeS(O) | F | CF₃ | H | =C(H)— | =C(H)— | 0 |
| MeS(O)₂ | F | CF₃ | H | =C(H)— | =C(H)— | 0 |
| EtS | F | CF₃ | H | =C(H)— | =C(H)— | 0 |
| EtS(O) | F | CF₃ | H | =C(H)— | =C(H)— | 0 |
| EtS(O)₂ | F | CF₃ | H | =C(H)— | =C(H)— | 0 |
| CF₃CH₂S | F | CF₃ | H | =C(H)— | =C(H)— | 0 |
| CHF₂CH₂S | F | CF₃ | H | =C(H)— | =C(H)— | 0 |
| MeHN | F | CF₃ | H | =C(H)— | =C(H)— | 0 |
| Me₂N | F | CF₃ | H | =C(H)— | =C(H)— | 0 |
| Me(iPr)N | F | CF₃ | H | =C(H)— | =C(H)— | 0 |
| F | H | CF₃O | H | =C(H)— | =C(H)— | 0 |
| Cl | H | CF₃O | H | =C(H)— | =C(H)— | 0 |
| Br | H | CF₃O | H | =C(H)— | =C(H)— | 0 |
| I | H | CF₃O | H | =C(H)— | =C(H)— | 0 |
| Me | H | CF₃O | H | =C(H)— | =C(H)— | 0 |
| Et | H | CF₃O | H | =C(H)— | =C(H)— | 0 |
| Pr | H | CF₃O | H | =C(H)— | =C(H)— | 0 |
| cPr | H | CF₃O | H | =C(H)— | =C(H)— | 0 |
| CF₃ | H | CF₃O | H | =C(H)— | =C(H)— | 0 |
| CH₃OCH₂ | H | CF₃O | H | =C(H)— | =C(H)— | 0 |

TABLE 8

| R¹ | R² | R³ | R⁴ | A¹ | A² | n |
|---|---|---|---|---|---|---|
| MeO | H | CF₃O | H | =C(H)— | =C(H)— | 0 |
| EtO | H | CF₃O | H | =C(H)— | =C(H)— | 0 |
| PrO | H | CF₃O | H | =C(H)— | =C(H)— | 0 |
| CF₃CH₂O | H | CF₃O | H | =C(H)— | =C(H)— | 0 |
| CHF₂CH₂O | H | CF₃O | H | =C(H)— | =C(H)— | 0 |
| iPrO | H | CF₃O | H | =C(H)— | =C(H)— | 0 |
| cPrCH₂O | H | CF₃O | H | =C(H)— | =C(H)— | 0 |
| cPenO | H | CF₃O | H | =C(H)— | =C(H)— | 0 |
| MeS | H | CF₃O | H | =C(H)— | =C(H)— | 0 |
| MeS(O) | H | CF₃O | H | =C(H)— | =C(H)— | 0 |
| MeS(O)₂ | H | CF₃O | H. | =C(H)— | =C(H)— | 0 |
| EtS | H | CF₃O | H | =C(H)— | =C(H)— | 0 |
| EtS(O) | H | CF₃O | H | =C(H)— | =C(H)— | 0 |
| EtS(O)₂ | H | CF₃O | H | =C(H)— | =C(H)— | 0 |
| PrS | H | CF₃O | H | =C(H)— | =C(H)— | 0 |
| PrS(O) | H | CF₃O | H | =C(H)— | =C(H)— | 0 |
| PrS(O)₂ | H | CF₃O | H | =C(H)— | =C(H)— | 0 |
| iPrS | H | CF₃O | H | =C(H)— | =C(H)— | 0 |
| iPrS(O) | H | CF₃O | H | =C(H)— | =C(H)— | 0 |
| iPrS(O)₂ | H | CF₃O | H | =C(H)— | =C(H)— | 0 |
| CF₃CH₂S | H | CF₃O | H | =C(H)— | =C(H)— | 0 |
| CHF₂CH₂S | H | CF₃O | H | =C(H)— | =C(H)— | 0 |
| MeHN | H | CF₃O | H | =C(H)— | =C(H)— | 0 |
| Me₂N | H | CF₃O | H | =C(H)— | =C(H)— | 0 |

TABLE 9

| R¹ | R² | R³ | R⁴ | A¹ | A² | n |
|---|---|---|---|---|---|---|
| Me(iPr)N | H | CF₃O | H | =C(H)— | =C(H)— | 0 |
| CH₃C(O)NH | H | CF₃O | H | =C(H)— | =C(H)— | 0 |
| MeOC(O)NH | H | CF₃O | H | =C(H)— | =C(H)— | 0 |
| HC(O) | H | CF₃O | H | =C(H)— | =C(H)— | 0 |
| CH₃C(O) | H | CF₃O | H | =C(H)— | =C(H)— | 0 |
| HC(NOMe) | H | CF₃O | H | =C(H)— | =C(H)— | 0 |
| CH₃C(NOMe) | H | CF₃O | H | =C(H)— | =C(H)— | 0 |
| Ph | H | CF₃O | H | =C(H)— | =C(H)— | 0 |
| 2-Py | H | CF₃O | H | =C(H)— | =C(H)— | 0 |
| 3-Py | H | CF₃O | H | =C(H)— | =C(H)— | 0 |
| 4-Py | H | CF₃O | H | =C(H)— | =C(H)— | 0 |
| 1-Tz | H | CF₃O | H | =C(H)— | =C(H)— | 0 |
| 1-Pz | H | CF₃O | H | =C(H)— | =C(H)— | 0 |
| F | H | CF₃O | H | =C(H)— | =C(H)— | 1 |
| Cl | H | CF₃O | H | =C(H)— | =C(H)— | 1 |
| Br | H | CF₃O | H | =C(H)— | =C(H)— | 1 |
| I | H | CF₃O | H | =C(H)— | =C(H)— | 1 |
| Me | H | CF₃O | H | =C(H)— | =C(H)— | 1 |
| Et | H | CF₃O | H | =C(H)— | =C(H)— | 1 |
| Pr | H | CF₃O | H | =C(H)— | =C(H)— | 1 |
| cPr | H | CF₃O | H | =C(H)— | =C(H)— | 1 |
| CF₃ | H | CF₃O | H | =C(H)— | =C(H)— | 1 |
| CH₃OCH₂ | H | CF₃O | H | =C(H)— | =C(H)— | 1 |
| MeO | H | CF₃O | H | =C(H)— | =C(H)— | 1 |

TABLE 10

| R¹ | R² | R³ | R⁴ | A¹ | A² | n |
|---|---|---|---|---|---|---|
| EtO | H | CF₃O | H | =C(H)— | =C(H)— | 1 |
| PrO | H | CF₃O | H | =C(H)— | =C(H)— | 1 |
| CF₃CH₂O | H | CF₃O | H | =C(H)— | =C(H)— | 1 |
| CHF₂CH₂O | H | CF₃O | H | =C(H)— | =C(H)— | 1 |
| iPrO | H | CF₃O | H | =C(H)— | =C(H)— | 1 |
| Ph | H | CF₃O | H | =C(H)— | =C(H)— | 1 |
| F | H | CF₃S | H | =C(H)— | =C(H)— | 0 |
| Cl | H | CF₃S | H | =C(H)— | =C(H)— | 0 |
| Br | H | CF₃S | H | =C(H)— | =C(H)— | 0 |
| I | H | CF₃S | H | =C(H)— | =C(H)— | 0 |
| Me | H | CF₃S | H | =C(H)— | =C(H)— | 0 |
| Et | H | CF₃S | H | =C(H)— | =C(H)— | 0 |
| Pr | H | CF₃S | H | =C(H)— | =C(H)— | 0 |
| cPr | H | CF₃S | H | =C(H)— | =C(H)— | 0 |
| CF₃ | H | CF₃S | H | =C(H)— | =C(H)— | 0 |
| CH₃OCH₂ | H | CF₃S | H | =C(H)— | =C(H)— | 0 |
| MeO | H | CF₃S | H | =C(H)— | =C(H)— | 0 |
| EtO | H | CF₃S | H | =C(H)— | =C(H)— | 0 |
| PrO | H | CF₃S | H | =C(H)— | =C(H)— | 0 |
| CF₃CH₂O | H | CF₃S | H | =C(H)— | =C(H)— | 0 |
| CHF₂CH₂O | H | CF₃S | H | =C(H)— | =C(H)— | 0 |
| iPrO | H | CF₃S | H | =C(H)— | =C(H)— | 0 |
| cPrCH₂O | H | CF₃S | H | =C(H)— | =C(H)— | 0 |
| cPenO | H | CF₃S | H | =C(H)— | =C(H)— | 0 |

TABLE 11

| R¹ | R² | R³ | R⁴ | A¹ | A² | n |
|---|---|---|---|---|---|---|
| MeS | H | CF₃S | H | =C(H)— | =C(H)— | 0 |
| MeS(O) | H | CF₃S | H | =C(H)— | =C(H)— | 0 |
| MeS(O)₂ | H | CF₃S | H | =C(H)— | =C(H)— | 0 |
| EtS | H | CF₃S | H | =C(H)— | =C(H)— | 0 |
| EtS(O) | H | CF₃S | H | =C(H)— | =C(H)— | 0 |
| EtS(O)₂ | H | CF₃S | H | =C(H)— | =C(H)— | 0 |
| PrS | H | CF₃S | H | =C(H)— | =C(H)— | 0 |
| PrS(O) | H | CF₃S | H | =C(H)— | =C(H)— | 0 |
| PrS(O)₂ | H | CF₃S | H | =C(H)— | =C(H)— | 0 |
| iPrS | H | CF₃S | H | =C(H)— | =C(H)— | 0 |
| iPrS(O) | H | CF₃S | H | =C(H)— | =C(H)— | 0 |
| iPrS(O)₂ | H | CF₃S | H | =C(H)— | =C(H)— | 0 |
| CF₃CH₂S | H | CF₃S | H | =C(H)— | =C(H)— | 0 |
| CHF₂CH₂S | H | CF₃S | H | =C(H)— | =C(H)— | 0 |
| MeHN | H | CF₃S | H | =C(H)— | =C(H)— | 0 |
| Me₂N | H | CF₃S | H | =C(H)— | =C(H)— | 0 |
| Me(iPr)N | H | CF₃S | H | =C(H)— | =C(H)— | 0 |
| CH₃C(O)NH | H | CF₃S | H | =C(H)— | =C(H)— | 0 |
| MeOC(O)NH | H | CF₃S | H | =C(H)— | =C(H)— | 0 |
| HC(O) | H | CF₃S | H | =C(H)— | =C(H)— | 0 |
| CH₃C(O) | H | CF₃S | H | =C(H)— | =C(H)— | 0 |
| HC(NOMe) | H | CF₃S | H | =C(H)— | =C(H)— | 0 |
| CH₃C(NOMe) | H | CF₃S | H | =C(H)— | =C(H)— | 0 |
| Ph | H | CF₃S | H | =C(H)— | =C(H)— | 0 |

TABLE 12

| R¹ | R² | R³ | R⁴ | A¹ | A² | n |
|---|---|---|---|---|---|---|
| 2-Py | H | CF₃S | H | =C(H)— | =C(H)— | 0 |
| 3-Py | H | CF₃S | H | =C(H)— | =C(H)— | 0 |
| 4-Py | H | CF₃S | H | =C(H)— | =C(H)— | 0 |
| 1-Tz | H | CF₃S | H | =C(H)— | =C(H)— | 0 |
| 1-Pz | H | CF₃S | H | =C(H)— | =C(H)— | 0 |
| F | H | CF₃CF₂ | H | =C(H)— | =C(H)— | 0 |
| Cl | H | CF₃CF₂ | H | =C(H)— | =C(H)— | 0 |
| Br | H | CF₃CF₂ | H | =C(H)— | =C(H)— | 0 |
| I | H | CF₃CF₂ | H | =C(H)— | =C(H)— | 0 |
| Me | H | CF₃CF₂ | H | =C(H)— | =C(H)— | 0 |
| Et | H | CF₃CF₂ | H | =C(H)— | =C(H)— | 0 |
| Pr | H | CF₃CF₂ | H | =C(H)— | =C(H)— | 0 |
| cPr | H | CF₃CF₂ | H | =C(H)— | =C(H)— | 0 |
| CF₃ | H | CF₃CF₂ | H | =C(H)— | =C(H)— | 0 |
| CH₃OCH₂ | H | CF₃CF₂ | H | =C(H)— | =C(H)— | 0 |
| MeO | H | CF₃CF₂ | H | =C(H)— | =C(H)— | 0 |
| EtO | H | CF₃CF₂ | H | =C(H)— | =C(H)— | 0 |
| PrO | H | CF₃CF₂ | H | =C(H)— | =C(H)— | 0 |
| CF₃CH₂O | H | CF₃CF₂ | H | =C(H)— | =C(H)— | 0 |
| CHF₂CH₂O | H | CF₃CF₂ | H | =C(H)— | =C(H)— | 0 |
| iPrO | H | CF₃CF₂ | H | =C(H)— | =C(H)— | 0 |
| cPrCH₂O | H | CF₃CF₂ | H | =C(H)— | =C(H)— | 0 |
| cPenO | H | CF₃CF₂ | H | =C(H)— | =C(H)— | 0 |
| MeS | H | CF₃CF₂ | H | =C(H)— | =C(H)— | 0 |

TABLE 13

| R¹ | R² | R³ | R⁴ | A¹ | A² | n |
|---|---|---|---|---|---|---|
| MeS(O) | H | CF₃CF₂ | H | =C(H)— | =C(H)— | 0 |
| MeS(O)₂ | H | CF₃CF₂ | H | =C(H)— | =C(H)— | 0 |
| EtS | H | CF₃CF₂ | H | =C(H)— | =C(H)— | 0 |
| EtS(O) | H | CF₃CF₂ | H | =C(H)— | =C(H)— | 0 |
| EtS(O)₂ | H | CF₃CF₂ | H | =C(H)— | =C(H)— | 0 |
| PrS | H | CF₃CF₂ | H | =C(H)— | =C(H)— | 0 |
| PrS(O) | H | CF₃CF₂ | H | =C(H)— | =C(H)— | 0 |
| PrS(O)₂ | H | CF₃CF₂ | H | =C(H)— | =C(H)— | 0 |
| iPrS | H | CF₃CF₂ | H | =C(H)— | =C(H)— | 0 |
| iPrS(O) | H | CF₃CF₂ | H | =C(H)— | =C(H)— | 0 |
| iPrS(O)₂ | H | CF₃CF₂ | H | =C(H)— | =C(H)— | 0 |
| CF₃CH₂S | H | CF₃CF₂ | H | =C(H)— | =C(H)— | 0 |
| CHF₂CH₂S | H | CF₃CF₂ | H | =C(H)— | =C(H)— | 0 |
| MeHN | H | CF₃CF₂ | H | =C(H)— | =C(H)— | 0 |
| Me₂N | H | CF₃CF₂ | H | =C(H)— | =C(H)— | 0 |
| Me(iPr)N | H | CF₃CF₂ | H | =C(H)— | =C(H)— | 0 |
| Ph | H | CF₃CF₂ | H | =C(H)— | =C(H)— | 0 |
| 2-Py | H | CF₃CF₂ | H | =C(H)— | =C(H)— | 0 |
| 3-Py | H | CF₃CF₂ | H | =C(H)— | =C(H)— | 0 |
| 4-Py | H | CF₃CF₂ | H | =C(H)— | =C(H)— | 0 |
| 1-Tz | H | CF₃CF₂ | H | =C(H)— | =C(H)— | 0 |
| 1-Pz | H | CF₃CF₂ | H | =C(H)— | =C(H)— | 0 |
| F | H | (CF₃)₂CF | H | =C(H)— | =C(H)— | 0 |
| Cl | H | (CF₃)₂CF | H | =C(H)— | =C(H)— | 0 |

TABLE 14

| R¹ | R² | R³ | R⁴ | A¹ | A² | n |
|---|---|---|---|---|---|---|
| Br | H | (CF₃)₂CF | H | =C(H)— | =C(H)— | 0 |
| I | H | (CF₃)₂CF | H | =C(H)— | =C(H)— | 0 |
| Me | H | (CF₃)₂CF | H | =C(H)— | =C(H)— | 0 |
| Et | H | (CF₃)₂CF | H | =C(H)— | =C(H)— | 0 |
| Pr | H | (CF₃)₂CF | H | =C(H)— | =C(H)— | 0 |
| cPr | H | (CF₃)₂CF | H | =C(H)— | =C(H)— | 0 |
| CF₃ | H | (CF₃)₂CF | H | =C(H)— | =C(H)— | 0 |
| CH₃OCH₂ | H | (CF₃)₂CF | H | =C(H)— | =C(H)— | 0 |
| MeO | H | (CF₃)₂CF | H | =C(H)— | =C(H)— | 0 |
| EtO | H | (CF₃)₂CF | H | =C(H)— | =C(H)— | 0 |
| PrO | H | (CF₃)₂CF | H | =C(H)— | =C(H)— | 0 |
| CF₃CH₂O | H | (CF₃)₂CF | H | =C(H)— | =C(H)— | 0 |
| CHF₂CH₂O | H | (CF₃)₂CF | H | =C(H)— | =C(H)— | 0 |
| iPrO | H | (CF₃)₂CF | H | =C(H)— | =C(H)— | 0 |
| cPrCH₂O | H | (CF₃)₂CF | H | =C(H)— | =C(H)— | 0 |
| cPenO | H | (CF₃)₂CF | H | =C(H)— | =C(H)— | 0 |
| MeS | H | (CF₃)₂CF | H | =C(H)— | =C(H)— | 0 |
| MeS(O) | H | (CF₃)₂CF | H | =C(H)— | =C(H)— | 0 |
| MeS(O)₂ | H | (CF₃)₂CF | H | =C(H)— | =C(H)— | 0 |
| EtS | H | (CF₃)₂CF | H | =C(H)— | =C(H)— | 0 |
| EtS(O) | H | (CF₃)₂CF | H | =C(H)— | =C(H)— | 0 |
| EtS(O)₂ | H | (CF₃)₂CF | H | =C(H)— | =C(H)— | 0 |
| PrS | H | (CF₃)₂CF | H | =C(H)— | =C(H)— | 0 |
| PrS(O) | H | (CF₃)₂CF | H | =C(H)— | =C(H)— | 0 |

TABLE 15

| R¹ | R² | R³ | R⁴ | A¹ | A² | n |
|---|---|---|---|---|---|---|
| PrS(O)₂ | H | (CF₃)₂CF | H | =C(H)— | =C(H)— | 0 |
| iPrS | H | (CF₃)₂CF | H | =C(H)— | =C(H)— | 0 |
| iPrS(O) | H | (CF₃)₂CF | H | =C(H)— | =C(H)— | 0 |
| iPrS(O)₂ | H | (CF₃)₂CF | H | =C(H)— | =C(H)— | 0 |
| CF₃CH₂S | H | (CF₃)₂CF | H | =C(H)— | =C(H)— | 0 |
| CHF₂CH₂S | H | (CF₃)₂CF | H | =C(H)— | =C(H)— | 0 |
| MeHN | H | (CF₃)₂CF | H | =C(H)— | =C(H)— | 0 |
| Me₂N | H | (CF₃)₂CF | H | =C(H)— | =C(H)— | 0 |
| Me(iPr)N | H | (CF₃)₂CF | H | =C(H)— | =C(H)— | 0 |
| Ph | H | (CF₃)₂CF | H | =C(H)— | =C(H)— | 0 |
| 2-Py | H | (CF₃)₂CF | H | =C(H)— | =C(H)— | 0 |
| 3-Py | H | (CF₃)₂CF | H | =C(H)— | =C(H)— | 0 |
| 4-Py | H | (CF₃)₂CF | H | =C(H)— | =C(H)— | 0 |
| 1-Tz | H | (CF₃)₂CF | H | =C(H)— | =C(H)— | 0 |
| 1-Pz | H | (CF₃)₂CF | H | =C(H)— | =C(H)— | 0 |
| F | H | CF₃ | H | =C(H)— | N | 0 |
| Cl | H | CF₃ | H | =C(H)— | N | 0 |
| Br | H | CF₃ | H | =C(H)— | N | 0 |
| I | H | CF₃ | H | =C(H)— | N | 0 |
| Me | H | CF₃ | H | =C(H)— | N | 0 |
| Et | H | CF₃ | H | =C(H)— | N | 0 |
| Pr | H | CF₃ | H | =C(H)— | N | 0 |
| cPr | H | CF₃ | H | =C(H)— | N | 0 |
| CF₃ | H | CF₃ | H | =C(H)— | N | 0 |

TABLE 16

| R¹ | R² | R³ | R⁴ | A¹ | A² | n |
|---|---|---|---|---|---|---|
| CH₃OCH₂ | H | CF₃ | H | =C(H)— | N | 0 |
| MeO | H | CF₃ | H | =C(H)— | N | 0 |
| EtO | H | CF₃ | H | =C(H)— | N | 0 |
| PrO | H | CF₃ | H | =C(H)— | N | 0 |
| CF₃CH₂O | H | CF₃ | H | =C(H)— | N | 0 |
| CHF₂CH₂O | H | CF₃ | H | =C(H)— | N | 0 |
| iPrO | H | CF₃ | H | =C(H)— | N | 0 |
| cPrCH₂O | H | CF₃ | H | =C(H)— | N | 0 |
| cPenO | H | CF₃ | H | =C(H)— | N | 0 |
| MeS | H | CF₃ | H | =C(H)— | N | 0 |
| MeS(O) | H | CF₃ | H | =C(H)— | N | 0 |
| MeS(O)₂ | H | CF₃ | H | =C(H)— | N | 0 |
| EtS | H | CF₃ | H | =C(H)— | N | 0 |
| EtS(O) | H | CF₃ | H | =C(H)— | N | 0 |
| EtS(O)₂ | H | CF₃ | H | =C(H)— | N | 0 |
| PrS | H | CF₃ | H | =C(H)— | N | 0 |
| PrS(O) | H | CF₃ | H | =C(H)— | N | 0 |
| PrS(O)₂ | H | CF₃ | H | =C(H)— | N | 0 |
| iPrS | H | CF₃ | H | =C(H)— | N | 0 |
| iPrS(O) | H | CF₃ | H | =C(H)— | N | 0 |
| iPrS(O)₂ | H | CF₃ | H | =C(H)— | N | 0 |
| CF₃CH₂S | H | CF₃ | H | =C(H)— | N | 0 |
| CHF₂CH₂S | H | CF₃ | H | =C(H)— | N | 0 |
| MeHN | H | CF₃ | H | =C(H)— | N | 0 |

TABLE 17

| R¹ | R² | R³ | R⁴ | A¹ | A² | n |
|---|---|---|---|---|---|---|
| Me₂N | H | CF₃ | H | =C(H)— | N | 0 |
| Me(iPr)N | H | CF₃ | H | =C(H)— | N | 0 |
| CH₃C(O)NH | H | CF₃ | H | =C(H)— | N | 0 |
| MeOC(O)NH | H | CF₃ | H | =C(H)— | N | 0 |
| HC(O) | H | CF₃ | H | =C(H)— | N | 0 |
| CH₃C(O) | H | CF₃ | H | =C(H)— | N | 0 |
| HC(NOMe) | H | CF₃ | H | =C(H)— | N | 0 |
| CH₃C(NOMe) | H | CF₃ | H | =C(H)— | N | 0 |
| Ph | H | CF₃ | H | =C(H)— | N | 0 |
| 2-Py | H | CF₃ | H | =C(H)— | N | 0 |
| 3-Py | H | CF₃ | H | =C(H)— | N | 0 |
| 4-Py | H | CF₃ | H | =C(H)— | N | 0 |
| 1-Tz | H | CF₃ | H | =C(H)— | N | 0 |
| 1-Pz | H | CF₃ | H | =C(H)— | N | 0 |
| F | H | CF₃ | H | =C(H)— | N | 1 |
| Cl | H | CF₃ | H | =C(H)— | N | 1 |
| Br | H | CF₃ | H | =C(H)— | N | 1 |
| I | H | CF₃ | H | =C(H)— | N | 1 |
| Me | H | CF₃ | H | =C(H)— | N | 1 |
| Et | H | CF₃ | H | =C(H)— | N | 1 |
| Pr | H | CF₃ | H | =C(H)— | N | 1 |
| cPr | H | CF₃ | H | =C(H)— | N | 1 |
| CF₃ | H | CF₃ | H | =C(H)— | N | 1 |
| CH₃OCH₂ | H | CF₃ | H | =C(H)— | N | 1 |

TABLE 18

| R¹ | R² | R³ | R⁴ | A¹ | A² | n |
|---|---|---|---|---|---|---|
| MeO | H | CF₃ | H | =C(H)— | N | 1 |
| EtO | H | CF₃ | H | =C(H)— | N | 1 |
| PrO | H | CF₃ | H | =C(H)— | N | 1 |
| CF₃CH₂O | H | CF₃ | H | =C(H)— | N | 1 |
| CHF₂CH₂O | H | CF₃ | H | =C(H)— | N | 1 |
| iPrO | H | CF₃ | H | =C(H)— | N | 1 |
| Ph | H | CF₃ | H | =C(H)— | N | 1 |
| F | H | CF₃ | H | N | =C(H)— | 0 |
| Cl | H | CF₃ | H | N | =C(H)— | 0 |
| Br | H | CF₃ | H | N | =C(H)— | 0 |
| I | H | CF₃ | H | N | =C(H)— | 0 |
| Me | H | CF₃ | H | N | =C(H)— | 0 |
| Et | H | CF₃ | H | N | =C(H)— | 0 |
| Pr | H | CF₃ | H | N | =C(H)— | 0 |
| cPr | H | CF₃ | H | N | =C(H)— | 0 |
| CF₃ | H | CF₃ | H | N | =C(H)— | 0 |
| CH₃OCH₂ | H | CF₃ | H | N | =C(H)— | 0 |
| MeO | H | CF₃ | H | N | =C(H)— | 0 |
| EtO | H | CF₃ | H | N | =C(H)— | 0 |
| PrO | H | CF₃ | H | N | =C(H)— | 0 |
| CF₃CH₂O | H | CF₃ | H | N | =C(H)— | 0 |
| CHF₂CH₂O | H | CF₃ | H | N | =C(H)— | 0 |
| iPrO | H | CF₃ | H | N | =C(H)— | 0 |
| cPrCH₂O | H | CF₃ | H | N | =C(H)— | 0 |

TABLE 19

| R¹ | R² | R³ | R⁴ | A¹ | A² | n |
|---|---|---|---|---|---|---|
| cPenO | H | CF₃ | H | N | =C(H)— | 0 |
| MeS | H | CF₃ | H | N | =C(H)— | 0 |
| MeS(O) | H | CF₃ | H | N | =C(H)— | 0 |
| MeS(O)₂ | H | CF₃ | H | N | =C(H)— | 0 |
| EtS | H | CF₃ | H | N | =C(H)— | 0 |
| EtS(O) | H | CF₃ | H | N | =C(H)— | 0 |
| EtS(O)₂ | H | CF₃ | H | N | =C(H)— | 0 |
| PrS | H | CF₃ | H | N | =C(H)— | 0 |
| PrS(O) | H | CF₃ | H | N | =C(H)— | 0 |
| PrS(O)₂ | H | CF₃ | H | N | =C(H)— | 0 |
| iPrS | H | CF₃ | H | N | =C(H)— | 0 |
| iPrS(O) | H | CF₃ | H | N | =C(H)— | 0 |
| iPrS(O)₂ | H | CF₃ | H | N | =C(H)— | 0 |
| CF₃CH₂S | H | CF₃ | H | N | =C(H)— | 0 |
| CHF₂CH₂S | H | CF₃ | H | N | =C(H)— | 0 |

TABLE 19-continued

| R¹ | R² | R³ | R⁴ | A¹ | A² | n |
|---|---|---|---|---|---|---|
| MeHN | H | CF₃ | H | N | =C(H)— | 0 |
| Me₂N | H | CF₃ | H | N | =C(H)— | 0 |
| Me(iPr)N | H | CF₃ | H | N | =C(H)— | 0 |
| CH₃C(O)NH | H | CF₃ | H | N | =C(H)— | 0 |
| MeOC(O)NH | H | CF₃ | H | N | =C(H)— | 0 |
| HC(O) | H | CF₃ | H | N | =C(H)— | 0 |
| CH₃C(O) | H | CF₃ | H | N | =C(H)— | 0 |
| HC(NOMe) | H | CF₃ | H | N | =C(H)— | 0 |
| CH₃C(NOMe) | H | CF₃ | H | N | =C(H)— | 0 |

TABLE 20

| R¹ | R² | R³ | R⁴ | A¹ | A² | n |
|---|---|---|---|---|---|---|
| Ph | H | CF₃ | H | N | =C(H)— | 0 |
| 2-Py | H | CF₃ | H | N | =C(H)— | 0 |
| 3-Py | H | CF₃ | H | N | =C(H)— | 0 |
| 4-Py | H | CF₃ | H | N | =C(H)— | 0 |
| 1-Tz | H | CF₃ | H | N | =C(H)— | 0 |
| 1-Pz | H | CF₃ | H | N | =C(H)— | 0 |
| F | H | —CF₂OCF₂— | | =C(H)— | =C(H)— | 0 |
| Cl | H | —CF₂OCF₂— | | =C(H)— | =C(H)— | 0 |
| Br | H | —CF₂OCF₂— | | =C(H)— | =C(H)— | 0 |
| I | H | —CF₂OCF₂— | | =C(H)— | =C(H)— | 0 |
| Me | H | —CF₂OCF₂— | | =C(H)— | =C(H)— | 0 |
| Et | H | —CF₂OCF₂— | | =C(H)— | =C(H)— | 0 |
| Pr | H | —CF₂OCF₂— | | =C(H)— | =C(H)— | 0 |
| cPr | H | —CF₂OCF₂— | | =C(H)— | =C(H)— | 0 |
| CF₃ | H | —CF₂OCF₂— | | =C(H)— | =C(H)— | 0 |
| CH₃OCH₂ | H | —CF₂OCF₂— | | =C(H)— | =C(H)— | 0 |
| MeO | H | —CF₂OCF₂— | | =C(H)— | =C(H)— | 0 |
| EtO | H | —CF₂OCF₂— | | =C(H)— | =C(H)— | 0 |
| PrO | H | —CF₂OCF₂— | | =C(H)— | =C(H)— | 0 |
| CF₃CH₂O | H | —CF₂OCF₂— | | =C(H)— | =C(H)— | 0 |
| CHF₂CH₂O | H | —CF₂OCF₂— | | =C(H)— | =C(H)— | 0 |
| iPrO | H | —CF₂OCF₂— | | =C(H)— | =C(H)— | 0 |
| cPrCH₂O | H | —CF₂OCF₂— | | =C(H)— | =C(H)— | 0 |
| cPenO | H | —CF₂OCF₂— | | =C(H)— | =C(H)— | 0 |

TABLE 21

| R¹ | R² | R³ | R⁴ | A¹ | A² | n |
|---|---|---|---|---|---|---|
| MeS | H | —CF₂OCF₂— | | =C(H)— | =C(H)— | 0 |
| MeS(O) | H | —CF₂OCF₂— | | =C(H)— | =C(H)— | 0 |
| MeS(O)₂ | H | —CF₂OCF₂— | | =C(H)— | =C(H)— | 0 |
| EtS | H | —CF₂OCF₂— | | =C(H)— | =C(H)— | 0 |
| EtS(O) | H | —CF₂OCF₂— | | =C(H)— | =C(H)— | 0 |
| EtS(O)₂ | H | —CF₂OCF₂— | | =C(H)— | =C(H)— | 0 |
| PrS | H | —CF₂OCF₂— | | =C(H)— | =C(H)— | 0 |
| PrS(O) | H | —CF₂OCF₂— | | =C(H)— | =C(H)— | 0 |
| PrS(O)₂ | H | —CF₂OCF₂— | | =C(H)— | =C(H)— | 0 |
| iPrS | H | —CF₂OCF₂— | | =C(H)— | =C(H)— | 0 |
| iPrS(O) | H | —CF₂OCF₂— | | =C(H)— | =C(H)— | 0 |
| iPrS(O)₂ | H | —CF₂OCF₂— | | =C(H)— | =C(H)— | 0 |
| CF₃CH₂S | H | —CF₂OCF₂— | | =C(H)— | =C(H)— | 0 |
| CHF₂CH₂S | H | —CF₂OCF₂— | | =C(H)— | =C(H)— | 0 |
| MeHN | H | —CF₂OCF₂— | | =C(H)— | =C(H)— | 0 |
| Me₂N | H | —CF₂OCF₂— | | =C(H)— | =C(H)— | 0 |
| Me(iPr)N | H | —CF₂OCF₂— | | =C(H)— | =C(H)— | 0 |
| CH₃C(O)NH | H | —CF₂OCF₂— | | =C(H)— | =C(H)— | 0 |
| MeOC(O)NH | H | —CF₂OCF₂— | | =C(H)— | =C(H)— | 0 |
| HC(O) | H | —CF₂OCF₂— | | =C(H)— | =C(H)— | 0 |
| CH₃C(O) | H | —CF₂OCF₂— | | =C(H)— | =C(H)— | 0 |
| HC(NOMe) | H | —CF₂OCF₂— | | =C(H)— | =C(H)— | 0 |
| CH₃C(NOMe) | H | —CF₂OCF₂— | | =C(H)— | =C(H)— | 0 |
| Ph | H | —CF₂OCF₂— | | =C(H)— | =C(H)— | 0 |

TABLE 22

| R¹ | R² | R³ | R⁴ | A¹ | A² | n |
|---|---|---|---|---|---|---|
| 2-Py | H | | —CF₂OCF₂— | =C(H)— | =C(H)— | 0 |
| 3-Py | H | | —CF₂OCF₂— | =C(H)— | =C(H)— | 0 |
| 4-Py | H | | —CF₂OCF₂— | =C(H)— | =C(H)— | 0 |
| 1-Tz | H | | —CF₂OCF₂— | =C(H)— | =C(H)— | 0 |
| 1-Pz | H | | —CF₂OCF₂— | =C(H)— | =C(H)— | 0 |
| F | H | | —CF₂CH₂CH₂— | =C(H)— | =C(H)— | 0 |
| Cl | H | | —CF₂CH₂CH₂— | =C(H)— | =C(H)— | 0 |
| Br | H | | —CF₂CH₂CH₂— | =C(H)— | =C(H)— | 0 |
| I | H | | —CF₂CH₂CH₂— | =C(H)— | =C(H)— | 0 |
| Me | H | | —CF₂CH₂CH₂— | =C(H)— | =C(H)— | 0 |
| Et | H | | —CF₂CH₂CH₂— | =C(H)— | =C(H)— | 0 |
| Pr | H | | —CF₂CH₂CH₂— | =C(H)— | =C(H)— | 0 |
| cPr | H | | —CF₂CH₂CH₂— | =C(H)— | =C(H)— | 0 |
| CF₃ | H | | —CF₂CH₂CH₂— | =C(H)— | =C(H)— | 0 |
| CH₃OCH₂ | H | | —CF₂CH₂CH₂— | =C(H)— | =C(H)— | 0 |
| MeO | H | | —CF₂CH₂CH₂— | =C(H)— | =C(H)— | 0 |
| EtO | H | | —CF₂CH₂CH₂— | =C(H)— | =C(H)— | 0 |
| PrO | H | | —CF₂CH₂CH₂— | =C(H)— | =C(H)— | 0 |
| CF₃CH₂O | H | | —CF₂CH₂CH₂— | =C(H)— | =C(H)— | 0 |
| CHF₂CH₂O | H | | —CF₂CH₂CH₂— | =C(H)— | =C(H)— | 0 |
| iPrO | H | | —CF₂CH₂CH₂— | =C(H)— | =C(H)— | 0 |
| cPrCH₂O | H | | —CF₂CH₂CH₂— | =C(H)— | =C(H)— | 0 |
| cPenO | H | | —CF₂CH₂CH₂— | =C(H)— | =C(H)— | 0 |
| MeS | H | | —CF₂CH₂CH₂— | =C(H)— | =C(H)— | 0 |

TABLE 23

| R¹ | R² | R³ | R⁴ | A¹ | A² | n |
|---|---|---|---|---|---|---|
| MeS(O) | H | | —CF₂CH₂CH₂— | =C(H)— | =C(H)— | 0 |
| MeS(O)₂ | H | | —CF₂CH₂CH₂— | =C(H)— | =C(H)— | 0 |
| EtS | H | | —CF₂CH₂CH₂— | =C(H)— | =C(H)— | 0 |
| EtS(O) | H | | —CF₂CH₂CH₂— | =C(H)— | =C(H)— | 0 |
| EtS(O)₂ | H | | —CF₂CH₂CH₂— | =C(H)— | =C(H)— | 0 |
| PrS | H | | —CF₂CH₂CH₂— | =C(H)— | =C(H)— | 0 |
| PrS(O) | H | | —CF₂CH₂CH₂— | =C(H)— | =C(H)— | 0 |
| PrS(O)₂ | H | | —CF₂CH₂CH₂— | =C(H)— | =C(H)— | 0 |
| iPrS | H | | —CF₂CH₂CH₂— | =C(H)— | =C(H)— | 0 |
| iPrS(O) | H | | —CF₂CH₂CH₂— | =C(H)— | =C(H)— | 0 |
| iPrS(O)₂ | H | | —CF₂CH₂CH₂— | =C(H)— | =C(H)— | 0 |
| CF₃CH₂S | H | | —CF₂CH₂CH₂— | =C(H)— | =C(H)— | 0 |
| CHF₂CH₂S | H | | —CF₂CH₂CH₂— | =C(H)— | =C(H)— | 0 |
| MeHN | H | | —CF₂CH₂CH₂— | =C(H)— | =C(H)— | 0 |
| Me₂N | H | | —CF₂CH₂CH₂— | =C(H)— | =C(H)— | 0 |
| Me(iPr)N | H | | —CF₂CH₂CH₂— | =C(H)— | =C(H)— | 0 |
| F | H | | —CH₂CH₂CF₂— | =C(H)— | =C(H)— | 0 |
| Cl | H | | —CH₂CH₂CF₂— | =C(H)— | =C(H)— | 0 |
| Br | H | | —CH₂CH₂CF₂— | =C(H)— | =C(H)— | 0 |
| I | H | | —CH₂CH₂CF₂— | =C(H)— | =C(H)— | 0 |
| Me | H | | —CH₂CH₂CF₂— | =C(H)— | =C(H)— | 0 |
| Et | H | | —CH₂CH₂CF₂— | =C(H)— | =C(H)— | 0 |
| Pr | H | | —CH₂CH₂CF₂— | =C(H)— | =C(H)— | 0 |
| cPr | H | | —CH₂CH₂CF₂— | =C(H)— | =C(H)— | 0 |

TABLE 24

| R¹ | R² | R³ | R⁴ | A¹ | A² | n |
|---|---|---|---|---|---|---|
| CF₃ | H | | —CH₂CH₂CF₂— | =C(H)— | =C(H)— | 0 |
| CH₃OCH₂ | H | | —CH₂CH₂CF₂— | =C(H)— | =C(H)— | 0 |
| MeO | H | | —CH₂CH₂CF₂— | =C(H)— | =C(H)— | 0 |
| EtO | H | | —CH₂CH₂CF₂— | =C(H)— | =C(H)— | 0 |
| PrO | H | | —CH₂CH₂CF₂— | =C(H)— | =C(H)— | 0 |
| CF₃CH₂O | H | | —CH₂CH₂CF₂— | =C(H)— | =C(H)— | 0 |
| CHF₂CH₂O | H | | —CH₂CH₂CF₂— | =C(H)— | =C(H)— | 0 |
| iPrO | H | | —CH₂CH₂CF₂— | =C(H)— | =C(H)— | 0 |
| cPrCH₂O | H | | —CH₂CH₂CF₂— | =C(H)— | =C(H)— | 0 |
| cPenO | H | | —CH₂CH₂CF₂— | =C(H)— | =C(H)— | 0 |
| MeS | H | | —CH₂CH₂CF₂— | =C(H)— | =C(H)— | 0 |
| MeS(O) | H | | —CH₂CH₂CF₂— | =C(H)— | =C(H)— | 0 |
| MeS(O)₂ | H | | —CH₂CH₂CF₂— | =C(H)— | =C(H)— | 0 |
| EtS | H | | —CH₂CH₂CF₂— | =C(H)— | =C(H)— | 0 |
| EtS(O) | H | | —CH₂CH₂CF₂— | =C(H)— | =C(H)— | 0 |
| EtS(O)₂ | H | | —CH₂CH₂CF₂— | =C(H)— | =C(H)— | 0 |
| PrS | H | | —CH₂CH₂CF₂— | =C(H)— | =C(H)— | 0 |
| PrS(O) | H | | —CH₂CH₂CF₂— | =C(H)— | =C(H)— | 0 |
| PrS(O)₂ | H | | —CH₂CH₂CF₂— | =C(H)— | =C(H)— | 0 |
| iPrS | H | | —CH₂CH₂CF₂— | =C(H)— | =C(H)— | 0 |
| iPrS(O) | H | | —CH₂CH₂CF₂— | =C(H)— | =C(H)— | 0 |
| iPrS(O)₂ | H | | —CH₂CH₂CF₂— | =C(H)— | =C(H)— | 0 |
| CF₃CH₂S | H | | —CH₂CH₂CF₂— | =C(H)— | =C(H)— | 0 |
| CHF₂CH₂S | H | | —CH₂CH₂CF₂— | =C(H)— | =C(H)— | 0 |

TABLE 25

| R¹ | R² | R³ | R⁴ | A¹ | A² | n |
|---|---|---|---|---|---|---|
| MeHN | H | | —CH₂CH₂CF₂— | =C(H)— | =C(H)— | 0 |
| Me₂N | H | | —CH₂CH₂CF₂— | =C(H)— | =C(H)— | 0 |
| Me(iPr)N | H | | —CH₂CH₂CF₂— | =C(H)— | =C(H)— | 0 |
| F | H | | —CF₂CH₂CH₂CH₂— | =C(H)— | =C(H)— | 0 |
| Cl | H | | —CF₂CH₂CH₂CH₂— | =C(H)— | =C(H)— | 0 |
| Br | H | | —CF₂CH₂CH₂CH₂— | =C(H)— | =C(H)— | 0 |
| I | H | | —CF₂CH₂CH₂CH₂— | =C(H)— | =C(H)— | 0 |
| Me | H | | —CF₂CH₂CH₂CH₂— | =C(H)— | =C(H)— | 0 |
| Et | H | | —CF₂CH₂CH₂CH₂— | =C(H)— | =C(H)— | 0 |
| Pr | H | | —CF₂CH₂CH₂CH₂— | =C(H)— | =C(H)— | 0 |
| cPr | H | | —CF₂CH₂CH₂CH₂— | =C(H)— | =C(H)— | 0 |
| CF₃ | H | | —CF₂CH₂CH₂CH₂— | =C(H)— | =C(H)— | 0 |
| CH₃OCH₂ | H | | —CF₂CH₂CH₂CH₂— | =C(H)— | =C(H)— | 0 |
| MeO | H | | —CF₂CH₂CH₂CH₂— | =C(H)— | =C(H)— | 0 |
| EtO | H | | —CF₂CH₂CH₂CH₂— | =C(H)— | =C(H)— | 0 |
| PrO | H | | —CF₂CH₂CH₂CH₂— | =C(H)— | =C(H)— | 0 |
| CF₃CH₂O | H | | —CF₂CH₂CH₂CH₂— | =C(H)— | =C(H)— | 0 |
| CHF₂CH₂O | H | | —CF₂CH₂CH₂CH₂— | =C(H)— | =C(H)— | 0 |
| iPrO | H | | —CF₂CH₂CH₂CH₂— | =C(H)— | =C(H)— | 0 |
| cPrCH₂O | H | | —CF₂CH₂CH₂CH₂— | =C(H)— | =C(H)— | 0 |
| cPenO | H | | —CF₂CH₂CH₂CH₂— | =C(H)— | =C(H)— | 0 |
| MeS | H | | —CF₂CH₂CH₂CH₂— | =C(H)— | =C(H)— | 0 |
| MeS(O) | H | | —CF₂CH₂CH₂CH₂— | =C(H)— | =C(H)— | 0 |
| MeS(O)₂ | H | | —CF₂CH₂CH₂CH₂— | =C(H)— | =C(H)— | 0 |

TABLE 26

| R¹ | R² | R³ | R⁴ | A¹ | A² | n |
|---|---|---|---|---|---|---|
| EtS | H | | —CF₂CH₂CH₂CH₂— | =C(H)— | =C(H)— | 0 |
| EtS(O) | H | | —CF₂CH₂CH₂CH₂— | =C(H)— | =C(H)— | 0 |
| EtS(O)₂ | H | | —CF₂CH₂CH₂CH₂— | =C(H)— | =C(H)— | 0 |
| PrS | H | | —CF₂CH₂CH₂CH₂— | =C(H)— | =C(H)— | 0 |
| PrS(O) | H | | —CF₂CH₂CH₂CH₂— | =C(H)— | =C(H)— | 0 |
| PrS(O)₂ | H | | —CF₂CH₂CH₂CH₂— | =C(H)— | =C(H)— | 0 |
| iPrS | H | | —CF₂CH₂CH₂CH₂— | =C(H)— | =C(H)— | 0 |
| iPrS(O) | H | | —CF₂CH₂CH₂CH₂— | =C(H)— | =C(H)— | 0 |
| iPrS(O)₂ | H | | —CF₂CH₂CH₂CH₂— | =C(H)— | =C(H)— | 0 |
| CF₃CH₂S | H | | —CF₂CH₂CH₂CH₂— | =C(H)— | =C(H)— | 0 |
| CHF₂CH₂S | H | | —CF₂CH₂CH₂CH₂— | =C(H)— | =C(H)— | 0 |
| MeHN | H | | —CF₂CH₂CH₂CH₂— | =C(H)— | =C(H)— | 0 |
| Me₂N | H | | —CF₂CH₂CH₂CH₂— | =C(H)— | =C(H)— | 0 |
| Me(iPr)N | H | | —CF₂CH₂CH₂CH₂— | =C(H)— | =C(H)— | 0 |
| F | H | | —CF₂CH₂CH₂O— | =C(H)— | =C(H)— | 0 |
| Cl | H | | —CF₂CH₂CH₂O— | =C(H)— | =C(H)— | 0 |
| Br | H | | —CF₂CH₂CH₂O— | =C(H)— | =C(H)— | 0 |
| I | H | | —CF₂CH₂CH₂O— | =C(H)— | =C(H)— | 0 |
| Me | H | | —CF₂CH₂CH₂O— | =C(H)— | =C(H)— | 0 |
| Et | H | | —CF₂CH₂CH₂O— | =C(H)— | =C(H)— | 0 |
| Pr | H | | —CF₂CH₂CH₂O— | =C(H)— | =C(H)— | 0 |
| cPr | H | | —CF₂CH₂CH₂O— | =C(H)— | =C(H)— | 0 |
| CF₃ | H | | —CF₂CH₂CH₂O— | =C(H)— | =C(H)— | 0 |
| CH₃OCH₂ | H | | —CF₂CH₂CH₂O— | =C(H)— | =C(H)— | 0 |

TABLE 27

| R¹ | R² | R³ | R⁴ | A¹ | A² | n |
|---|---|---|---|---|---|---|
| MeO | H | —CF₂CH₂CH₂O— | | =C(H)— | =C(H)— | 0 |
| EtO | H | —CF₂CH₂CH₂O— | | =C(H)— | =C(H)— | 0 |
| PrO | H | —CF₂CH₂CH₂O— | | =C(H)— | =C(H)— | 0 |
| CF₃CH₂O | H | —CF₂CH₂CH₂O— | | =C(H)— | =C(H)— | 0 |
| CHF₂CH₂O | H | —CF₂CH₂CH₂O— | | =C(H)— | =C(H)— | 0 |
| iPrO | H | —CF₂CH₂CH₂O— | | =C(H)— | =C(H)— | 0 |
| cPrCH₂O | H | —CF₂CH₂CH₂O— | | =C(H)— | =C(H)— | 0 |
| cPenO | H | —CF₂CH₂CH₂O— | | =C(H)— | =C(H)— | 0 |
| MeS | H | —CF₂CH₂CH₂O— | | =C(H)— | =C(H)— | 0 |
| MeS(O) | H | —CF₂CH₂CH₂O— | | =C(H)— | =C(H)— | 0 |
| MeS(O)₂ | H | —CF₂CH₂CH₂O— | | =C(H)— | =C(H)— | 0 |
| EtS | H | —CF₂CH₂CH₂O— | | =C(H)— | =C(H)— | 0 |
| EtS(O) | H | —CF₂CH₂CH₂O— | | =C(H)— | =C(H)— | 0 |
| EtS(O)₂ | H | —CF₂CH₂CH₂O— | | =C(H)— | =C(H)— | 0 |
| PrS | H | —CF₂CH₂CH₂O— | | =C(H)— | =C(H)— | 0 |
| PrS(O) | H | —CF₂CH₂CH₂O— | | =C(H)— | =C(H)— | 0 |
| PrS(O)₂ | H | —CF₂CH₂CH₂O— | | =C(H)— | =C(H)— | 0 |
| iPrS | H | —CF₂CH₂CH₂O— | | =C(H)— | =C(H)— | 0 |
| iPrS(O) | H | —CF₂CH₂CH₂O— | | =C(H)— | =C(H)— | 0 |
| iPrS(O)₂ | H | —CF₂CH₂CH₂O— | | =C(H)— | =C(H)— | 0 |
| CF₃CH₂S | H | —CF₂CH₂CH₂O— | | =C(H)— | =C(H)— | 0 |
| CHF₂CH₂S | H | —CF₂CH₂CH₂O— | | =C(H)— | =C(H)— | 0 |
| MeHN | H | —CF₂CH₂CH₂O— | | =C(H)— | =C(H)— | 0 |
| Me₂N | H | —CF₂CH₂CH₂O— | | =C(H)— | =C(H)— | 0 |

TABLE 28

| R¹ | R² | R³ | R⁴ | A¹ | A² | n |
|---|---|---|---|---|---|---|
| Me(iPr)N | H | —CF₂CH₂CH₂O— | | =C(H)— | =C(H)— | 0 |
| F | H | H | CF₃ | =C(H)— | =C(H)— | 0 |
| Cl | H | H | CF₃ | =C(H)— | =C(H)— | 0 |
| Br | H | H | CF₃ | =C(H)— | =C(H)— | 0 |
| I | H | H | CF₃ | =C(H)— | =C(H)— | 0 |
| Me | H | H | CF₃ | =C(H)— | =C(H)— | 0 |
| Et | H | H | CF₃ | =C(H)— | =C(H)— | 0 |
| Pr | H | H | CF₃ | =C(H)— | =C(H)— | 0 |
| cPr | H | H | CF₃ | =C(H)— | =C(H)— | 0 |
| CF₃ | H | H | CF₃ | =C(H)— | =C(H)— | 0 |
| CH₃OCH₂ | H | H | CF₃ | =C(H)— | =C(H)— | 0 |
| MeO | H | H | CF₃ | =C(H)— | =C(H)— | 0 |
| EtO | H | H | CF₃ | =C(H)— | =C(H)— | 0 |
| PrO | H | H | CF₃ | =C(H)— | =C(H)— | 0 |
| CF₃CH₂O | H | H | CF₃ | =C(H)— | =C(H)— | 0 |
| CHF₂CH₂O | H | H | CF₃ | =C(H)— | =C(H)— | 0 |
| iPrO | H | H | CF₃ | =C(H)— | =C(H)— | 0 |
| cPrCH₂O | H | H | CF₃ | =C(H)— | =C(H)— | 0 |
| cPenO | H | H | CF₃ | =C(H)— | =C(H)— | 0 |
| MeS | H | H | CF₃ | =C(H)— | =C(H)— | 0 |
| MeS(O) | H | H | CF₃ | =C(H)— | =C(H)— | 0 |
| MeS(O)₂ | H | H | CF₃ | =C(H)— | =C(H)— | 0 |
| EtS | H | H | CF₃ | =C(H)— | =C(H)— | 0 |
| EtS(O) | H | H | CF₃ | =C(H)— | =C(H)— | 0 |

TABLE 29

| R¹ | R² | R³ | R⁴ | A¹ | A² | n |
|---|---|---|---|---|---|---|
| EtS(O)₂ | H | H | CF₃ | =C(H)— | =C(H)— | 0 |
| PrS | H | H | CF₃ | =C(H)— | =C(H)— | 0 |
| PrS(O) | H | H | CF₃ | =C(H)— | =C(H)— | 0 |
| PrS(O)₂ | H | H | CF₃ | =C(H)— | =C(H)— | 0 |
| iPrS | H | H | CF₃ | =C(H)— | =C(H)— | 0 |
| iPrS(O) | H | H | CF₃ | =C(H)— | =C(H)— | 0 |
| iPrS(O)₂ | H | H | CF₃ | =C(H)— | =C(H)— | 0 |
| CF₃CH₂S | H | H | CF₃ | =C(H)— | =C(H)— | 0 |
| CHF₂CH₂S | H | H | CF₃ | =C(H)— | =C(H)— | 0 |
| MeHN | H | H | CF₃ | =C(H)— | =C(H)— | 0 |
| Me₂N | H | H | CF₃ | =C(H)— | =C(H)— | 0 |
| Me(iPr)N | H | H | CF₃ | =C(H)— | =C(H)— | 0 |
| CH₃C(O)NH | H | H | CF₃ | =C(H)— | =C(H)— | 0 |
| MeOC(O)NH | H | H | CF₃ | =C(H)— | =C(H)— | 0 |
| HC(O) | H | H | CF₃ | =C(H)— | =C(H)— | 0 |
| CH₃C(O) | H | H | CF₃ | =C(H)— | =C(H)— | 0 |
| HC(NOMe) | H | H | CF₃ | =C(H)— | =C(H)— | 0 |
| CH₃C(NOMe) | H | H | CF₃ | =C(H)— | =C(H)— | 0 |
| Ph | H | H | CF₃ | =C(H)— | =C(H)— | 0 |
| 2-Py | H | H | CF₃ | =C(H)— | =C(H)— | 0 |
| 3-Py | H | H | CF₃ | =C(H)— | =C(H)— | 0 |
| 4-Py | H | H | CF₃ | =C(H)— | =C(H)— | 0 |
| 1-Tz | H | H | CF₃ | =C(H)— | =C(H)— | 0 |
| 1-Pz | H | H | CF₃ | =C(H)— | =C(H)— | 0 |

TABLE 30

| R¹ | R² | R³ | R⁴ | A¹ | A² | n |
|---|---|---|---|---|---|---|
| F | H | H | CF₃ | =C(H)— | =C(H)— | 1 |
| Cl | H | H | CF₃ | =C(H)— | =C(H)— | 1 |
| Br | H | H | CF₃ | =C(H)— | =C(H)— | 1 |
| I | H | H | CF₃ | =C(H)— | =C(H)— | 1 |
| Me | H | H | CF₃ | =C(H)— | =C(H)— | 1 |
| Et | H | H | CF₃ | =C(H)— | =C(H)— | 1 |
| Pr | H | H | CF₃ | =C(H)— | =C(H)— | 1 |
| cPr | H | H | CF₃ | =C(H)— | =C(H)— | 1 |
| CF₃ | H | H | CF₃ | =C(H)— | =C(H)— | 1 |
| CH₃OCH₂ | H | H | CF₃ | =C(H)— | =C(H)— | 1 |
| MeO | H | H | CF₃ | =C(H)— | =C(H)— | 1 |
| EtO | H | H | CF₃ | =C(H)— | =C(H)— | 1 |
| PrO | H | H | CF₃ | =C(H)— | =C(H)— | 1 |
| CF₃CH₂O | H | H | CF₃ | =C(H)— | =C(H)— | 1 |
| CHF₂CH₂O | H | H | CF₃ | =C(H)— | =C(H)— | 1 |
| iPrO | H | H | CF₃ | =C(H)— | =C(H)— | 1 |
| Ph | H | H | CF₃ | =C(H)— | =C(H)— | 1 |
| F | H | H | CF₃ | =C(H)— | N | 0 |
| Cl | H | H | CF₃ | =C(H)— | N | 0 |
| Br | H | H | CF₃ | =C(H)— | N | 0 |
| I | H | H | CF₃ | =C(H)— | N | 0 |
| Me | H | H | CF₃ | =C(H)— | N | 0 |
| Et | H | H | CF₃ | =C(H)— | N | 0 |
| Pr | H | H | CF₃ | =C(H)— | N | 0 |

TABLE 31

| R¹ | R² | R³ | R⁴ | A¹ | A² | n |
|---|---|---|---|---|---|---|
| cPr | H | H | CF₃ | =C(H)— | N | 0 |
| CF₃ | H | H | CF₃ | =C(H)— | N | 0 |
| CH₃OCH₂ | H | H | CF₃ | =C(H)— | N | 0 |
| MeO | H | H | CF₃ | =C(H)— | N | 0 |
| EtO | H | H | CF₃ | =C(H)— | N | 0 |
| PrO | H | H | CF₃ | =C(H)— | N | 0 |
| CF₃CH₂O | H | H | CF₃ | =C(H)— | N | 0 |
| CHF₂CH₂O | H | H | CF₃ | =C(H)— | N | 0 |
| iPrO | H | H | CF₃ | =C(H)— | N | 0 |
| cPrCH₂O | H | H | CF₃ | =C(H)— | N | 0 |
| cPenO | H | H | CF₃ | =C(H)— | N | 0 |
| MeS | H | H | CF₃ | =C(H)— | N | 0 |
| MeS(O) | H | H | CF₃ | =C(H)— | N | 0 |
| MeS(O)₂ | H | H | CF₃ | =C(H)— | N | 0 |
| EtS | H | H | CF₃ | =C(H)— | N | 0 |
| EtS(O) | H | H | CF₃ | =C(H)— | N | 0 |
| EtS(O)₂ | H | H | CF₃ | =C(H)— | N | 0 |
| PrS | H | H | CF₃ | =C(H)— | N | 0 |
| PrS(O) | H | H | CF₃ | =C(H)— | N | 0 |
| PrS(O)₂ | H | H | CF₃ | =C(H)— | N | 0 |
| iPrS | H | H | CF₃ | =C(H)— | N | 0 |
| iPrS(O) | H | H | CF₃ | =C(H)— | N | 0 |
| iPrS(O)₂ | H | H | CF₃ | =C(H)— | N | 0 |
| CF₃CH₂S | H | H | CF₃ | =C(H)— | N | 0 |

TABLE 32

| R¹ | R² | R³ | R⁴ | A¹ | A² | n |
|---|---|---|---|---|---|---|
| CHF₂CH₂S | H | H | CF₃ | =C(H)— | N | 0 |
| MeHN | H | H | CF₃ | =C(H)— | N | 0 |
| Me₂N | H | H | CF₃ | =C(H)— | N | 0 |
| Me(iPr)N | H | H | CF₃ | =C(H)— | N | 0 |
| Ph | H | H | CF₃ | =C(H)— | N | 0 |
| 2-Py | H | H | CF₃ | =C(H)— | N | 0 |
| 3-Py | H | H | CF₃ | =C(H)— | N | 0 |
| 4-Py | H | H | CF₃ | =C(H)— | N | 0 |
| 1-Tz | H | H | CF₃ | =C(H)— | N | 0 |
| 1-Pz | H | H | CF₃ | =C(H)— | N | 0 |
| F | H | H | CF₃ | N | =C(H)— | 0 |
| Cl | H | H | CF₃ | N | =C(H)— | 0 |
| Br | H | H | CF₃ | N | =C(H)— | 0 |
| I | H | H | CF₃ | N | =C(H)— | 0 |
| Me | H | H | CF₃ | N | =C(H)— | 0 |
| Et | H | H | CF₃ | N | =C(H)— | 0 |
| Pr | H | H | CF₃ | N | =C(H)— | 0 |
| cPr | H | H | CF₃ | N | =C(H)— | 0 |
| CF₃ | H | H | CF₃ | N | =C(H)— | 0 |
| CH₃OCH₂ | H | H | CF₃ | N | =C(H)— | 0 |
| MeO | H | H | CF₃ | N | =C(H)— | 0 |
| EtO | H | H | CF₃ | N | =C(H)— | 0 |
| PrO | H | H | CF₃ | N | =C(H)— | 0 |
| CF₃CH₂O | H | H | CF₃ | N | =C(H)— | 0 |

TABLE 33

| R¹ | R² | R³ | R⁴ | A¹ | A² | n |
|---|---|---|---|---|---|---|
| CHF₂CH₂O | H | H | CF₃ | N | =C(H)— | 0 |
| iPrO | H | H | CF₃ | N | =C(H)— | 0 |
| cPrCH₂O | H | H | CF₃ | N | =C(H)— | 0 |
| cPenO | H | H | CF₃ | N | =C(H)— | 0 |
| MeS | H | H | CF₃ | N | =C(H)— | 0 |
| MeS(O) | H | H | CF₃ | N | =C(H)— | 0 |
| MeS(O)₂ | H | H | CF₃ | N | =C(H)— | 0 |
| EtS | H | H | CF₃ | N | =C(H)— | 0 |
| EtS(O) | H | H | CF₃ | N | =C(H)— | 0 |
| EtS(O)₂ | H | H | CF₃ | N | =C(H)— | 0 |
| PrS | H | H | CF₃ | N | =C(H)— | 0 |
| PrS(O) | H | H | CF₃ | N | =C(H)— | 0 |
| PrS(O)₂ | H | H | CF₃ | N | =C(H)— | 0 |
| iPrS | H | H | CF₃ | N | =C(H)— | 0 |
| iPrS(O) | H | H | CF₃ | N | =C(H)— | 0 |
| iPrS(O)₂ | H | H | CF₃ | N | =C(H)— | 0 |
| CF₃CH₂S | H | H | CF₃ | N | =C(H)— | 0 |
| CHF₂CH₂S | H | H | CF₃ | N | =C(H)— | 0 |
| MeHN | H | H | CF₃ | N | =C(H)— | 0 |
| Me₂N | H | H | CF₃ | N | =C(H)— | 0 |
| Me(iPr)N | H | H | CF₃ | N | =C(H)— | 0 |
| Ph | H | H | CF₃ | N | =C(H)— | 0 |
| 2-Py | H | H | CF₃ | N | =C(H)— | 0 |
| 3-Py | H | H | CF₃ | N | =C(H)— | 0 |

TABLE 34

| R¹ | R² | R³ | R⁴ | A¹ | A² | n |
|---|---|---|---|---|---|---|
| 4-Py | H | H | CF₃ | N | =C(H)— | 0 |
| 1-Tz | H | H | CF₃ | N | =C(H)— | 0 |
| 1-Pz | H | H | CF₃ | N | =C(H)— | 0 |
| F | H | H | CF₃O | =C(H)— | =C(H)— | 0 |
| Cl | H | H | CF₃O | =C(H)— | =C(H)— | 0 |
| Br | H | H | CF₃O | =C(H)— | =C(H)— | 0 |
| I | H | H | CF₃O | =C(H)— | =C(H)— | 0 |
| Me | H | H | CF₃O | =C(H)— | =C(H)— | 0 |
| Et | H | H | CF₃O | =C(H)— | =C(H)— | 0 |
| Pr | H | H | CF₃O | =C(H)— | =C(H)— | 0 |
| cPr | H | H | CF₃O | =C(H)— | =C(H)— | 0 |
| CF₃ | H | H | CF₃O | =C(H)— | =C(H)— | 0 |
| CH₃OCH₂ | H | H | CF₃O | =C(H)— | =C(H)— | 0 |
| MeO | H | H | CF₃O | =C(H)— | =C(H)— | 0 |
| EtO | H | H | CF₃O | =C(H)— | =C(H)— | 0 |

TABLE 34-continued

| R¹ | R² | R³ | R⁴ | A¹ | A² | n |
|---|---|---|---|---|---|---|
| PrO | H | H | CF₃O | =C(H)— | =C(H)— | 0 |
| CF₃CH₂O | H | H | CF₃O | =C(H)— | =C(H)— | 0 |
| CHF₂CH₂O | H | H | CF₃O | =C(H)— | =C(H)— | 0 |
| iPrO | H | H | CF₃O | =C(H)— | =C(H)— | 0 |
| cPrCH₂O | H | H | CF₃O | =C(H)— | =C(H)— | 0 |
| cPenO | H | H | CF₃O | =C(H)— | =C(H)— | 0 |
| MeS | H | H | CF₃O | =C(H)— | =C(H)— | 0 |
| MeS(O) | H | H | CF₃O | =C(H)— | =C(H)— | 0 |
| MeS(O)₂ | H | H | CF₃O | =C(H)— | =C(H)— | 0 |

TABLE 35

| R¹ | R² | R³ | R⁴ | A¹ | A² | n |
|---|---|---|---|---|---|---|
| EtS | H | H | CF₃O | =C(H)— | =C(H)— | 0 |
| EtS(O) | H | H | CF₃O | =C(H)— | =C(H)— | 0 |
| EtS(O)₂ | H | H | CF₃O | =C(H)— | =C(H)— | 0 |
| PrS | H | H | CF₃O | =C(H)— | =C(H)— | 0 |
| PrS(O) | H | H | CF₃O | =C(H)— | =C(H)— | 0 |
| PrS(O)₂ | H | H | CF₃O | =C(H)— | =C(H)— | 0 |
| iPrS | H | H | CF₃O | =C(H)— | =C(H)— | 0 |
| iPrS(O) | H | H | CF₃O | =C(H)— | =C(H)— | 0 |
| iPrS(O)₂ | H | H | CF₃O | =C(H)— | =C(H)— | 0 |
| CF₃CH₂S | H | H | CF₃O | =C(H)— | =C(H)— | 0 |
| CHF₂CH₂S | H | H | CF₃O | =C(H)— | =C(H)— | 0 |
| MeHN | H | H | CF₃O | =C(H)— | =C(H)— | 0 |
| Me₂N | H | H | CF₃O | =C(H)— | =C(H)— | 0 |
| Me(iPr)N | H | H | CF₃O | =C(H)— | =C(H)— | 0 |
| Ph | H | H | CF₃O | =C(H)— | =C(H)— | 0 |
| 2-Py | H | H | CF₃O | =C(H)— | =C(H)— | 0 |
| 3-Py | H | H | CF₃O | =C(H)— | =C(H)— | 0 |
| 4-Py | H | H | CF₃O | =C(H)— | =C(H)— | 0 |
| 1-Tz | H | H | CF₃O | =C(H)— | =C(H)— | 0 |
| 1-Pz | H | H | CF₃O | =C(H)— | =C(H)— | 0 |
| F | H | H | CF₃O | =C(H)— | =C(H)— | 1 |
| Cl | H | H | CF₃O | =C(H)— | =C(H)— | 1 |
| Br | H | H | CF₃O | =C(H)— | =C(H)— | 1 |
| I | H | H | CF₃O | =C(H)— | =C(H)— | 1 |

TABLE 36

| R¹ | R² | R³ | R⁴ | A¹ | A² | n |
|---|---|---|---|---|---|---|
| Me | H | H | CF₃O | =C(H)— | =C(H)— | 1 |
| Et | H | H | CF₃O | =C(H)— | =C(H)— | 1 |
| Pr | H | H | CF₃O | =C(H)— | =C(H)— | 1 |
| cPr | H | H | CF₃O | =C(H)— | =C(H)— | 1 |
| CF₃ | H | H | CF₃O | =C(H)— | =C(H)— | 1 |
| CH₃OCH₂ | H | H | CF₃O | =C(H)— | =C(H)— | 1 |
| MeO | H | H | CF₃O | =C(H)— | =C(H)— | 1 |
| EtO | H | H | CF₃O | =C(H)— | =C(H)— | 1 |
| PrO | H | H | CF₃O | =C(H)— | =C(H)— | 1 |
| CF₃CH₂O | H | H | CF₃O | =C(H)— | =C(H)— | 1 |
| CHF₂CH₂O | H | H | CF₃O | =C(H)— | =C(H)— | 1 |
| iPrO | H | H | CF₃O | =C(H)— | =C(H)— | 1 |
| Ph | H | H | CF₃O | =C(H)— | =C(H)— | 1 |
| F | H | H | CF₃S | =C(H)— | =C(H)— | 0 |
| Cl | H | H | CF₃S | =C(H)— | =C(H)— | 0 |
| Br | H | H | CF₃S | =C(H)— | =C(H)— | 0 |
| I | H | H | CF₃S | =C(H)— | =C(H)— | 0 |
| Me | H | H | CF₃S | =C(H)— | =C(H)— | 0 |
| Et | H | H | CF₃S | =C(H)— | =C(H)— | 0 |
| Pr | H | H | CF₃S | =C(H)— | =C(H)— | 0 |
| cPr | H | H | CF₃S | =C(H)— | =C(H)— | 0 |
| CF₃ | H | H | CF₃S | =C(H)— | =C(H)— | 0 |
| CH₃OCH₂ | H | H | CF₃S | =C(H)— | =C(H)— | 0 |
| MeO | H | H | CF₃S | =C(H)— | =C(H)— | 0 |

TABLE 37

| $R^1$ | $R^2$ | $R^3$ | $R^4$ | $A^1$ | $A^2$ | n |
|---|---|---|---|---|---|---|
| EtO | H | H | $CF_3S$ | =C(H)— | =C(H)— | 0 |
| PrO | H | H | $CF_3S$ | =C(H)— | =C(H)— | 0 |
| $CF_3CH_2O$ | H | H | $CF_3S$ | =C(H)— | =C(H)— | 0 |
| $CHF_2CH_2O$ | H | H | $CF_3S$ | =C(H)— | =C(H)— | 0 |
| iPrO | H | H | $CF_3S$ | =C(H)— | =C(H)— | 0 |
| cPrCH$_2$O | H | H | $CF_3S$ | =C(H)— | =C(H)— | 0 |
| cPenO | H | H | $CF_3S$ | =C(H)— | =C(H)— | 0 |
| MeS | H | H | $CF_3S$ | =C(H)— | =C(H)— | 0 |
| MeS(O) | H | H | $CF_3S$ | =C(H)— | =C(H)— | 0 |
| MeS(O)$_2$ | H | H | $CF_3S$ | =C(H)— | =C(H)— | 0 |
| EtS | H | H | $CF_3S$ | =C(H)— | =C(H)— | 0 |
| EtS(O) | H | H | $CF_3S$ | =C(H)— | =C(H)— | 0 |
| EtS(O)$_2$ | H | H | $CF_3S$ | =C(H)— | =C(H)— | 0 |
| PrS | H | H | $CF_3S$ | =C(H)— | =C(H)— | 0 |
| PrS(O) | H | H | $CF_3S$ | =C(H)— | =C(H)— | 0 |
| PrS(O)$_2$ | H | H | $CF_3S$ | =C(H)— | =C(H)— | 0 |
| iPrS | H | H | $CF_3S$ | =C(H)— | =C(H)— | 0 |
| iPrS(O) | H | H | $CF_3S$ | =C(H)— | =C(H)— | 0 |
| iPrS(O)$_2$ | H | H | $CF_3S$ | =C(H)— | =C(H)— | 0 |
| $CF_3CH_2S$ | H | H | $CF_3S$ | =C(H)— | =C(H)— | 0 |
| $CHF_2CH_2S$ | H | H | $C_{F3}S$ | =C(H)— | =C(H)— | 0 |
| MeHN | H | H | $CF_3S$ | =C(H)— | =C(H)— | 0 |
| Me$_2$N | H | H | $CF_3S$ | =C(H)— | =C(H)— | 0 |
| Me(iPr)N | H | H | $CF_3S$ | =C(H)— | =C(H)— | 0 |

TABLE 38

| $R^1$ | $R^2$ | $R^3$ | $R^4$ | $A^1$ | $A^2$ | n |
|---|---|---|---|---|---|---|
| Ph | H | H | $CF_3S$ | =C(H)— | =C(H)— | 0 |
| 2-Py | H | H | $CF_3S$ | =C(H)— | =C(H)— | 0 |
| 3-Py | H | H | $CF_3S$ | =C(H)— | =C(H)— | 0 |
| 4-Py | H | H | $CF_3S$ | =C(H)— | =C(H)— | 0 |
| 1-Tz | H | H | $CF_3S$ | =C(H)— | =C(H)— | 0 |
| 1-Pz | H | H | $CF_3S$ | =C(H)— | =C(H)— | 0 |

The arthropod pest control composition of the present invention comprises the present compound and an inert carrier. The arthropod pest control composition of the present invention is, in general, a formulation obtained by mixing the present compound and a solid carrier, liquid carrier, gaseous carrier and/or bait (poison bait base material) and the like, and if necessary, adding a surfactant, and other formulation auxiliaries. Examples of the formulation include an oil solution, an emulsifiable concentrate, a flowable formulation, a wettable powder, a granule, a dust and a microcapsule. These formulations are processed into a poison bait or sheet and used, in some cases. The arthropod pest control composition of the present invention contains the present compound usually in an amount of 0.01 to 95 wt %.

Examples of the solid carrier used in making a formulation include fine powders or granular materials made of clays (kaolin clay, diatomaceous earth, bentonite, Fubasami clay, acid clay and the like), synthetic hydrous silicon oxide, talcs, ceramic, other inorganic minerals (sericite, quartz, sulfur, activated carbon, calcium carbonate, etc.), chemical fertilizers (ammonium sulfate, ammonium nitrate, ammonium chloride, etc.), and the like. Examples of the liquid carrier include water, alcohols (methanol, ethanol, 2-propanol, ethylene glycol etc.), ketones (acetone, methyl ethyl ketone, methyl isobutyl ketone, cyclohexanone, etc.), aromatic hydrocarbons (toluene, xylene, ethylbenzene, methylnaphthalene, etc.), aliphatic hydrocarbons (hexane, cyclohexane, kerosene, light oil, etc.), esters (ethyl acetate, butyl acetate, etc.), nitriles (acetonitrile, isobutyronitrile, etc.), ethers (ethylene glycol dimethyl ether, diisopropyl ether, 1,4-dioxane, tetrahydrofuran, etc.), acid amides (N,N-dimethylformamide, N,N-dimethylacetamide, etc.), halogenated hydrocarbons (dichloromethane, trichloroethane, etc.), dimethyl sulfoxide and vegetable oils (soybean oil, cottonseed oil, etc.).

Examples of the gaseous carrier include fluorocarbon, butane gas, LPG (liquefied petroleum gas), dimethyl ether, and carbon dioxide.

Examples of the surfactant include alkyl sulfate ester salts, alkyl sulfonate salts, alkyl aryl sulfonate salts, alkyl aryl ethers and polyoxyethylene compounds thereof, polyethylene glycol ethers, polyhydric alcohol esters, and sugar alcohol derivatives.

The other formulation auxiliaries include fixing agents, dispersing agents, stabilizers and the like, and specific examples thereof include casein, gelatin, saccharides (starch, gum arabic, cellulose derivatives, alginic acid, etc.), lignin derivatives, synthetic water-soluble polymers (polyvinyl alcohol, polyvinyl pyrrolidone, polyacrylic acids, etc.), PAP (acid isopropyl phosphate), BHT (2,6-di-tert-butyl-4-methylphenol), BHA (a mixture of 2-tert-butyl-4-methoxyphenol and 3-tert-butyl-4-methoxyphenol), mineral oils, fatty acids and fatty esters.

Examples of the poison bait base material include bait components such as cereal flour, vegetable oil, sugar and crystalline cellulose. In the poison bait, if necessary, an antioxidant such as dibutylhydroxytoluene and nordihydroguaiaretic acid, a preservative such as dehydroacetic acid, an aversive agent to prevent accidental ingestion such as a red pepper powder, a harmful insect attractant fragrance such as a cheese fragrance, onion fragrance and peanut oil are added.

The arthropod pest control composition of the present invention is used by applying to arthropod pests directly and/or to areas where arthropod pests live (nest, plant body, soil and the like). In the case of controlling arthropod pests parasitic on a cultivation plant, for example, the arthropod pest control composition of the present invention is sprayed onto parts above ground of the cultivation plant, or the arthropod pest control composition of the present invention is injected to the foot of the plant, and the like.

When the arthropod pest control composition of the present invention is used for control of arthropod pests in the agroforestry field, its application amount is usually 0.1 to 1000 g in terms of the amount of the present compound per 1000 $m^2$. When the arthropod pest control composition of the present invention is formulated into an emulsifiable concentrate, flowable formulation, wettable powder, microcapsule and the like, the composition is diluted with water so that the concentration of the present compound is usually 1 to 10000 ppm and sprayed. When the arthropod pest control composition of the present invention is formulated into an oil solution, granule, dust and the like, the composition is used usually as it is.

When the arthropod pest control composition of the present invention is used for control of arthropod pests in the epidemic prevention field, its application amount is usually 0.01 to 1000 mg in terms of the amount of the present compound per 1 $m^2$ of the application area when treated on a surface, and usually 0.01 to 500 mg in terms of the amount of the present compound per 1 $m^3$ of the application space when treated in a space. When the arthropod pest control composition of the present invention is formulated into an emulsifiable concentrate, flowable formulation, wettable powder, microcapsule and the like, the composition is diluted with water so that the concentration of the present compound is usually 0.1 to 1000 ppm and applied. When the arthropod pest control composition of the present invention is formulated into an oil solution, aerosol, smoking agent, poison bait and the like, the composition is used usually as it is.

The arthropod pest control composition of the present invention may contain active ingredients of insecticides, active ingredients of acaricides, active ingredients of nematicides, active ingredients of fungicides, active ingredients of herbicides and/or active ingredients of plant growth regulators, in addition to the present compound.

Examples of the active ingredients of insecticides include the following components.

(1) Organic Phosphorus Compounds:
Aacephate, Aluminium phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos, and the like;

(2) Carbamate Compounds:
Alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb, and the like;

(3) Pyrethroid Compounds:
Acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, taufluvalinate, metofluthrin, profluthrin, dimefluthrin, 2,3,5,6-tetrafluoro-4-(methoxymethyl)benzyl (EZ)-(1RS,3RS;1RS,3SR)-2,2-dimethyl-3-prop-1-enylcyclopropane carboxylate, 2,3,5,6-tetrafluoro-4-methylbenzyl (EZ)-(1RS,3RS;1RS,3SR)-2,2-dimethyl-3-prop-1-enylcyclopropane carboxylate, 2,3,5,6-tetrafluoro-4-(methoxymethyl)benzyl (1RS,3RS;1RS,3SR)-2,2-dimethyl-3-(2-methyl-1-propenyl)cyclopropane carboxylate and the like;

(4) Nereistoxin Compounds:
Cartap, bensultap, thiocyclam, monosultap, bisultap, and the like;

(5) Neonicotinoid Compounds:
Imidacloprid, nitenpyram, acetamiprid, thiamethoxam, thiacloprid, dinotefuran, clothianidin, and the like;

(6) Benzoylurea Compounds:
Chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, triazuron, and the like;

(7) Phenylpyrazole Compounds:
Acetoprole, ethiprole, fipronil, vaniliprole, pyriprole, pyrafluprole, and the like;

(8) Bt Toxin:
Live spores derived from and crystal toxins produced from *Bacillus thuringiesis* and a mixture thereof;

(9) Hydrazine Compounds:
Chromafenozide, halofenozide, methoxyfenozide, tebufenozide, and the like;

(10) Organic Chlorine Compounds:
Aldrin, dieldrin, dienochlor, endosulfan, methoxychlor, and the like;

(11) Others:
Machine oil, nicotine-sulfate; avermectin-B, bromopropylate, buprofezin, chlorphenapyr, cyantraniliprole, cyromazine, D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfoxaflor, sulfur, metaflumizone, spirotetramat, pyrifluquinazone, spinetoram, chlorantraniliprole, tralopyril, any compound represented by the following formula (A):

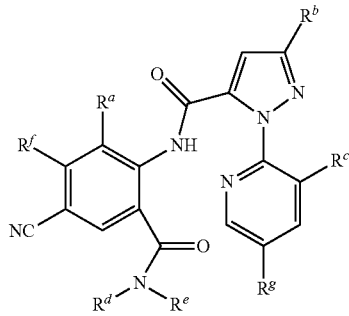

wherein, $R^a$ represents Me, Cl, Br or F; $R^b$ represents F, Cl, Br, C1-C4 haloalkyl, or C1-C4 haloalkoxy; $R^c$ represents F, Cl or Br; $R^d$ represents a C1-C4 alkyl, a C3-C4 alkenyl, C3-C4 alkynyl or C3-C5 cycloalkylalkyl optionally substituted by H, one or more halogen atoms; CN; SMe; S(O)Me; S(O)$_2$Me and OMe; $R^e$ represents H or Me; $R^f$ represents H, F or Cl; and $R^g$ represents H, F or Cl.

Examples of the active ingredients of acaricides include the following components.

acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite (BPPS), polynactins, pyridaben, pyrimidifen, tebufenpyrad, tetradifon, spirodiclofen, spiromesifen, spirotetramat, amidoflumet and cyenopyrafen.

Examples of the active ingredients of nematicides include the following components.

DCIP, fosthiazate, levamisol, methylsothiocyanate, morantel tartarate and imicyafos.

Examples of the active ingredients of fungicides include the following components.

azole compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil and flutriafol;

cyclic amine compounds such as fenpropimorph, tridemorph and fenpropidin;

benzimidazole compounds such as carbendezim, benomyl, thiabendazole and thiophanate-methyl;

procymidone, cyprodinil, pyrimethanil, diethofencarb, thiuram, fluazinam, mancozeb, iprodione, vinclozolin, chlorothalonil, captan, mepanipyrim, fenpiclonil, fludioxonil, dichlofluanid, folpet, kresoxim-methyl, azoxystrobin, trifloxystrobin, fluoxastrobin, picoxystrobin, pyraclostrobin, dimoxystrobin, pyribencarb, spiroxamine, quinoxyfen, fenhexamid, famoxadone, fenamidone, zoxamide, ethaboxam, amisulbrom, iprovalicarb, benthiavalicarb, cyazofamid, mandipropamid, boscalid, penthiopyrad, metrafenone, fluopiran, bixafen, cyflufenamid and proquinazid.

Examples of the active ingredients of herbicides include the following components.

(1) Phenoxyfatty Acid Compounds 2,4-PA, MCP, MCPB, phenothiol, mecoprop, fluoroxypyr, triclopyr, clomeprop, naproanilide and the like;

(2) Benzoic Acid Compounds 2,3,6-TBA, dicamba, clopyralid, picloram, aminopyralid, quinclorac, quinmerac and the like;

(3) Urea Compounds diuron, linuron, chlortoluron, isoproturon, fluometuron, isouron, tebuthiuron, methabenzthiazuron, cumyluron, daimuron, methyl-daimuron and the like;

(4) Triazine Compounds atrazine, ametoryn, cyanazine, simazine, propazine, simetryn, dimethametryn, prometryn, metribuzin, triaziflam, indaziflam and the like;

(5) Bipyridinium Compounds paraquat, diquat and the like;

(6) Hydroxybenzonitrile Compounds bromoxynil, ioxynil and the like;

(7) Dinitroaniline Compounds pendimethalin, prodiamine, trifluralin and the like;

(8) Organophosphorus Compounds amiprofos-methyl, butamifos, bensulide, piperophos, anilofos, glyphosate, glufosinate, glufosinate-P, bialaphos and the like;

(9) Carbamate Compounds di-allate, tri-allate, EPTC, butylate, benthiocarb, esprocarb, molinate, dimepiperate, swep, chlorpropham, phenmedipham, phenisopham, pyributicarb, asulam and the like;

(10) Acid Amide Compounds propanil, propyzamide, bromobutide, etobenzanid and the like;

(11) Chloroacetanilide Compounds acetochlor, alachlor, butachlor, dimethenamid, propachlor, metazachlor, metolachlor, pretilachlor, thenylchlor, pethoxamid and the like;

(12) Diphenylether Compounds acifluorfen-sodium, bifenox, oxyfluorfen, lactofen, fomesafen, chlomethoxynil, aclonifen and the like;

(13) Cyclic Imide Compounds oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, saflufenacil and the like;

(14) Pyrazole Compounds benzofenap, pyrazolate, pyrazoxyfen, topramezone, pyrasulfotole and the like;

(15) Triketone Compounds isoxaflutole, benzobicyclon, sulcotrione, mesotrione, tembotrione, tefuryltrione, bicyclopyrone and the like;

(16) Aryloxyphenoxypropionic Acid Compounds clodinafop-propargyl, cyhalofop-butyl, diclofop-methyl, fenoxaprop-ethyl, fluazifop-butyl, haloxyfop-methyl, quizalofop-ethyl, metamifop and the like;

(17) Trioneoxime Compounds alloxydim-sodium, sethoxydim, butroxydim, clethodim, cloproxydim, cycloxydim, tepraloxydim, tralkoxydim, profoxydim and the like;

(18) Sulfonylurea Compounds chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, propyrisulfuron, metazosulfuron, and the like;

(19) Imidazolinone Compounds imazamethabenz-methyl, imazamethapyr, imazamox, imazapyr, imazaquin, imazethapyr and the like;

(20) Sulfonamide Compounds flumetsulam, metosulam, diclosulam, florasulam, cloransulam-methyl, penoxsulam, pyroxsulam and the like;

(21) Pyrimidinyloxybenzoic Acid Compounds pyrithiobac-sodium, bispyribac-sodium, pyriminobac-methyl, pyribenzoxim, pyriftalid, pyrimisulfan and the like;

(22) Others bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarcazone, methiozolin and fenoxasulfone.

Examples of the active ingredients of plant growth regulators include the following compounds.

hymexazol, paclobutrazol, uniconazole-P, inabenfide, prohexadione-calcium, aviglycine, 1-naphthylacetamide (naphthalene acetamide), abscisic acid, indolebutyric acid, ethychlozate, ethephon, cloxyfonac, chlormequat, dichlorprop, gibberellins, prohydrojasmon, benzylaminopurine (benzyladenine), forchlorfenuron, maleic hydrazide, calcium peroxide, mepiquat-chloride and 4-CPA (4-chlorophenoxyacetic acid).

Examples of arthropod pests on which the present compound exhibits an effect include harmful insects and harmful mites. Examples thereof include the following organisms.

Hemiptera:

Planthoppers (Delphacidae) such as small brown planthopper (*Laodelphax striatellus*), brown rice planthopper (*Nilaparvata lugens*), white-backed rice planthopper (*Sogatella furcifera*) and the like; leafhoppers (Deltocephalidae) such as green rice leafhopper (*Nephotettix cincticeps*), green rice leafhopper (*Nephotettix virescens*), tea green leafhopper (*Empoasca onukii*) and the like; aphids (Aphididae) such as cotton aphid (*Aphis gossypii*), green peach aphid (*Myzus persicae*), cabbage aphid (*Brevicoryne brassicae*), piraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), mealy plum aphid (*Hyalopterus*

*pruni*) and the like; stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*) and the like; whiteflies (Aleyrodidae) such as greenhouse whitefly (*Trialeurodes vaporariorum*), sweetpotato whitefly (*Bemisia tabaci*), citrus whitefly (*Dialeurodes citri*), citrus spiny white fly (*Aleurocanthus spiniferus*) and the like; scales (Coccidae) such as California red scale (*Aonidiella aurantii*), San Jose scale (*Comstockaspis perniciosa*), citrus north scale (*Unaspis citri*), red wax scale (*Ceroplastes rubens*), cottony cushion scale (*Icerya purchasi*), Japanese mealybug (*Planococcus kraunhiae*), Cosmstock mealybug (*Pseudococcus longispinis*), white peach scale (*Pseudaulacaspis pentagona*) and the like; lace bugs (Tingidae); cimices such as *Cimex lectularius* and the like; psyllids (Psyllidae); etc.

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), bluegrass webworm (*Pediasia teterrellus*) and the like; owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., *Helicoverpa* spp. and the like; white butterflies (Pieridae) such as common white (*Pieris rapae*) and the like; tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana* fasciata), smaller tea tortrix (*Adoxophyes honmai.*), oriental tea tortrix (*Homona magnanima*), apple tortrix (*Archips fuscocupreanus*), codling moth (*Cydia pomonella*) and the like; leafblotch miners (Gracillariidae) such as tea leafroller (*Caloptilia theivora*), apple leafminer (*Phyllonorycter ringoneella*) and the like; Carposinidae such as peach fruit moth (*Carposina niponensis*) and the like; lyonetiid moths (Lyonetiidae) such as *Lyonetia* spp. and the like; tussock moths (Lymantriidae) such as *Lymantria* spp., *Euproctis* spp. and the like; yponomeutid moths (Yponomeutidae) such as diamondback (*Plutella xylostella*) and the like; gelechiid moths (Gelechiidae) such as pink bollworm (*Pectinophora gossypiella*), potato tubeworm (*Phthorimaea operculella*) and the like; tiger moths and allies (Arctiidae) such as fall webworm (*Hyphantria cunea*) and the like; tineid moths (Tineidae) such as casemaking clothes moth (*Tinea translucens*), webbing clothes moth (*Tineola bisselliella*) and the like; etc.

Thysanoptera:

Thrips (Thripidae) such as yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*) and the like, etc.

Diptera:

Culices such as common mosquito (*Culex pipiens pallens*), *Culex tritaeniorhynchus, Culex quinquefasciatus* and the like; *Aedes* spp. such as yellow fever mosquito (*Aedes aegypti*), Asian tiger mosquito (*Aedes albopictus*) and the like; *Anopheles* spp. such as *Anopheles sinensis* and the like; chironomids (Chironomidae); house flies (Muscidae) such as *Musca domestica, Muscina stabulans* and the like; blow flies (Calliphoridae); flesh flies (Sarcophagidae); little house flies (Fanniidae); anthomyiid flies (Anthomyiidae) such as seed-corn fly (*Delia platura*), onion fly (*Delia antiqua*) and the like; leafminer flies (Agromyzidae) such as rice leafminer (*Agromyza oryzae*), little rice leafminer (*Hydrellia griseola*), tomato leafminer (*Liriomyza sativae*), legume leafminer (*Liriomyza trifolii*), garden pea leafminer (*Chromatomyia horticola*) and the like; gout flies (Chloropidae) such as rice stem maggot (*Chlorops oryzae*) and the like; fruit flies (Tephritidae) such as melon fly (*Dacus cucurbitae*), Meditteranean fruit fly (*Ceratitis capitata*) and the like; Drosophilidae; humpbacked flies (Phoridae) such as *Megaselia spiracularis* and the like; moth flies (Psychodidae) such as *Clogmia albipunctata* and the like; Simuliidae; Tabanidae such as horsefly (*Tabanus trigonus*) and the like; stable flies, etc.

Coleoptera:

Corn root worms (*Diabrotica* spp.) such as Western corn root worm (*Diabrotica virgifera* virgifera), Southern corn root worm (*Diabrotica undecimpunctata howardi*) and the like; scarabs (Scarabaeidae) such as cupreous chafer (*Anomala cuprea*), soybean beetle (*Anomala rufocuprea*), Japanese beetle (*Popillia japonica*) and the like; weevils such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), hunting billbug (*Sphenophorus venatus*) and the like; darkling beetles (Tenebrionidae) such as yellow mealworm (*Tenebrio molitor*), red flour beetle (*Tribolium castaneum*) and the like; leaf beetles (Chrysomelidae) such as rice leaf beetle (*Oulema oryzae*), cucurbit leaf beetle (*Aulacophora femoralis*), striped flea beetle (*Phyllotreta striolata*), Colorado potato beetle (*Leptinotarsa decemlineata*) and the like; dermestid beetles (Dermestidae) such as varied carper beetle (*Anthrenus verbasci*), hide beetle (Dermestes maculates) and the like; deathwatch beetles (Anobiidae) such as cigarette beetle (*Lasioderma serricorne*) and the like; *Epilachna* such as Twenty-eight-spotted ladybird (*Epilachna vigintioctopunctata*) and the like; bark beetles (Scolytidae) such as powder-post beetle (*Lyctus brunneus*), pine shoot beetle (*Tomicus piniperda*) and the like; false powder-post beetles (Bostrychidae); spider beetles (Ptinidae); longhorn beetles (Cerambycidae) such as white-spotted longicorn beetle (*Anoplophora malasiaca*) and the like; click beetles (*Agriotes* spp.); *Paederus fuscipens*, etc.

Orthoptera:

Asiatic locust (*Locusta migratoria*), African mole cricket (*Gryllotalpa africana*), rice grasshopper (*Oxya yezoensis*), rice grasshopper (*Oxya japonica*), Gryllidae, etc.

Shiphonaptera:

Cat flea (*Ctenocephalides felis*), dog flea (*Ctenocephalides canis*), human flea (*Pulex irritans*), oriental rat flea (*Xenopsylla cheopis*), etc.

Anoplura:

Human body louse (*Pediculus humanus corporis*), crab louse (*Phthirus pubis*), short-nosed cattle louse (*Haematopinus eurysternus*), sheep louse (*Dalmalinia ovis*), hog louse (*Haematopinus suis*), etc.

Hymenoptera:

Ants (Formicidae) such as pharaoh ant (*Monomorium pharaosis*), negro ant (Formica fusca japonica), black house ant (*Ochetellus glaber*), *Pristomyrmex pungens, Pheidole noda*, leaf-cutting ant (*Acromyrmex* spp.), fire ant (*Solenopsis* spp.) and the like; hornets (Vespidae); bethylid wasps (Betylidae); sawflies (Tenthredinidae) such as cabbage sawfly (*Athalia rosae*), *Athalia japonica* and the like, etc.

Blattodea:

German cockroach (*Blattella germanica*), smokybrown cockroach (*Periplaneta fuliginosa*), American cockroach (*Periplaneta americana*), *Periplaneta brunnea*, oriental cockroach (*Blatta orientalis*) and the like;

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), *Oligonychus* spp. and the like; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagrans*), *Eriophyes chibaensis*, apple rust mite (*Aculus schlechtendali*) and the like; tarosonemid mites (Tarsonemidae) such as broad mite (*Polyphagotarsonemus latus*) and the like; false spider mites (Tenuipalpidae) such as *Brevipalpus phoenicis* and the like; Tuckerellidae; ticks (Ixodidae) such as *Haemaphysalis longicornis, Haemaphysalis flava, Dermacentor taiwanicus, Ixodes ovatus, Ixodes persulcatus*, black legged tick (*Ixodes scapularis*), *Boophilus microplus, Rhipicephalus sanguineus* and the like; acarid mites (Acaridae) such as mold mite (*Tyrophagus putrescentiae*), *Tyrophagus similis* and the like; house dust mites (*Pyroglyphidae*) such as *Dermatophagoides farinae*, and *Dermatophagoides ptrenyssnus* and the like; cheyletide mites (Cheyletidae) such as *Cheyletus eruditus, Cheyletus malaccensis, Cheyletus moorei* and the like; parasitoid mites (Dermanyssidae) such as tropical rat mite (*Ornithonyssus bacoti*), northern fowl mite (*Ornithonyssus sylviarum*), poultry red mite (*Dermanyssus gallinae*) and the like; chiggers (Trombiculidae) such as *Leptotrombidium akamushi* and the like; spiders (Araneae) such as Japanese foliage spider (*Chiracanthium japonicum*), redback spider (*Latrodectus hasseltii*) and the like, etc.

The arthropod pest control composition of the present invention can be used in agricultural lands for cultivating "crops" listed below, and the like.

Agricultural crops: corn, rice, wheat, barley, rye, oat, sorghum, cotton, soybean, peanut, sarrazin, sugar beet, rapeseed, sunflower, sugar cane, tobacco, etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables, (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid, etc.;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, macadamia nut etc.), berry fruits (blueberry, cranberry, blackberry, raspberry etc.), grape, persimmon, olive, loquat, banana, coffee, date, coconut palm, oil palm, etc.;

Trees other than fruit trees: tea, mulberry, flowering trees (rhododendron, camellia, hydrangea, sasanqua, Japanese star anise, Japanese Cherry, tulip tree, Crape myrtle, fragrant orange-colored olive, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, Japanese horse-chestnut, etc.), Sweet viburnum, Largeleaf podocarp, Japanese cedar, Hinoki cypress, croton, Japanese Spindle, Chinese hawthorn, etc.

Lawn: zoysia (Japanese lawn grass, mascarene grass, etc.), Bermuda grass (Cynodon dactylon, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.;

Others: flowering herbs (rose, carnation, chrysanthemum, *Eustoma grandiflorum* Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsettia, gladiolus, cattleya, daisy, cymbidium, begonia, etc.), biofuel plants (jatropha, safflower, Camelina alyssum, switch grass, Miscanthus, reed Canary grass, Great reed, kenaf, cassava, willow, algae, etc.), ornamental foliage plants, etc.

The above described "crops" include genetically modified crops.

EXAMPLES

The present invention will be explained further in detail by Production Examples, Reference Production Examples and Test Examples below, but the present invention is not limited to them.

First, Production Examples are shown for production of the present compound.

Production Example 1

A mixture of 2.3 g of 2-amino-4-(trifluoromethyl)-benzenethiol hydrochloride, 1.25 g of 3-fluoroisonicotinaldehyde, 1.29 g of N-ethyldiisopropylamine and 10 ml of DMSO was stirred for 5 hours at 170° C. The reaction mixture was cooled down to room temperature. To the reaction mixture was added water, and the resultant mixture was extracted with ethyl acetate twice. The combined organic layers were washed with water and saturated saline, dried over magnesium sulfate, then, concentrated under reduced pressure. The residue was subjected to silica gel column chromatography, to obtain 1.79 g of 2-(3-fluoropyridin-4-yl)-5-(trifluoromethyl)benzothiazole (hereinafter, referred to as the present compound 1).

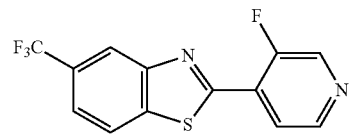

The Present Compound 1

$^1$H-NMR (CDCl$_3$) δ: 8.72 (d, J=2.4 Hz, 1H), 8.65-8.63 (m, 1H), 8.47-8.45 (m, 1H), 8.34-8.31 (m, 1H), 8.12 (d, J=8.5 Hz, 1H), 7.73 (dd, J=8.5, 1.7 Hz, 1H)

Production Example 2

2-(3-chloropyridin-4-yl)-5-(trifluoromethyl)benzothiazole (hereinafter, referred to as the present compound 2) was obtained in the same manner as in Production Example 1, excepting that 3-chloroisonicotinaldehyde was used instead of 3-fluoroisonicotinaldehyde.

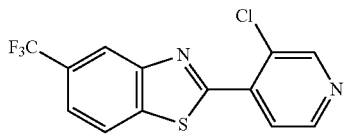 [SMILES: Fc1cnccc1-c1nc2cc(C(F)(F)F)ccc2s1]

The Present Compound 2

¹H-NMR (CDCl₃) δ: 8.82 (s, 1H), 8.68 (d, J=5.1 Hz, 1H), 8.47-8.45 (m, 1H), 8.29 (d, J=5.1 Hz, 1H), 8.12 (d, J=8.5 Hz, 1H), 7.73 (dd, J=8.5, 1.2 Hz, 1H)

Production Example 3

To a mixture of 0.50 g of 2-(3-chloropyridin-4-yl)-5-(trifluoromethyl)benzothiazole and 5 ml of chloroform was added 0.51 g of 70% m-chloroperbenzoic acid under ice cool. This mixture was stirred at room temperature for 6 hours. The reaction mixture was diluted with chloroform, and washed with a 5% sodium hydroxide aqueous solution and saturated saline sequentially. The organic layer was dried over magnesium sulfate, then, concentrated under reduced pressure. The residue was subjected to silica gel column chromatography, to obtain 0.43 g of 2-(3-chloro-1-oxypyridin-4-yl)-5-(trifluoromethyl)benzothiazole (hereinafter, referred to as the present compound 3).

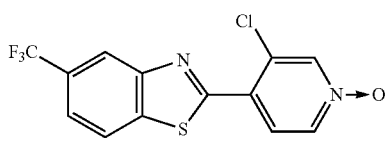 [SMILES: [O-][n+]1ccc(-c2nc3cc(C(F)(F)F)ccc3s2)c(Cl)c1]

The Present Compound 3

¹H-NMR (CDCl₃) δ: 8.45 (d, J=7.1 Hz, 1H), 8.41-8.39 (m, 2H), 8.21 (dd, J=7.1, 1.7 Hz, 1H), 8.10 (d, J=8.3 Hz, 1H), 7.74-7.71 (m, 1H)

Production Example 4

A mixture of 0.28 g of 2-(3-fluoropyridin-4-yl)-5-(trifluoromethyl)benzothiazole, 0.28 g of potassium carbonate and 3 ml of methanol was refluxed with heating for 1.5 hours. The reaction mixture was cooled down to room temperature. To the reaction mixture was added water, and the resultant mixture was extracted with ethyl acetate twice. The combined organic layers were washed with water and saturated saline, dried over magnesium sulfate, then, concentrated under reduced pressure. The residue was subjected to silica gel column chromatography, to obtain 2-(3-methoxypyridin-4-yl)-5-(trifluoromethyl)benzothiazole (hereinafter, referred to as the present compound 4).

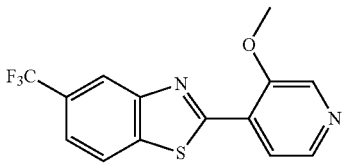 [SMILES: COc1cnccc1-c1nc2cc(C(F)(F)F)ccc2s1]

The Present Compound 4

¹H-NMR (CDCl₃) δ: 8.58 (s, 1H), 8.47 (d, J=4.9 Hz, 1H), 8.42-8.40 (m, 1H), 8.37 (d, J=4.9 Hz, 1H), 8.09-8.06 (m, 1H), 7.69-7.65 (m, 1H), 4.21 (s, 3H)

Production Example 5

A mixture of 0.30 g of 2-(3-fluoropyridin-4-yl)-5-(trifluoromethyl)benzothiazole, 0.14 g of methylmercaptan sodium salt and 3 ml of DMF was stirred at room temperature for 20 minutes. To the reaction mixture was added water, and the resultant mixture was extracted with ethyl acetate three times. The combined organic layers were washed with water and saturated saline, dried over magnesium sulfate, then, concentrated under reduced pressure. The residue was subjected to silica gel column chromatography, to obtain 2-[3-(methylthio)pyridin-4-yl]-5-(trifluoromethyl)benzothiazole (hereinafter, referred to as the present compound 5).

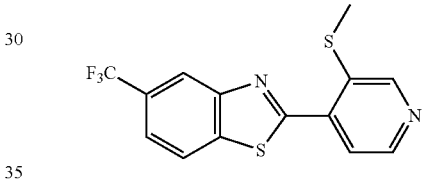

The Present Compound 5

¹H-NMR (CDCl₃) δ: 8.76-8.75 (m, 1H), 8.58 (d, J=5.1 Hz, 1H), 8.46-8.44 (m, 1H), 8.10-8.07 (m, 1H), 7.91 (dd, J=5.1, 0.7 Hz, 1H), 7.73-7.69 (m, 1H), 2.61 (s, 3H)

Production Example 6

2-[3-(ethylthio)pyridin-4-yl]-5-(trifluoromethyl)benzothiazole (hereinafter, referred to as the present compound 6) was obtained in the same manner as in Production Example 5, excepting that an ethylmercaptan sodium salt was used instead of the methylmercaptan sodium salt.

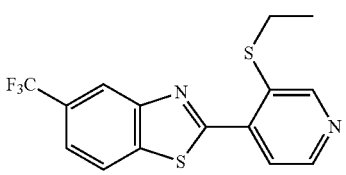 [SMILES: CCSc1cnccc1-c1nc2cc(C(F)(F)F)ccc2s1]

The Present Compound 6

¹H-NMR (CDCl₃) δ: 8.72 (s, 1H), 8.56 (d, J=5.1 Hz, 1H), 8.23-8.21 (m, 1H), 8.02 (d, J=5.1 Hz, 1H), 7.77-7.70 (m, 2H), 3.19 (q, J=7.4 Hz, 2H), 1.48 (t, J=7.4 Hz, 3H)

Production Example 7

To a mixture of 0.65 g of 2-[3-(ethylthio)pyridin-4-yl]-5-(trifluoromethyl)benzothiazole and 5 ml of chloroform was added 0.66 g of 70% m-chloroperbenzoic acid under ice cool.

This mixture was stirred at 0° C. for 1 hour. The reaction mixture was diluted with chloroform, and washed with a 5% sodium hydroxide aqueous solution and saturated saline sequentially. The organic layer was dried over magnesium sulfate, then, concentrated under reduced pressure. The residue was subjected to silica gel column chromatography, to obtain 0.19 g of 2-[3-(ethanesulfonyl)pyridin-4-yl]-5-(trifluoromethyl)benzothiazole (hereinafter, referred to as the present compound 7) and 0.35 g of 2-[3-(ethanesulfinyl)pyridin-4-yl]-5-(trifluoromethyl)benzothiazole (hereinafter, referred to as the present compound 8).

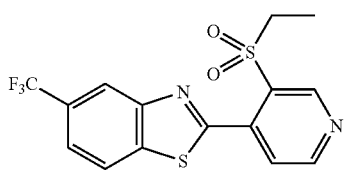 [SMILES: CCS(=O)(=O)c1cnccc1-c1nc2cc(C(F)(F)F)ccc2s1]

The Present Compound 7

¹H-NMR (CDCl₃) δ: 9.40 (s, 1H), 9.04 (d, J=4.9 Hz, 1H), 8.38-8.36 (m, 1H), 8.12 (d, J=8.5 Hz, 1H), 7.77-7.74 (m, 1H), 7.65-7.63 (m, 1H), 3.82 (q, J=7.5 Hz, 2H), 1.42 (t, J=7.4 Hz, 3H)

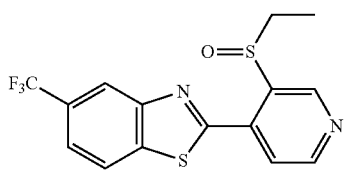 [SMILES: CCS(=O)c1cnccc1-c1nc2cc(C(F)(F)F)ccc2s1]

The Present Compound 8

¹H-NMR (CDCl₃) δ: 9.46 (s, 1H), 8.93 (d, J=5.1 Hz, 1H), 8.38-8.37 (m, 1H), 8.13 (d, J=8.5 Hz, 1H), 7.79-7.75 (m, 2H), 3.54 (dq, J=13.2, 7.4 Hz, 1H), 3.13 (dq, J=13.2, 7.4 Hz, 1H), 1.50 (t, J=7.4 Hz, 3H)

Production Example 8

A mixture of 0.90 g of 3-amino-5-(trifluoromethyl)-pyridine-2-thiol, 0.58 g of 3-fluoroisonicotinaldehyde and 5 ml of DMSO was stirred at 170° C. for 2 hours. The reaction mixture was cooled down to room temperature, then, to the reaction mixture was added water, and the resultant mixture was extracted with ethyl acetate twice. The combined organic layers were washed with water and saturated saline, dried over magnesium sulfate, then, concentrated under reduced pressure. The residue was subjected to silica gel column chromatography, to obtain 0.55 g of 2-(3-fluoropyridin-4-yl)-6-(trifluoromethyl)thiazolo[5,4-b]pyridine (hereinafter, referred to as the present compound 9).

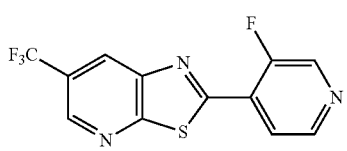 [SMILES: Fc1cnccc1-c1nc2cc(C(F)(F)F)cnc2s1]

The Present Compound 9

¹H-NMR (CDCl₃) δ: 8.96-8.94 (m, 1H), 8.76 (d, J=2.4 Hz, 1H), 8.67 (dd, J=5.1, 1.0 Hz, 1H), 8.65-8.64 (m, 1H), 8.32-8.28 (m, 1H)

Production Example 9

2-(3-chloropyridin-4-yl)-6-(trifluoromethyl)thiazolo[5,4-b]pyridine (hereinafter, referred to as the present compound 10) was obtained in the same manner as in Production Example 8, excepting that 3-chloroisonicotinaldehyde was used instead of 3-fluoroisonicotinaldehyde.

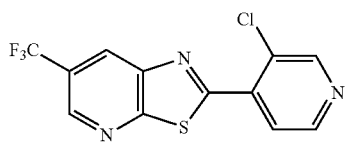

The Present Compound 10

¹H-NMR (CDCl₃) δ: 8.96-8.95 (m, 1H), 8.85 (s, 1H), 8.71 (d, J=5.1 Hz, 1H), 8.65-8.64 (m, 1H), 8.25 (d, J=5.1 Hz, 1H)

Production Example 10

A mixture of 0.29 g of 2-(3-fluoropyridin-4-yl)-6-(trifluoromethyl)thiazolo[5,4-b]pyridine, 0.15 g of potassium carbonate and 6 ml of ethanol was refluxed with heating for 8 hours. The reaction mixture was cooled down to room temperature. To the reaction mixture was added water, and the resultant mixture was extracted with ethyl acetate twice. The combined organic layers were washed with saturated saline, dried over magnesium sulfate, then, concentrated under reduced pressure. The residue was subjected to silica gel column chromatography, to obtain 2-(3-ethoxypyridin-4-yl)-6-(trifluoromethyl)thiazolo[5,4-b]pyridine (hereinafter, referred to as the present compound 11).

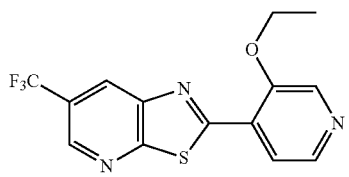 [SMILES: CCOc1cnccc1-c1nc2cc(C(F)(F)F)cnc2s1]

The Present Compound 11

¹H-NMR (CDCl₃) δ: 8.91-8.89 (m, 1H), 8.59-8.57 (m, 1H), 8.57 (s, 1H), 8.46 (d, J=4.9 Hz, 1H), 8.35 (d, J=4.9 Hz, 1H), 4.47 (q, J=7.0 Hz, 2H), 1.70 (t, J=7.0 Hz, 3H)

Production Example 11

2-(3-methoxypyridin-4-yl)-6-(trifluoromethyl)thiazolo[5,4-b]pyridine (hereinafter, referred to as the present compound 12) was obtained in the same manner as in Production Example 10, excepting that methanol was used instead of ethanol.

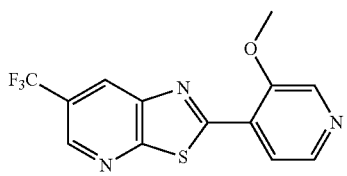 [SMILES: COc1cnccc1-c1nc2cc(C(F)(F)F)cnc2s1]

The Present Compound 12

$^1$H-NMR (CDCl$_3$) δ: 8.91-8.90 (m, 1H), 8.61 (s, 1H), 8.60-8.58 (m, 1H), 8.49 (d, J=5.1 Hz, 1H), 8.35 (d, J=5.0 Hz, 1H), 4.23 (s, 3H)

Production Example 12

To a mixture of 51 mg of sodium hydride (60% dispersion in mineral oil) and 2 ml of DMF was added at room temperature a mixture of 0.10 g of 2,2-difluoro-ethanol and 1 ml of DMF. This mixture was stirred at room temperature for 15 minutes, then, cooled with ice. Next, to this was added a mixture of 0.29 g of 2-(3-fluoropyridin-4-yl)-6-(trifluoromethyl)thiazolo[5,4-b]pyridine and 10 ml of DMF, and the resultant mixture was stirred for 0.5 hours under ice cool, further for 0.5 hours at room temperature. To the reaction mixture was added water, and the resultant mixture was extracted with ethyl acetate. The organic layer was washed with saturated saline, dried over magnesium sulfate, then, concentrated under reduced pressure. The residue was subjected to silica gel column chromatography, to obtain 0.27 g of 2-[3-(2,2-difluoroethoxy)pyridin-4-yl]-6-(trifluoromethyl)thiazolo[5,4-b]pyridine (hereinafter, referred to as the present compound 13).

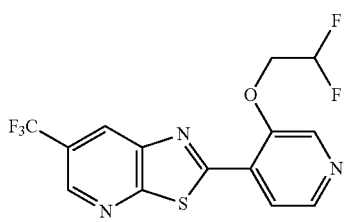 [SMILES: FC(F)COc1cnccc1-c1nc2cc(C(F)(F)F)cnc2s1]

The Present Compound 13

$^1$H-NMR (CDCl$_3$) δ: 8.94-8.92 (m, 1H), 8.62-8.60 (m, 1H), 8.58-8.56 (m, 2H), 8.40 (d, J=5.1 Hz, 1H), 6.35 (tt, J=54.6, 3.9 Hz, 1H), 4.59 (td, J=12.7, 3.9 Hz, 2H)

Production Example 13

A mixture of 0.20 g of 2-(3-fluoropyridin-4-yl)-6-(trifluoromethyl)thiazolo[5,4-b]pyridine, 47 mg of methylmercaptan sodium salt and 6 ml of DMF was stirred for 1 hour under ice cool. To this mixture was added 47 mg of methylmercaptan sodium salt, and the resultant mixture was stirred further for 1 hour under ice cool. To the reaction mixture was added water, and the resultant mixture was extracted with ethyl acetate twice. The combined organic layers were washed with water and saturated saline, dried over magnesium sulfate, then, concentrated under reduced pressure. The residue was subjected to silica gel column chromatography, to obtain 0.19 g of 2-[3-(methylthio)pyridin-4-yl]-6-(trifluoromethyl)thiazolo[5,4-b]pyridine (hereinafter, referred to as the present compound 14).

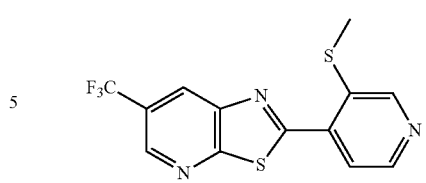

The Present Compound 14

$^1$H-NMR (CDCl$_3$) δ: 8.93-8.91 (m, 1H), 8.78 (s, 1H), 8.64-8.63 (m, 1H), 8.61 (d, J=5.1 Hz, 1H), 7.91-7.89 (m, 1H), 2.62 (s, 3H)

Production Example 14

A mixture of 0.90 g of 2-(3-fluoropyridin-4-yl)-6-(trifluoromethyl)thiazolo[5,4-b]pyridine, 0.32 g of ethylmercaptan sodium salt and 12 ml of DMF was stirred for 1 hour under ice cool. To the reaction mixture was added water, and the deposited solid was collected by filtration. This solid was washed with water, then, dissolved in ethyl acetate. The organic layer was washed with saturated saline, dried over magnesium sulfate, then, concentrated under reduced pressure. The residue was subjected to silica gel column chromatography, to obtain 0.89 g of 2-[3-(ethylthio)pyridin-4-yl]-6-(trifluoromethyl)thiazolo[5,4-b]pyridine (hereinafter, referred to as the present compound 15).

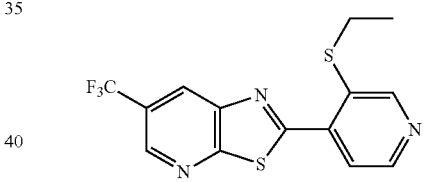

The Present Compound 15

$^1$H-NMR (CDCl$_3$) δ: 8.93-8.92 (m, 1H), 8.85-8.84 (m, 1H), 8.64 (d, J=5.1 Hz, 1H), 8.63-8.62 (m, 1H), 8.05-8.04 (m, 1H), 3.05 (q, J=7.4 Hz, 2H), 1.36 (t, J=7.4 Hz, 3H)

Production Example 15

To a mixture of 0.62 g of 2-[3-(ethylthio)pyridin-4-yl]-6-(trifluoromethyl)thiazolo[5,4-b]pyridine and 5 ml of chloroform was added 0.66 g of 65% m-chloroperbenzoic acid under ice cool. This mixture was stirred at 0° C. for 1 hour. The reaction mixture was diluted with chloroform, and washed with a 5% sodium hydroxide aqueous solution and saturated saline sequentially. The organic layer was dried over magnesium sulfate, then, concentrated under reduced pressure. The residue was subjected to silica gel column chromatography, to obtain 0.27 g of 2-[3-(ethanesulfonyl)pyridin-4-yl]-6-(trifluoromethyl)thiazolo[5,4-b]pyridine (hereinafter, referred to as the present compound 16) and 0.28 g of 2-[3-(ethanesulfinyl)pyridin-4-yl]-6-(trifluoromethyl)thiazolo[5,4-b]pyridine (hereinafter, referred to as the present compound 17).

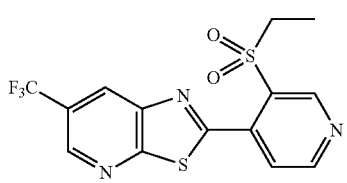 [SMILES: CCS(=O)(=O)c1cnccc1-c1nc2cc(C(F)(F)F)cnc2s1]

The Present Compound 16
$^1$H-NMR (CDCl$_3$) δ: 9.41 (s, 1H), 9.07 (d, J=4.9 Hz, 1H), 8.97-8.96 (m, 1H), 8.58-8.56 (m, 1H), 7.65 (d, J=5.0 Hz, 1H), 3.77 (q, J=7.5 Hz, 2H), 1.43 (t, J=7.4 Hz, 3H)

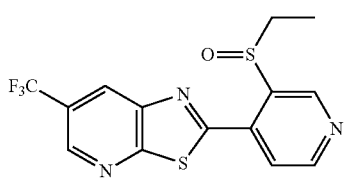

The Present Compound 17
$^1$H-NMR (CDCl$_3$) δ: 9.49 (s, 1H), 8.98-8.96 (m, 2H), 8.59-8.57 (m, 1H), 7.82-7.80 (m, 1H), 3.51 (dq, J=13.2, 7.5 Hz, 1H), 3.12 (dq, J=13.2, 7.4 Hz, 1H), 1.49 (t, J=7.4 Hz, 3H)

Production Example 16

To a mixture of 1.56 g of potassium ferricyanide and 4 ml of water, a mixture of 0.50 g of 3-chloro-N-[(4-trifluoromethyl)phenyl]thioisonicotinamide, 0.41 g of sodium hydroxide and 6 ml of water was dropped at 60° C. over a period of 45 minutes. Thereafter, this mixture was stirred at 60° C. for 2 hours. Next, 1.02 g of potassium carbonate was added, and the resultant mixture was stirred at 50° C. further for 1 hour. The reaction mixture was cooled down to room temperature, then, the reaction mixture was extracted with diethyl ether twice. The combined organic layers were washed with saturated saline, dried over magnesium sulfate, then, concentrated under reduced pressure. The residue was subjected to silica gel column chromatography, to obtain 60 mg of 2-(3-chloropyridin-4-yl)-6-(trifluoromethyl)benzothiazole (hereinafter, referred to as the present compound 18).

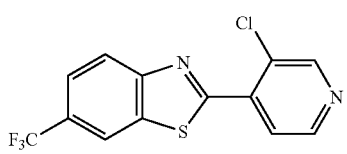 [SMILES: FC(F)(F)c1ccc2nc(-c3ccncc3Cl)sc2c1]

The Present Compound 18
$^1$H-NMR (CDCl$_3$) δ: 8.81 (s, 1H), 8.67 (d, J=5.1 Hz, 1H), 8.30-8.28 (m, 2H), 8.28-8.24 (m, 1H), 7.82-7.79 (m, 1H)

Production Example 17

To a mixture of 2.77 g of potassium ferricyanide and 20 ml of water, a mixture of 0.70 g of 3-chloro-N-[(4-trifluoromethoxy)phenyl]thioisonicotinamide, 0.67 g of sodium hydroxide, 5.6 ml of water and 8 ml of ethanol was dropped at 90° C. over a period of 20 minutes. Thereafter, this mixture was stirred at 90° C. for 1 hour. The reaction mixture was cooled down to room temperature. The reaction mixture was extracted with diethyl ether twice. The combined organic layers were washed with saturated saline, dried over magnesium sulfate, then, concentrated under reduced pressure. The residue was subjected to silica gel column chromatography, to obtain 0.18 g of 2-(3-chloropyridin-4-yl)-6-(trifluoromethoxy)benzothiazole (hereinafter, referred to as the present compound 19).

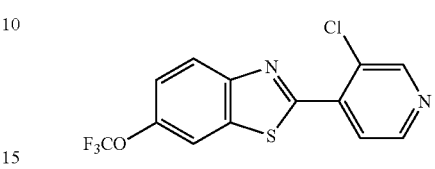

The Present Compound 19
$^1$H-NMR (CDCl$_3$) δ: 8.81 (s, 1H), 8.67-8.65 (m, 1H), 8.26 (d, J=5.1 Hz, 1H), 8.18 (d, J=8.8 Hz, 1H), 7.87-7.86 (m, 1H), 7.47-7.43 (m, 1H)

Next, Reference Production Examples are shown for production of production intermediates for the above-described inventive compounds.

Reference Production Example 1

To a mixture of 9.84 g of 2-hydroxy-5-(trifluoromethyl)pyridine and 40 ml of concentrated sulfuric acid, 10.9 g of 70% nitric acid was dropped at 80° C. This mixture was stirred at 80° C. for 1 hour. The reaction mixture was cooled down to room temperature, then, the reaction mixture was poured into ice water. The deposited solid was collected by filtration. This solid was washed with ice water, then, dissolved in ethyl acetate, and washed with saturated saline. The organic layer was dried over magnesium sulfate, then, concentrated under reduced pressure, to obtain 5.22 g of 2-hydroxy-3-nitro-5-(trifluoromethyl)pyridine.

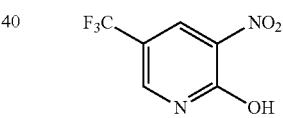

$^1$H-NMR (DMSO-d$_6$) δ: 13.54 (br s, 1H), 8.67 (d, J=2.7 Hz, 1H), 8.48-8.45 (m, 1H)

A mixture of 5.22 g of 2-hydroxy-3-nitro-5-(trifluoromethyl)pyridine, 4.2 g of phosphorus oxychloride and 2.0 g of quinoline was refluxed with heating for 5.5 hours. The reaction mixture was cooled down to room temperature, then, the reaction mixture was poured into ice water. This mixture was neutralized with a sodium hydroxide aqueous solution, then, the mixture was extracted with ethyl acetate twice. The combined organic layers were washed with water and saturated saline, dried over magnesium sulfate, then, concentrated under reduced pressure. The residue was subjected to silica gel column chromatography, to obtain 4.88 g of 2-chloro3-nitro-5-(trifluoromethyl)pyridine.

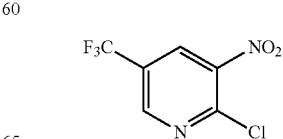

$^1$H-NMR (CDCl$_3$) δ: 8.91-8.87 (m, 1H), 8.48-8.44 (m, 1H)

A mixture of 4.88 g of 2-chloro3-nitro-5-(trifluoromethyl)pyridine, 1.81 g of thiourea and 40 ml of ethanol was stirred at 50° C. for 5.5 hours. The reaction mixture was cooled down to room temperature, then, concentrated under reduced pressure. To the residue was added 24 ml of water and a mixture of 2.8 g of sodium hydroxide and 6 ml of water, and this was stirred at room temperature for 1.5 hours. The reaction mixture was washed with diethyl ether, then, acetic acid was added. This was cooled with ice, and the deposited solid was collected by filtration. This solid was dried under reduced pressure, to obtain 3.84 g of 3-nitro-5-(trifluoromethyl)pyridine-2-thiol.

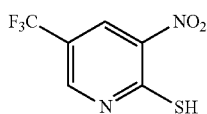

$^1$H-NMR (DMSO-$d_6$) δ: 8.53 (d, J=2.2 Hz, 1H), 8.38-8.36 (m, 1H)

To a mixture of 2.87 g of iron, 10 ml of acetic acid and 10 ml of water was added a mixture of 3.84 g of 3-nitro-5-(trifluoromethyl)pyridine-2-thiol and 10 ml of ethyl acetate at 70° C. over a period of 10 minutes. The reaction mixture was cooled down to room temperature, then, to the reaction mixture was added water, and the resultant mixture was extracted with ethyl acetate twice. The combined organic layers were washed with water and saturated saline, dried over magnesium sulfate, then, concentrated under reduced pressure to obtain 3.1 g of 3-amino-5-(trifluoromethyl)pyridine-2-thiol.

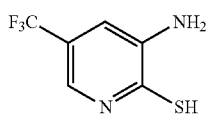

$^1$H-NMR (DMSO-$d_6$) δ: 13.85 (br s, 1H), 7.43-7.40 (m, 1H), 6.83-6.82 (m, 1H), 6.16 (br s, 2H)

Reference Production Example 2

A mixture of 1.53 g of 4-trifluoromethylaniline, 1.50 g of 3-chloroisonicotic acid, 2.37 g of 1-ethyl-3-(3-dimethylaminopropyl)carbodiimide hydrochloride (hereinafter, referred to as WSC) and 10 ml of pyridine was stirred at 60° C. for 1 hour. The reaction mixture was cooled down to room temperature. To the reaction mixture, water was poured, and the resultant mixture was extracted with ethyl acetate twice. The combined organic layers were washed with water and saturated saline, dried over magnesium sulfate, then, concentrated under reduced pressure. The residue was subjected to silica gel column chromatography, to obtain 1.59 g of 3-chloro-N-[(4-trifluoromethyl)phenyl]isonicotinamide.

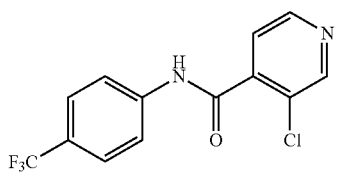 [SMILES: O=C(Nc1ccc(C(F)(F)F)cc1)c1ccncc1Cl]

$^1$H-NMR (CDCl$_3$) δ: 8.73 (s, 1H), 8.66 (d, J=4.9 Hz, 1H), 8.20 (br s, 1H), 7.78 (d, J=8.3 Hz, 2H), 7.70-7.64 (m, 3H)

A mixture of 1.59 g of 3-chloro-N-[(4-trifluoromethyl)phenyl]isonicotinamide, 1.07 g of 2,4-bis(4-methoxyphenyl)-1,3-dithia-2,4-diphosphetane-2,4-disulfide (hereinafter, referred to as Lawesson's reagent) and 7 ml of toluene was refluxed with heating for 3.5 hours. The reaction mixture was cooled down to room temperature, then, concentrated under reduced pressure. The residue was subjected to silica gel column chromatography, to obtain 1.47 g of 3-chloro-N-[(4-trifluoromethyl)phenyl]thioisonicotinamide.

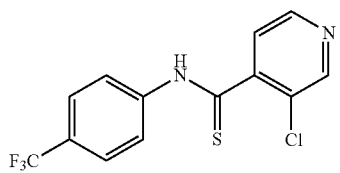 [SMILES: FC(F)(F)c1ccc(NC(=S)c2ccncc2Cl)cc1]

$^1$H-NMR (CDCl$_3$) δ: 9.41 (br s, 1H), 8.60 (s, 1H), 8.54 (d, J=5.0 Hz, 1H), 8.03 (d, J=8.5 Hz, 2H), 7.73 (d, J=8.6 Hz, 2H), 7.51 (d, J=5.0 Hz, 1H)

Reference Production Example 3

A mixture of 1.69 g of 4-trifluoromethoxyaniline, 1.50 g of 3-chloroisonicotic acid, 2.37 g of WSC and 10 ml of pyridine was stirred at 60° C. for 1.3 hours. The reaction mixture was cooled down to room temperature. The reaction mixture was poured into water. This mixture was extracted with ethyl acetate twice. The combined organic layers were washed with water and saturated saline, dried over magnesium sulfate, then, concentrated under reduced pressure. The residue was subjected to silica gel column chromatography, to obtain 2.87 g of 3-chloro-N-[(4-trifluoromethoxy)phenyl]isonicotinamide.

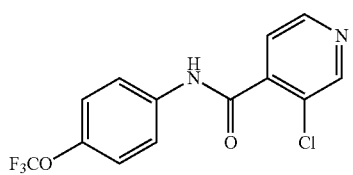

$^1$H-NMR (CDCl$_3$) 8.71 (s, 1H), 8.63 (d, J=5.1 Hz, 1H), 8.14 (br s, 1H), 7.68 (d, J=8.8 Hz, 2H), 7.65 (d, J=5.1 Hz, 1H), 7.26 (d, J=8.8 Hz, 2H)

A mixture of 0.62 g of 3-chloro-N-[(4-trifluoromethoxy)phenyl]isonicotinamide, 0.40 g of Lawesson's reagent and 5 ml of toluene was refluxed with heating for 4 hours. The reaction mixture was cooled down to room temperature, then, concentrated under reduced pressure. The residue was subjected to silica gel column chromatography, to obtain 0.56 g of 3-chloro-N-[(4-trifluoromethoxy)phenyl]thioisonicotineamide.

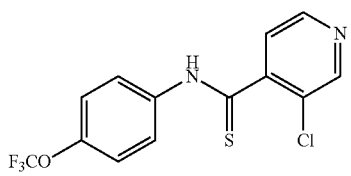 [SMILES: FC(F)(F)Oc1ccc(NC(=S)c2ccncc2Cl)cc1]

$^1$H-NMR (CDCl$_3$) δ: 8.94 (br s, 1H), 8.67 (s, 1H), 8.58 (d, J=5.0 Hz, 1H), 7.89 (d, J=8.9 Hz, 2H), 7.53 (d, J=5.1 Hz, 2H), 7.33 (d, J=8.9 Hz, 1H)

Next, Formulation Examples of the present compound are shown. Parts are by weight.

Formulation Example 1

Ten (10) parts of any one of the present compounds (1) to (19) described above was dissolved in a mixture of 35 parts of xylene and 35 parts of N,N-dimethylformamide, and 14 parts of polyoxyethylene styryl phenyl ether and 6 parts of calcium dodecylbenzenesulfonate were added, and mixed to obtain an emulsifiable concentrate.

Formulation Example 2

Four (4) parts of sodium laurylsulfate, 2 parts of calcium ligninsulfonate, 20 parts of a synthetic hydrous silicon oxide fine powder and 54 parts of diatomaceous earth were mixed, and 20 parts of any one of the present compounds (1) to (19) described above was added, and mixed to obtain a wettable powder.

Formulation Example 3

To 2 parts of any one of the present compounds (1) to (19) described above was added 1 part of a synthetic hydrous silicon oxide fine powder, 2 parts of calcium ligninsulfonate, 30 parts of bentonite and 65 parts of kaolin clay, and mixed. Then, to this mixture was added a suitable amount of water, the mixture was further stirred, granulated by a granulator, and dried under ventilation to obtain a granule.

Formulation Example 4

One part of any one of the present compounds (1) to (19) described above was dissolved in a suitable amount of acetone, and to this was added 5 parts of a synthetic hydrous silicon oxide fine powder, 0.3 parts of PAP and 93.7 parts of Fubasami clay, and sufficiently stirred to mix, and acetone was removed by distillation to obtain a powder.

Formulation Example 5

Thirty five (35) parts of a mixture (weight ratio 1:1) of polyoxyethylene alkyl ether sulfate ammonium salt and white carbon, 10 parts of any one of the present compounds (1) to (19) described above and 55 parts of water were mixed, and finely pulverized by a wet pulverization method to obtain a formulation.

Formulation Example 6

Zero point one (0.1) part of any one of the present compounds (1) to (19) described above was dissolved in 5 parts of xylene and 5 parts of trichloroethane, and this solution was mixed to 89.9 parts of deodorized kerosene, to obtain an oil solution.

Formulation Example 7

Ten (10) mg of any one of the present compounds (1) to (19) described above was dissolved in 0.5 ml of acetone, and 5 g of this solution was used to treat an animal solid feedstuff powder (breeding-propagation solid feedstuff powder CE-2, manufactured by CLEA Japan Inc.), and mixed uniformly. Then, acetone was evaporated to dryness, to obtain a poison bait.

Formulation Example 8

Zero point one (0.1) part of any one of the present compounds (1) to (19) described above and 49.9 parts of Neothiozole (Chuo Kasei Co. Ltd.) were charged in an aerosol can which was then equipped with an aerosol valve, then, 25 parts of dimethyl ether and 25 parts of LPG were filled in and vibration was applied, and an actuator was mounted to obtain an oil solution aerosol.

Formulation Example 9

Zero point six (0.6) parts of any one of the present compounds (1) to (19) described above, 0.01 part of BHT (2,6-di-tert-butyl-4-methylphenol), 5 parts of xylene, 3.39 parts of deodorized kerosene and 1 part of an emulsifier {Atmos 300 (registered trademark of Atmos Chemical)} were mixed and dissolved, and the resultant solution and 50 parts of distilled water were filled in an aerosol vessel which was then equipped with a valve, then, 40 parts of an injection agent (LPG) was filled under pressure through the valve, to obtain an aqueous aerosol.

Next, the arthropod pest control effect of the present compound is shown by test examples.

Test Example 1

The present compounds (1), (2), (4) to (12), (14) to (17) and (19) were formulated by the method in Formulation Example 5. This formulation was diluted with water so that the active ingredient concentration was 500 ppm, to prepare a diluted solution for test.

A cucumber seedling (first true leaf spreading stage) planted in a plastic cup was inoculated with about 30 *Aphis gossypii*, and left for 1 day. On this cucumber seedling, the above-described diluted solution for test (20 ml) was sprayed.

Six days after spraying, the insect number of living *Aphis gossypii* parasitic on the leaves of the cucumber was checked, and the control value was calculated according to the following formula.

Control value (%)={1−($Cb \times Tai$)/($Cai \times Tb$)}×100

Letters in the formula represent the following meanings.
Cb: insect number before treatment on non-treated area
Cai: insect number in observation on non-treated area
Tb: insect number before treatment on treated area
Tai: insect number in observation on treated area As a result, the treated areas treated by the present compounds (1), (2), (4) to (12), (14) to (17) and (19) showed a control value of 90% or more.

Test Example 2

The present compounds (7), (9), (12), (14), (16) and (17) were formulated by the method in Formulation Example 5.

This formulation was diluted with water so that the active ingredient concentration was 500 ppm, to prepare a diluted solution for test.

This diluted solution for test (5 ml) was placed in a plastic cup. A soil around a cucumber seedling (first true leaf spreading stage) was removed, and a root part of this seedling was washed with water. The root part of this seedling was immersed in the diluted solution for test placed in the above-described plastic cup. One day after, the cucumber leaf surface was inoculated with 30 *Aphis gossypii* (whole stage). Further 7 days after, the insect number of living *Aphis gossypii* parasitic on the leaves of this cucumber was checked. The control value was calculated according to the following formula.

Control value (%)={1−(Cb×Tai)/(Cai×Tb)}×100

Letters in the formula represent the following meanings.
Cb: insect number before treatment on non-treated area
Cai: insect number in observation on non-treated area
Tb: insect number before treatment on treated area
Tai: insect number in observation on treated area
As a result, the treated areas treated by the present compounds (7), (9), (12), (14), (16) and (17) showed a control value of 90% or more.

Test Example 3

The present compound (7) was formulated by the method in Formulation Example 5. This formulation was diluted with water so that the active ingredient concentration was 200 ppm, to prepare a diluted solution for test.

The diluted solution for test (5 ml) was used to treat a foot of a cucumber seedling (first true leaf spreading stage) planted in a plastic cup. This cucumber was left in a greenhouse at 25° C. for 7 days. Then; the cucumber leaf surface was inoculated with 30 *Aphis gossypii* (whole stage). This cucumber was further left in the greenhouse for 6 days, then, the insect number of living *Aphis gossypii* parasitic on the leaves of this cucumber was checked, and the control value was calculated according to the following formula.

Control value (%)={1−(Cb×Tai)/(Cai×Tb)}×100

Letters in the formula represent the following meanings.
Cb: insect number before treatment on non-treated area
Cai: insect number in observation on non-treated area
Tb: insect number before treatment on treated area
Tai: insect number in observation on treated area
As a result, the treated area treated by the diluted solution for test of the present compound (7) showed a control value of 90% or more.

Test Example 4

The present compounds (1), (4) to (7), (9) to (12) and (14) to (19) were formulated by the method in Formulation Example 5. This formulation was diluted with water so that the active ingredient concentration was 200 ppm, to prepare a diluted solution for test.

On a tomato seedling planted in a plastic cup, *Bemisia tabaci* adult insects were released and allowed to lay eggs for about 24 hours. The tomato seedling was left in a greenhouse for 8 days. Thereafter, the diluted solution for test was sprayed in a proportion of 10 ml/cup. Further, this tomato seedling was placed in a greenhouse at 25° C. for 7 days. Thereafter, the number of larvae living on the tomato leaves was checked, and the control value was calculated according to the following formula.

Control value (%)={1−(Cb×Tai)/(Cai×Tb)}×100

Letters in the formula represent the following meanings.
Cb: insect number before treatment on non-treated area
Cai: insect number in observation on non-treated area
Tb: insect number before treatment on treated area
Tai: insect number in observation on treated area
As a result, the treated areas treated by the present compounds (1), (4) to (7), (9) to (12) and (14) to (19) showed a control value of 90% or more.

Test Example 5

The present compounds (1) to (7), (9) to (15) and (17) to (19) were formulated by the method in Formulation Example 5. This formulation was diluted with water so that the active ingredient concentration was 500 ppm, to prepare a diluted solution for test.

On a rice seedling (2 weeks after sowing, second leaf spreading stage) planted in aplastic cup, the diluted solution for test (10 ml) was sprayed. The drug solution sprayed to treat the rice seedling was dried, then, 20 first instar larvae of *Nilaparvata lugens* were released. This rice seedling was placed in a greenhouse at 25° C. for 6 days. Thereafter, the number of *Nilaparvata lugens* parasitic on rice was checked, and the control value was calculated according to the following formula.

Control value (%)={1−(Cb×Tai)/(Cai×Tb)}×100

Letters in the formula represent the following meanings.
Cb: insect number before treatment on non-treated area
Cai: insect number in observation on non-treated area
Tb: insect number before treatment on treated area
Tai: insect number in observation on treated area
As a result, the treated areas treated by the present compounds (1) to (7), (9) to (15) and (17) to (19) showed a control value of 90% or more.

Industrial Applicability

The present compound is useful for control of arthropod pests.

The invention claimed is:

1. A heterocyclic compound represented by formula (1):

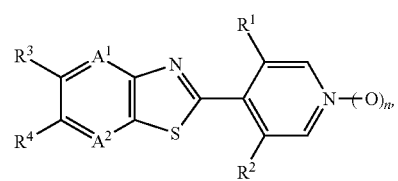

wherein
$A^1$ and $A^2$ are the same or different and represent a nitrogen atom or $=C(R^5)-$,
$R^1$ represents a C1-C6 chain hydrocarbon group optionally substituted by at least one member selected from Group X, C3-C6 alicyclic hydrocarbon group optionally substituted by at least one member selected from Group X, phenyl group optionally substituted by at least one member selected from Group Y 5-membered heterocyclic group optionally substituted by at least one member selected from Group Y, 6-membered heterocyclic group optionally substituted by at least one member selected from Group Y, —OR$^6$, —S(O)$_m$R$^6$, —NR$^6$R$^7$, —NR$^6$C(O)R$^8$, —NR$^6$CO$_2$R$^9$, —C(O)R$^{10}$, —C(NOR$^6$)R$^{10}$, cyano group, nitro group or halogen atom, R$^2$ represents a C1-C6 chain hydrocarbon group optionally substituted by at least one member selected from Group X, —OR$^6$, —S(O)$_m$R$^6$, —NR$^6$R$^7$, halogen atom or hydrogen atom, R$^3$ and R$^4$ are the same or different and represent a C1-C4 chain hydrocarbon group substituted by at least one halogen atom, —OR$^{11}$, —S(O)$_m$R$^{11}$, halogen atom or hydrogen atom (with the proviso that either R$^3$ or R$^4$ represents a C1-C4 chain hydrocarbon group substituted by at least one halogen atom, —OR$^{11}$ or —S(O)$_m$R$^{11}$), alternatively, R$^3$ and R$^4$ may be bound to form a 5-membered ring or 6-membered ring substituted by one or more halogen atoms together with the carbon atoms to which R$^3$ and R$^4$ are connected, R$^5$ represents a C1-C3 alkyl group optionally substituted by at least one halogen atom, halogen atom or hydrogen atom, R$^6$ and R$^7$ are the same or different and represent a C1-C6 chain hydrocarbon group optionally substituted by at, least one member selected from Group X, C4-C7 cycloalkylmethyl group optionally substituted by at least one member selected from Group X, C3-C6 alicyclic hydrocarbon group optionally substituted by at least one member selected from Group X, phenyl group optionally substituted by at least one member selected from Group Y, benzyl group optionally substituted by at least one member selected from Group Y, 5-membered heterocyclic group optionally substituted by at least one member selected from Group Y, 6-membered heterocyclic group optionally substituted by at least one member selected from Group Y, or hydrogen atom (with the proviso that R$^6$ does not represent a hydrogen atom when m in —S(O)$_m$R$^6$ is 1 or 2)

R$^8$ represents a C1-C6 chain hydrocarbon group optionally substituted by at least one member selected from Group X, C3-C6 alicyclic hydrocarbon group optionally substituted by at least one member selected from Group X, or phenyl group optionally substituted by at least one member selected from Group Y, R$^9$ represents a C1-C4 alkyl group optionally substituted by at least one halogen atom, R$^{10}$ R represents a C1-C4 alky group optionally substituted by at least one halogen atom, or hydrogen atom, R$^{11}$ represents a C1-C4 chain hydrocarbon group substituted by at least one halogen atom, m represents 0, 1 or 2, and n represents 0 or 1;

Group X: the group consisting of C1-C4 alkoxy groups optionally substituted by at least one halogen atom, and halogen atoms;

Group Y: the group consisting of C 1-C4 alkyl groups optionally substituted by at least one halogen atom, C1-C4 alkoxy groups optionally substituted by at least one halogen atom, cyano group, nitro group and halogen atoms.

2. The heterocyclic compound according to claim 1, wherein R$^5$ is a hydrogen atom.

3. The heterocyclic compound according to claim 1, wherein R$^2$ is a hydrogen atom.

4. The heterocyclic compound according to claim 1, wherein R$^1$ is a C1-C6 chain hydrocarbon group optionally substituted by at least one member selected from Group X, —OR$^6$, —S(O)$_m$R$^6$, —NR$^6$R$^7$, —NR$^6$C(O)R$^8$, —NR$^6$CO$_2$R$^9$, —C(O)R$^{10}$, —C(NOR$^6$)R$^{10}$, cyano group, nitro group or halogen atom, R$^6$ and R$^7$ are the same or different and are a C1-C6 chain hydrocarbon group optionally substituted by at least one member selected from Group X, or hydrogen atom (with the proviso that R$^6$ is a C1-C6 chain hydrocarbon group optionally substituted by at least one member selected from Group X when m in —S(O)$_m$R$^6$ is 1 or 2), and R$^8$ is a C1-C6 chain hydrocarbon group optionally substituted by at least one member selected from Group X.

5. The heterocyclic compound acco d ng to claim 4, wherein R$^1$ is a C1-C6 chain hydrocarbon group optionally substituted by at least one member selected from Group X, —OR$^6$, —S(O)$_m$R$^6$, —NR$^6$R$^7$ or halogen atom, R$^6$ is a C1-C6 chain hydrocarbon group optionally substituted by at least one member selected from Group X, and R$^7$ R is a C1-C6 chain hydrocarbon group optionally substituted by at least one member selected from Group X, or hydrogen atom.

6. An arthropod pest control composition comprising the heterocyclic compound as described in claim 1, and, an inert carrier.

7. An arthropod pest control method comprising applying an effective amount of the heterocyclic compound as described in claim 1 to arthropod pests or areas where arthropod pests live.

8. The heterocyclic compound according to claim 1, wherein R$^3$ is a C1-C4 chain hydrocarbon substituted by at least one halogen atom and R$^4$ is a hydrogen atom.

9. The heterocyclic compound according to claim 1, wherein R$^3$ is —OR$^{11}$, R$^{11}$ is a C1-C4 chain hydrocarbon group substituted by at least one fluorine atom and R$^4$ is a hydrogen atom.

10. The heterocyclic compound according to claim 1, wherein R$^3$ is a C1-C4 chain hydrocarbon group substituted by at least one fluorine atom and R$^4$ is a hydrogen atom.

11. The heterocyclic compound according to claim 1, wherein R$^3$ is a hydrogen atom and R$^4$ is a C1-C4 chain hydrocarbon group substituted by at least one halogen atom.

12. The heterocyclic compound according to claim 1, wherein R$^3$ is a hydrogen atom and R$^4$ is a C1-C4 chain hydrocarbon group substituted by at least one fluorine atom.

13. The heterocyclic compound according to claim 1, wherein R$^3$ is a hydrogen atom, R$^4$ is —OR$^{11}$, and R$^{11}$ is a C1-C4 chain hydrocarbon group substituted by at least one fluorine atom.

14. The heterocyclic compound according to claim 1, wherein R$^3$ is a trifluoromethyl group and R$^4$ is a hydrogen atom.

15. The heterocyclic compound according to claim 1, wherein R$^3$ is —OR$^{11}$, R$^{11}$ is a trifluoromethyl group and R$^4$ is a hydrogen atom.

16. The heterocyclic compound according to claim 1, wherein R$^3$ is a hydrogen atom and R$^4$ is a trifluoromethyl group.)

17. The heterocyc c compound according to claim 1, wherein R$^3$ is a hydrogen atom, R$^4$ is —OR$^{11}$ and R$^{11}$ is a trifluoromethyl group.

* * * * *